(12) United States Patent
Desjarlais et al.

(10) Patent No.: US 9,040,041 B2
(45) Date of Patent: May 26, 2015

(54) MODIFIED FC MOLECULES

(75) Inventors: John R. Desjarlais, Pasadena, CA (US); Sher Bahadur Karki, Pasadena, CA (US); Gregory Alan Lazar, Arcadia, CA (US); John O. Richards, Monrovia, CA (US); Gregory L. Moore, Pasadena, CA (US); David F. Carmichael, Monrovia, CA (US)

(73) Assignee: Xencor, Inc., Monrovia, CA (US)

( * ) Notice: Subject to any disclaimer, the term of this patent is extended or adjusted under 35 U.S.C. 154(b) by 510 days.

(21) Appl. No.: 12/794,560

(22) Filed: Jun. 4, 2010

(65) Prior Publication Data

US 2010/0249382 A1    Sep. 30, 2010

Related U.S. Application Data

(63) Continuation of application No. 11/981,647, filed on Oct. 31, 2007, now abandoned, which is a continuation of application No. 11/538,406, filed on Oct. 3, 2006, now abandoned, application No. 12/794,560, which is a continuation-in-part of application No. 11/396,495, filed on Mar. 31, 2006, now abandoned.

(60) Provisional application No. 60/741,966, filed on Dec. 2, 2005, provisional application No. 60/779,961, filed on Mar. 6, 2006, provisional application No. 60/745,078, filed on Apr. 18, 2006, provisional application No. 60/723,294, filed on Oct. 3, 2005, provisional application No. 60/723,335, filed on Oct. 3, 2005, provisional application No. 60/739,696, filed on Nov. 23, 2005, provisional application No. 60/774,358, filed on Feb. 17, 2006, provisional application No. 60/750,699, filed on Dec. 15, 2005.

(51) Int. Cl.
   *A61K 39/395* (2006.01)
   *A61K 39/40* (2006.01)
   *C07K 16/00* (2006.01)

(52) U.S. Cl.
   CPC ............ *C07K 16/00* (2013.01); *C07K 2317/41* (2013.01); *C07K 2317/732* (2013.01); *C07K 2317/77* (2013.01); *C07K 2317/52* (2013.01)

(58) Field of Classification Search
   None
   See application file for complete search history.

(56) References Cited

U.S. PATENT DOCUMENTS

| | | |
|---|---|---|
| 3,773,919 A | 11/1973 | Boswell et al. |
| 4,485,045 A | 11/1984 | Regen et al. |
| 4,544,545 A | 10/1985 | Ryan et al. |
| 4,753,894 A | 6/1988 | Frankel et al. |
| 4,816,397 A | 3/1989 | Boss et al. |
| 4,816,567 A | 3/1989 | Cabilly et al. |
| 4,943,533 A | 7/1990 | Mendelsohn et al. |
| 4,975,278 A | 12/1990 | Senter et al. |
| 5,208,020 A | 5/1993 | Chari et al. |
| 5,225,348 A | 7/1993 | Nagata et al. |
| 5,225,539 A | 7/1993 | Winter et al. |
| 5,264,586 A | 11/1993 | Nicolaou et al. |
| 5,266,491 A | 11/1993 | Nagata et al. |
| 5,328,987 A | 7/1994 | Maliszewski |
| 5,500,362 A | 3/1996 | Robinson et al. |
| 5,530,101 A | 6/1996 | Queen et al. |
| 5,541,087 A | 7/1996 | Lo et al. |
| 5,558,864 A | 9/1996 | Bendig et al. |
| 5,576,184 A | 11/1996 | Better et al. |
| 5,585,089 A | 12/1996 | Queen et al. |
| 5,623,053 A | 4/1997 | Gastinel et al. |
| 5,624,821 A | 4/1997 | Winter et al. |
| 5,633,162 A | 5/1997 | Keen et al. |
| 5,648,237 A | 7/1997 | Carter |
| 5,648,260 A | 7/1997 | Winter et al. |
| 5,658,570 A | 8/1997 | Newman et al. |
| 5,677,171 A | 10/1997 | Hudziak et al. |
| 5,681,566 A | 10/1997 | Stevenson et al. |
| 5,693,761 A | 12/1997 | Queen et al. |
| 5,693,762 A | 12/1997 | Queen et al. |
| 5,712,374 A | 1/1998 | Kuntsmann et al. |
| 5,714,586 A | 2/1998 | Kuntsmann et al. |
| 5,736,137 A | 4/1998 | Anderson et al. |
| 5,750,105 A | 5/1998 | Newman et al. |
| 5,773,001 A | 6/1998 | Hamann et al. |
| 5,804,396 A | 9/1998 | Plowman et al. |
| 5,821,337 A | 10/1998 | Carter et al. |
| 5,834,597 A | 11/1998 | Tso et al. |
| 5,859,205 A | 1/1999 | Adair et al. |
| 5,885,573 A | 3/1999 | Bluestone et al. |
| 5,891,996 A | 4/1999 | Mateo De Acosta Del et al. |
| 6,030,613 A | 2/2000 | Blumberg et al. |

(Continued)

FOREIGN PATENT DOCUMENTS

| | | |
|---|---|---|
| EP | 1 255 826 B1 | 0/2002 |
| EP | 0 268 636 B1 | 1/1997 |

(Continued)

OTHER PUBLICATIONS

Huls et al. Cancer Research 59, 5778-5784, Nov. 15, 1999.*

(Continued)

*Primary Examiner* — Chun Dahle
(74) *Attorney, Agent, or Firm* — Robin M. Silva; Christina MacDougall; Morgan, Lewis & Bockius, LLP

(57) ABSTRACT

The present invention relates to Fc variants with optimized Fc receptor binding properties, methods for their generation, Fc polypeptides comprising Fc variants with optimized Fc receptor binding properties, and methods for using Fc variants with optimized Fc receptor binding properties.

3 Claims, 31 Drawing Sheets

(56) References Cited

U.S. PATENT DOCUMENTS

| | | |
|---|---|---|
| 6,054,297 A | 4/2000 | Carter et al. |
| 6,086,875 A | 7/2000 | Blumberg et al. |
| 6,121,022 A | 9/2000 | Presta et al. |
| 6,165,745 A | 12/2000 | Ward et al. |
| 6,180,370 B1 | 1/2001 | Queen et al. |
| 6,188,965 B1 | 2/2001 | Mayo et al. |
| 6,194,551 B1 | 2/2001 | Idusogie et al. |
| 6,235,883 B1 | 5/2001 | Jakobovits et al. |
| 6,242,195 B1 | 6/2001 | Idusogie et al. |
| 6,269,312 B1 | 7/2001 | Mayo et al. |
| 6,277,375 B1 | 8/2001 | Ward |
| 6,284,536 B1 | 9/2001 | Morrison et al. |
| 6,331,415 B1 | 12/2001 | Cabilly et al. |
| 6,358,733 B1 | 3/2002 | Motwani et al. |
| 6,365,161 B1 | 4/2002 | Deo et al. |
| 6,403,312 B1 | 6/2002 | Dahiyat et al. |
| 6,407,213 B1 | 6/2002 | Carter et al. |
| 6,444,789 B1 | 9/2002 | Luo |
| 6,485,726 B1 | 11/2002 | Blumberg et al. |
| 6,506,883 B2 | 1/2003 | Del Rio et al. |
| 6,528,624 B1 | 3/2003 | Idusogie et al. |
| 6,538,124 B1 | 3/2003 | Idusogie et al. |
| 6,602,684 B1 | 8/2003 | Umana et al. |
| 6,632,927 B2 | 10/2003 | Adair et al. |
| 6,649,165 B2 | 11/2003 | Schubert |
| 6,708,120 B1 | 3/2004 | Mayo et al. |
| 6,719,971 B1 | 4/2004 | Carter et al. |
| 6,737,056 B1 | 5/2004 | Presta |
| 6,792,356 B2 | 9/2004 | Mayo et al. |
| 6,797,492 B2 | 9/2004 | Daugherty et al. |
| 6,801,861 B2 | 10/2004 | Mayo et al. |
| 6,804,611 B2 | 10/2004 | Mayo et al. |
| 6,821,505 B2 | 11/2004 | Ward |
| 6,875,846 B2 | 4/2005 | Rennert et al. |
| 6,933,368 B2 | 8/2005 | Co et al. |
| 6,946,292 B2 | 9/2005 | Kanda et al. |
| 6,950,754 B2 | 9/2005 | Mayo et al. |
| 6,982,321 B2 | 1/2006 | Winter |
| 6,992,234 B2 | 1/2006 | Roopenian |
| 7,056,695 B2 | 6/2006 | Dahiyat et al. |
| 7,083,784 B2 | 8/2006 | Dall'Acqua et al. |
| 7,101,974 B2 | 9/2006 | Dahiyat et al. |
| 7,117,096 B2 | 10/2006 | Luo et al. |
| 7,244,823 B2 | 7/2007 | Dahiyat et al. |
| 7,247,301 B2 | 7/2007 | van de Winkel et al. |
| 7,276,585 B2 | 10/2007 | Lazar et al. |
| 7,315,786 B2 | 1/2008 | Dahiyat et al. |
| 7,317,091 B2 | 1/2008 | Lazar et al. |
| 7,355,008 B2 | 4/2008 | Stavenhagen et al. |
| 7,662,925 B2 | 2/2010 | Lazar et al. |
| 7,863,419 B2 | 1/2011 | Taylor et al. |
| 8,039,592 B2 | 10/2011 | Lazar et al. |
| 8,084,582 B2 | 12/2011 | Dahiyat et al. |
| 8,093,357 B2 | 1/2012 | Lazar et al. |
| 8,093,359 B2 | 1/2012 | Lazar et al. |
| 8,101,720 B2 | 1/2012 | Lazar et al. |
| 8,124,731 B2 | 2/2012 | Lazar et al. |
| 8,188,231 B2 | 5/2012 | Lazar et al. |
| 8,318,907 B2 | 11/2012 | Chamberlain et al. |
| 8,324,351 B2 | 12/2012 | Chamberlain et al. |
| 8,338,574 B2 | 12/2012 | Chamberlain et al. |
| 8,367,805 B2 | 2/2013 | Chamberlain et al. |
| 8,383,109 B2 | 2/2013 | Lazar et al. |
| 8,388,955 B2 | 3/2013 | Lazar et al. |
| 2001/0036459 A1 | 11/2001 | Ravetch |
| 2001/0044003 A1 | 11/2001 | Gallucci et al. |
| 2002/0004587 A1 | 1/2002 | Miller et al. |
| 2002/0048772 A1 | 4/2002 | Dahiyat et al. |
| 2002/0062010 A1 | 5/2002 | Arathoon et al. |
| 2002/0090648 A1 | 7/2002 | Dahiyat et al. |
| 2002/0119492 A1 | 8/2002 | Chirino et al. |
| 2002/0142374 A1 | 10/2002 | Gallo et al. |
| 2002/0155537 A1 | 10/2002 | Carter et al. |
| 2002/0164328 A1 | 11/2002 | Shinkawa et al. |
| 2002/0168640 A1 | 11/2002 | Li et al. |
| 2002/0172968 A1 | 11/2002 | Liu et al. |
| 2002/0192222 A1 | 12/2002 | Blumberg et al. |
| 2003/0003097 A1 | 1/2003 | Reff et al. |
| 2003/0012789 A1 | 1/2003 | Blumberg et al. |
| 2003/0022285 A1 | 1/2003 | Chirino et al. |
| 2003/0036643 A1 | 2/2003 | Jin et al. |
| 2003/0049647 A1 | 3/2003 | Dahiyat et al. |
| 2003/0049654 A1 | 3/2003 | Dahiyat et al. |
| 2003/0068649 A1 | 4/2003 | Doberstein et al. |
| 2003/0073164 A1 | 4/2003 | Simmons et al. |
| 2003/0078385 A1 | 4/2003 | Arathoon et al. |
| 2003/0105294 A1 | 6/2003 | Gilles et al. |
| 2003/0108548 A1 | 6/2003 | Bluestone et al. |
| 2003/0118592 A1 | 6/2003 | Ledbetter et al. |
| 2003/0124537 A1 | 7/2003 | Liu et al. |
| 2003/0130827 A1 | 7/2003 | Bentzien et al. |
| 2003/0133939 A1 | 7/2003 | Ledbetter et al. |
| 2003/0143682 A1 | 7/2003 | Nicolaides et al. |
| 2003/0157108 A1 | 8/2003 | Presta |
| 2003/0158289 A1 | 8/2003 | Rusin et al. |
| 2003/0158389 A1 | 8/2003 | Idusogie et al. |
| 2003/0166868 A1 | 9/2003 | Presta et al. |
| 2003/0175884 A1 | 9/2003 | Umana et al. |
| 2003/0190311 A1 | 10/2003 | Dall'Acqua et al. |
| 2003/0208054 A1 | 11/2003 | Olsen et al. |
| 2003/0224397 A1 | 12/2003 | Lowman et al. |
| 2003/0229208 A1 | 12/2003 | Queen et al. |
| 2003/0235536 A1 | 12/2003 | Blumberg et al. |
| 2004/0002587 A1 | 1/2004 | Watkins et al. |
| 2004/0043429 A1 | 3/2004 | Dahiyat et al. |
| 2004/0043430 A1 | 3/2004 | Dahiyat et al. |
| 2004/0062763 A1 | 4/2004 | Mosser et al. |
| 2004/0093621 A1 | 5/2004 | Shitara et al. |
| 2004/0110226 A1 | 6/2004 | Lazar et al. |
| 2004/0132101 A1 | 7/2004 | Lazar et al. |
| 2004/0185045 A1 | 9/2004 | Koenig et al. |
| 2004/0191244 A1 | 9/2004 | Presta |
| 2004/0191256 A1 | 9/2004 | Raju |
| 2004/0192897 A2 | 9/2004 | Winter |
| 2004/0228856 A1 | 11/2004 | Presta |
| 2004/0258677 A1 | 12/2004 | Waldmann et al. |
| 2004/0258682 A1 | 12/2004 | Leung et al. |
| 2004/0259150 A1 | 12/2004 | Nakamura et al. |
| 2005/0014934 A1 | 1/2005 | Hinton et al. |
| 2005/0031626 A1 | 2/2005 | Stevenson |
| 2005/0032114 A1 | 2/2005 | Hinton et al. |
| 2005/0033029 A1 | 2/2005 | Lu |
| 2005/0037000 A1 | 2/2005 | Stavenhagen et al. |
| 2005/0037002 A1 | 2/2005 | Velardi et al. |
| 2005/0038610 A1 | 2/2005 | Mayo et al. |
| 2005/0054046 A1 | 3/2005 | Presta et al. |
| 2005/0054832 A1* | 3/2005 | Lazar et al. ................ 530/387.3 |
| 2005/0064514 A1 | 3/2005 | Stavenhagen et al. |
| 2005/0118174 A1 | 6/2005 | Presta |
| 2005/0152894 A1 | 7/2005 | Krummen et al. |
| 2005/0175614 A1 | 8/2005 | Ledbetter et al. |
| 2005/0180948 A1 | 8/2005 | Desjarlais et al. |
| 2005/0202023 A1 | 9/2005 | Ledbetter et al. |
| 2005/0202028 A1 | 9/2005 | Ledbetter et al. |
| 2005/0202534 A1 | 9/2005 | Ledbetter et al. |
| 2005/0215767 A1 | 9/2005 | Koenig et al. |
| 2005/0226864 A1 | 10/2005 | Hinton et al. |
| 2005/0233382 A1 | 10/2005 | Presta |
| 2005/0272128 A1 | 12/2005 | Umana et al. |
| 2005/0276799 A1 | 12/2005 | Hinton et al. |
| 2006/0008883 A1 | 1/2006 | Lazar et al. |
| 2006/0019316 A1 | 1/2006 | Mayo et al. |
| 2006/0235208 A1 | 10/2006 | Lazar et al. |
| 2006/0275283 A1* | 12/2006 | van Vlijmen et al. ...... 424/130.1 |
| 2007/0087005 A1 | 4/2007 | Lazar et al. |
| 2007/0148164 A1 | 6/2007 | Farrington et al. |

(56) References Cited

U.S. PATENT DOCUMENTS

| | | |
|---|---|---|
| 2007/0224192 A1 | 9/2007 | Lazar et al. |
| 2007/0238665 A1 | 10/2007 | Lazar et al. |
| 2008/0071063 A1 | 3/2008 | Allan et al. |
| 2008/0206867 A1 | 8/2008 | Desjarlais et al. |

FOREIGN PATENT DOCUMENTS

| | | |
|---|---|---|
| EP | 1 176 195 A1 | 1/2002 |
| EP | 1 229 125 A1 | 8/2002 |
| EP | 1355919 | 8/2002 |
| EP | 1 255 209 A2 | 11/2002 |
| EP | 0 753 065 B1 | 5/2003 |
| EP | 0 805 628 B1 | 5/2003 |
| EP | 1 323 346 A2 | 11/2003 |
| EP | 1 323 346 A3 | 11/2003 |
| EP | 0 888 125 B1 | 5/2004 |
| EP | 0 904 107 B1 | 10/2004 |
| EP | 0 383 799 B2 | 2/2005 |
| WO | WO81/01145 | 4/1981 |
| WO | WO 88/07089 A1 | 9/1988 |
| WO | WO88/07378 | 10/1988 |
| WO | WO 91/06305 A1 | 5/1991 |
| WO | WO91/06305 A1 | 5/1991 |
| WO | WO91/19515 A1 | 12/1991 |
| WO | WO 91/19515 A1 | 12/1991 |
| WO | WO92/04053 A1 | 3/1992 |
| WO | WO 92/04053 A1 | 3/1992 |
| WO | WO 92/16562 A1 | 10/1992 |
| WO | WO92/16562 A1 | 10/1992 |
| WO | WO 92/22324 A1 | 12/1992 |
| WO | WO93/21232 | 10/1993 |
| WO | WO93/22332 | 11/1993 |
| WO | WO94/11026 | 5/1994 |
| WO | WO 94/29351 A2 | 12/1994 |
| WO | WO 94/29351 A3 | 12/1994 |
| WO | WO 95/05468 A1 | 2/1995 |
| WO | WO95/20045 | 7/1995 |
| WO | WO 96/22024 A1 | 7/1996 |
| WO | WO96/30347 | 10/1996 |
| WO | WO96/33978 | 10/1996 |
| WO | WO96/40210 | 12/1996 |
| WO | WO 97/28267 A1 | 8/1997 |
| WO | WO 97/34631 A1 | 9/1997 |
| WO | WO97/38731 | 10/1997 |
| WO | WO97/38983 | 10/1997 |
| WO | WO 98/02462 A1 | 1/1998 |
| WO | WO 98/05787 A1 | 2/1998 |
| WO | WO 98/23289 A1 | 6/1998 |
| WO | WO98/43960 | 10/1998 |
| WO | WO 98/47089 A1 | 11/1998 |
| WO | WO98/52976 | 11/1998 |
| WO | WO98/59244 | 12/1998 |
| WO | WO 99/04813 A1 | 2/1999 |
| WO | WO99/06378 | 2/1999 |
| WO | WO99/06396 | 2/1999 |
| WO | WO99/09016 | 2/1999 |
| WO | WO 99/51642 A1 | 10/1999 |
| WO | WO 99/54342 A1 | 10/1999 |
| WO | WO99/54484 A1 | 10/1999 |
| WO | WO 99/58572 A1 | 11/1999 |
| WO | WO 00/09560 A2 | 2/2000 |
| WO | WO 00/09560 A3 | 2/2000 |
| WO | WO 00/23564 A2 | 4/2000 |
| WO | WO 00/23564 A3 | 4/2000 |
| WO | WO 00/24782 A2 | 5/2000 |
| WO | WO 00/24782 A3 | 5/2000 |
| WO | WO 00/42072 A2 | 7/2000 |
| WO | WO 00/42072 A3 | 7/2000 |
| WO | WO 00/61739 A1 | 10/2000 |
| WO | WO01/14539 | 1/2001 |
| WO | WO 01/29246 A1 | 4/2001 |
| WO | WO 01/38490 A2 | 5/2001 |
| WO | WO 01/57088 A1 | 8/2001 |
| WO | WO 01/59066 A2 | 8/2001 |
| WO | WO 01/59066 A3 | 8/2001 |
| WO | WO01/62931 | 8/2001 |
| WO | WO01/88138 | 11/2001 |
| WO | WO02/05146 | 1/2002 |
| WO | WO02/22826 | 3/2002 |
| WO | WO 02/30954 A1 | 4/2002 |
| WO | WO 02/31140 A1 | 4/2002 |
| WO | WO 02/44215 A2 | 6/2002 |
| WO | WO 02/060919 A2 | 8/2002 |
| WO | WO 02/060919 A3 | 8/2002 |
| WO | WO 02/061090 A3 | 8/2002 |
| WO | WO 02/061093 A1 | 8/2002 |
| WO | WO02/066514 A | 8/2002 |
| WO | WO02/066653 | 8/2002 |
| WO | WO02/068453 | 9/2002 |
| WO | WO02/068698 | 9/2002 |
| WO | WO02/069232 | 10/2002 |
| WO | WO02/077187 | 10/2002 |
| WO | WO02/079232 A2 | 10/2002 |
| WO | WO03/000405 | 1/2003 |
| WO | WO03/006154 | 1/2003 |
| WO | WO 03/014325 A2 | 2/2003 |
| WO | WO 03/014325 A3 | 2/2003 |
| WO | WO 03/016470 A2 | 2/2003 |
| WO | WO03/025154 | 3/2003 |
| WO | WO 03/035835 A2 | 5/2003 |
| WO | WO 03/035835 A3 | 5/2003 |
| WO | WO 03/054213 A2 | 7/2003 |
| WO | WO03/059282 A | 7/2003 |
| WO | WO 03/059282 A | 7/2003 |
| WO | WO03/074679 | 9/2003 |
| WO | WO 03/074679 | 9/2003 |
| WO | WO 03/089624 A2 | 10/2003 |
| WO | WO 2004/004662 A2 | 1/2004 |
| WO | WO 2004/004798 A2 | 1/2004 |
| WO | WO 2004/004798 A3 | 1/2004 |
| WO | WO 2004/016750 A3 | 2/2004 |
| WO | WO 2004/022717 A2 | 3/2004 |
| WO | WO 2004/022717 A3 | 3/2004 |
| WO | WO 2004/024871 A2 | 3/2004 |
| WO | WO 2004/024889 A2 | 3/2004 |
| WO | WO2004/029207 A | 4/2004 |
| WO | WO 2004/029207 A | 4/2004 |
| WO | WO 2004/035752 A2 | 4/2004 |
| WO | WO 2004/056312 A2 | 7/2004 |
| WO | WO 2004/063351 A2 | 7/2004 |
| WO | WO 2004/063351 A3 | 7/2004 |
| WO | WO2004/063963 A | 7/2004 |
| WO | WO2004063963 A | 7/2004 |
| WO | WO 2004/074455 A2 | 9/2004 |
| WO | WO 2004/074455 A3 | 9/2004 |
| WO | WO2004/091658 | 10/2004 |
| WO | WO 2004/092219 A2 | 10/2004 |
| WO | WO2004/099249 A | 11/2004 |
| WO | WO 2004/103404 A1 | 12/2004 |
| WO | WO 2004/110472 A2 | 12/2004 |
| WO | WO 2005/000899 A2 | 1/2005 |
| WO | WO 2005/001025 A2 | 1/2005 |
| WO | WO 2005/007809 A2 | 1/2005 |
| WO | WO 2005/011376 A2 | 2/2005 |
| WO | WO 2005/012877 A2 | 2/2005 |
| WO | WO 2005/013090 A2 | 2/2005 |
| WO | WO 2005/018572 A2 | 3/2005 |
| WO | WO 2005/023866 A2 | 3/2005 |
| WO | WO 2005/027966 A2 | 3/2005 |
| WO | WO 2005/037867 A1 | 4/2005 |
| WO | WO 2005/040217 A2 | 5/2005 |
| WO | WO 2005/047327 A2 | 5/2005 |
| WO | WO2005/047327 A2 | 5/2005 |
| WO | WO 2005/056606 A | 6/2005 |
| WO | WO2005/056606 A | 6/2005 |
| WO | WO2005/056759 A | 6/2005 |
| WO | WO 2005/056759 A | 6/2005 |
| WO | WO 2005/060642 A2 | 7/2005 |
| WO | WO 2005/063815 A2 | 7/2005 |
| WO | WO 2005/070963 A1 | 8/2005 |
| WO | WO 2005/116078 A1 | 12/2005 |
| WO | WO2005/123780 A2 | 12/2005 |
| WO | WO 2005/123780 A2 | 12/2005 |

(56) References Cited

FOREIGN PATENT DOCUMENTS

| WO | WO2006/012500 A2 | 2/2006 |
|---|---|---|
| WO | WO 2006/012500 A2 | 2/2006 |
| WO | WO2006105338 | 10/2006 |
| WO | WO2007008943 | 1/2007 |
| WO | WO2007/044616 | 4/2007 |
| WO | WO2009086320 | 7/2009 |

OTHER PUBLICATIONS

Aase, A. et al. "The extended hinge region of IgG3 is not required for high phogocytic capacity mediated by Fc gamma receptors, but the heavy chains must be disulfide bonded," *Eur J Immunol.*, 23(7):1546-1551 (Jul. 1993).
Abadeh, S., et al., "Remodelling the oligosaccharide of human IgG antibodies: effects on biological activities," *Biochem Soc Trans.*, 25(4):S661 (Nov. 1997).
Akewanlop, C., et al., "Phagocytosis of Breast Cancer Cells Mediated by Anti-MUC-1 Monoclonal antibody, DF3, and Its Bispecific Antibody" *Cancer Research*, 61:4061-4065 (May 15, 2001).
Alegre, M., et al., "Effect of a Single Amino Acid Mutation on the Activating and Immunosuppressive Properties of a "Humanised" OKT3 Monoclonal Antibody," *J. Immunology*, 148:3461-3468 (Jun. 1992).
Algre, et al., "A non-activating "humanized" anti-CD3 monoclonal antibody retains immunosuppressive properties in vivo," *Transplantation*, 57:1537-1543 (1994).
Amigorena, S., et al., "Fc receptors for IgG and antigen presentation on MHC class I and class II molecules" *Immunology*, 11:385-390 (1999).
Andreakos, E., et al., "Monoclonal antibodies in immune and inflammatory diseases," *Curr. Opin. Biotech.*, 13:615-620 (2002).
Armour, et al., "Recombinant human IgG molecules lacking Fcgamma receptor I binding and monocyte triggering activities," *Eur J Immunol*, 29:2613-2624 (1999).
Armour, K. L., et al., "Differential binding to human Fcγ RIIa and Fcγ RIIb receptors by human IgG wildtype and mutant antibodies," *Molecular Immunology*, 40:585-593 (2003).
Ashkenazi, A., et al., "Mapping the CD4 binding site for human immunodeficiency virus by alanine-scanning mutagenesis," *PNAS, USA*, 87:7150-7154 (Sep. 1990).
Ashkenazi, et al., "Immunoadhesins as research tools and therapeutic agents," *Curr Opin Immunol*, 9:195-200 (1997).
Bastida-Corcuera, et al., "Differential complement activation by bovine IgG2 allotypes" Veterinary Immunology and Immunopathology, 1999, vol. 71 No. 2, 115-123.
Bolland, S. "A Newly Discovered Fc Receptor tha Explains IgG-Isotype Disparities in Effector Responses," *J. Immunity*, 23:2-4 (Jul. 2005).
Boruchov, A. M., et al., "Activating and inhibitory IgG Fc receptors on human DCs mediate opposing functions" *J. Clin. Invest.* doi:10.1172/JCI24772 (Sep. 16, 2005).
Bowles, J. A., et al., "CD16 polymorphisms and NK activation induced by monoclonal antibody-coated target cells," *Journal of Immunological Methods*, (2005) Issues 1-2, vol. 304, pp. 88-99.
Brekke, O. H., et al., "Human IgG isotype-specific amino acid residues affecting complement-mediated cell lysis and phogocytosis," *Eur. J. Immunl.*, 24(10):2542-5247 (Oct. 1994).
Brekke, O. H., et al., "Human IgG3 can adopt the disulfide bond pattern characteristic for IgG1 without resembling it in complement mediated cell lysis," *Mol. Immunol.* 30(16):1419-1425 (Nov. 1993).
Bruggeman, M., et al., "Comparison of the Effector Functions of Human Immunoglobulins Using a Matched Set of Chimeric Antibodies," *J. Exp. Med.*, 166:1351-1361 (Nov. 1987).
Bruggemann, M., et al., "A matched set of rat/mouse chimeric antibodies. Identification and biological properties of rat H chain constant regions mu, gamma 1, gamma 2a, gamma 2b, gamma 2c, epsilon, and alpha," *J. Immunol.*, 142(9):3145-3150 (May 1989).
Burmeister, W. P., et al., "Crystal structure of the complex of rat neonatal Fc receptor with Fc" *Nature*, 372:379-383 (Nov. 24, 1994).

Burton, et al. "Immunoglobulin G: Functional sites", *Molecular Immunology*, vol. 22, No. 3, (Mar. 1985).
Canfield, S. M., et al., "The Binding Affinity of Human IgG for its High Affinity Fc Receptor is Determined by Multiple Amino Acids in the $C_H2$ Domain and Is Modulated by the Hinge Region," *J. Exp. Med.*, 173:1483-1491 (Jun. 1991).
Caron, P. C., et al., "Engineered Humanized Dimeric Forms of IgG Are More Effective Antibodies," *J. Exp. Med.*, 176:1191-1195 (Oct. 1992).
Caron, P. C., et al., "Murine and humanized constructs of monoclonal antibody M19 (anti-CD33) for the therapy of acute myelogenous leukemia," *Cancer*, 73(3 Supp):1049-1056 (Feb. 1994).
Carpenter, P.A., et al., "Non-Fc Receptor-Binding Humanized Anti-CD3 Antibodies Induce Apoptosis of Activated Human T Cells," *Journal of Immunology*, 165:6205-6213 (2000).
Carter, P., "Improving the Efficacy of Antibody-Based Cancer Therapies," *Nature Reviews*, 1:118-129 (2001).
Carter, P., et al., "Humanization of an anti-p185$^{HER2}$ antibody for human cancer therapy" *PNAS*, 89:4285-4289 (May 1992).
Cartron, G., et al., "Therapeutic activity of humanized anit-Cd20 monoclonal antibody and polymorphism in IgG Fc receptor Fcγ RIIIa gene," *Blood*, 99(3):754-758 (Feb. 1, 2002).
Chadd, H., et al., "Therapeutic antibody expression technology," *Curr. Opin. Biotech.*, 12:188-194 (2001).
Chamow, et al., "Immunoadhesins: principles and applications," *Trends Biotechnol*, 14:52-60 (1996).
Chan, et al. "Variable Region Domain Exchange in Human IgGs promotes antibody complex formation with accompanying structural changes and altered effector functions" *Molecular Immunology* 2004, 21:527-538.
Chapman, P. B., "T-Cell Chauvinists Versus Antibody Advocates—Can't We All Just Get Along?" *J. Clin. Oncology*, 22(22):4446-4448 (Nov. 15, 2004).
Chappel, M. S., et al., "Identification of a Secondary Fcγ RI Binding Site within a Genetically Engineered Human IgG Actibody," *J. Biol. Chem.*, 268(33):25124-25131 (Nov. 1993).
Chappel, M. S., et al., "Identification of the Fcγ receptor class I binding site in human IgG through the use of recombinant IgG1/IgG2 hybrid and point-mutated antibodies," *PNAS, USA*, 88:9036-9040 (Oct. 1991).
Chintalacharuvu, K. R., et al., "Hybrid IgA2/IgG1 Antibodies with Tailor-Made Effector Functions," *Clinical Immunology*, 101(1):21-31—(Oct. 2001).
Chirino, A.J. et al."Minimizing the immunogenicity of protein therapeutics", *Drug Discovery Today*, 2004, vol. 9, No. 2, pp. 82-90.
Clark, M. "Antibody humanization: a case of the 'Emperor's new clothes?'" *Immunol. Today*, 21(8):397-402 (2000).
Clark, M. R., "Chemical Immunology Antibody Engineering IgG Effector Mechanisms," Dissertation submitted to Immunology Division of Department of Pathology at Cambridge University, UK *J. Chem. Immunol.* 1997, vol. 65, pp. 88-110.
Clynes, R. A., et al., "Inhibitory Fc receptors modulate in vivo cytoxicity against tumor targets," *Nature Medicine*, 6(4):443-446 (Apr. 2000).
Clynes, R. et al., "Modulation of Immune complex-induced Inflammation In Vivo by the Coordinate Expression of Activation and Inhibitory Fc Receptors," *J. Exp. Med.*, 189(1):179-185 (Jan. 4, 1999).
Clynes, R., "Immune complexes as therapy for autoimmunity" *J. Clin. Invest.*, 115:25-27 (2005).
Clynes, R., et al., "Fc receptors are required in passive and active immunity to melanoma," *PNAS USA*, 95:652-656 (Jan. 1998).
Cohen-Sodal, J. FG., et al., "Review: Fc γ receptors" *Immunology Letts*, 92:199-205 (2004).
Cole, M. S., et al., "Human IgG2 variants of chimeric anti-CD3 are nonmitogenic to T cells," *J. Immunol.*, 159(7):3613-3621 (Oct. 1, 1997).
Cole, M.S., et al., "HUM291, a Humanized Anti-CD3 Antibody, is immunosuppressive to T cells while exhibiting reduced mitogenicity in vitro", *Transplantation*, vol. 68, No. 4, pp. 563-571 (1999).
Coloma, M. J., et al., "The hinge as a spacer contributes to convalent assembly and is required for function of IgG," *J. Immunol.*, 158(2):733-740 (Jan. 15, 1997).

(56) References Cited

OTHER PUBLICATIONS

Cragg, M., et al., "Signaling antibodies in cancer therapy," *Curr. Opin. Immunol.*, 11:541-547 (1999).
D'Uscio, C. H., et al., "Cellular cytotoxicity mediated by isotype-switch variants of a monoclonal antibody to human neuroblastoma," *Br. J. Cancer*, 64(3):445-450 (Sep. 1991).
Da Silveira, S. A., et al., "Complement Activation Selectively Potentiates the Pathogenicity of the IgG2 b and IgG3 Isotypes of a High Affinity Anti-Erythrocyte Autoantibody," *J. Exp. Med.*, 195(6):665-672 (Mar. 18, 2002).
Dahiyat, B. I. et al. "Protein Design Automation", *Protein Science*, 1996, vol. 5, No. 5, ps. 895-903.
Dall'Acqua, D. F., et al., "Increasing the Affinity of a Human IgG1 for the Neonatal Fc Receptor: Biological Consequences," *Journal of Immunology*, 169:5171-5180 (2002).
Dall'Acqua, W. et al. "Modulation of the Effector Functions of a Human IgG1 through Engineering of Its Hinge Region", 2006, *J. Immunology*, 177:1129-1138.
Dall'Acqua, W., et al., "Antibody Engineering," *Curr. Opin Structural Biol.*, 8:443-450 (1998).
Davies, et al. "Expression of GnTIII in a recombinant anti-CD20 CHO production cell line: Expression of antibodies with altered glycoforms leads to an increase in ADCC through higher affinity for FC gamma RIII," *Biotechnol Bioeng*, 74:288-294 (2001).
Davis, R. S., et al., "Fc receptor homologs: newest members of a remarkably diverse Fc receptor gene family," *Imm. Revs*, 190:123-136 (2002).
Davis, R. S., et al., "Identification of a family of Fc receptor homologs with preferential B cell expression," *PNAS, USA*, 98(17):9772-9777 (Aug. 2001).
Delano, W. L., et al., "Convergent Solutions to Binding at a Protein-Protein Interface" *Science*, 287:1279-1283 (Feb. 18, 2000).
Dhodapkar, K.M., et al., "Antitumor Monoclonal Antibodies Enhance Cross-Presentation of Cellular Antigens and the Generation of Myeloma-specific Killer T-Cells by Dendritic Cells" *J. Exp Med.*, 195(1):125-133 (Jan. 7, 2002).
Dhodapkar, K.M., et al., "Recruiting dendritic cells to improve antibody therapy of cancer" *PNAS*, 102(18):6243-6244 (May 3, 2005).
Dhodapkar, K.M., et al., "Selective blockade of inhibitory Fc γ receptor enables human dendritic cell maturation with IL-12p70 production and immunity to antibody-coated tumor cells" *PNAS*, 102(8):2910-2915 (Feb. 22, 2005).
Dhodapkar, M. V., et al., "T cells from the tumor microenvironment of patients with progressive myeloma can generate strong, tumor-specific cytolytic responses to autologous, tumor-loaded dendritic cells" *PNAS*, 99(20):13009-13013 (Oct. 1, 2002).
Duncan, A. R., et al., "Localization of the binding site for the human high-affinity Fc receptor on IgG," *Nature*, 332:563-564 (Apr. 7, 1988).
Duncan, A. R., et al., "The binding site for C1q on IgG," *Nature* 332:738-740 (Apr. 21, 1988).
Edelman, G. M., et al., "The Covalent Structure of an Entire γG Immunoglobulin Molecule," *PNAS*, 63:78-85 (1969).
Ehrhardt, G. R. A., et al., "Th inhibitory potential of Fc receptor homolog 4 on memory B cells," *PNAS, USA*, 100(23):13489-13494 (Nov. 2003).
Ellison, J. W., et al., "The nucleotide sequence of a human immunoglobulin Cγ$_1$ gene" *Nucleic Acids Research*, 10(13):4071-4079(1982).
Ernst, L. K., et al., "Molecular characterization of six variant Fc γ receptor class I (CD64) transcripts," *Molecular Immunology*, 35:943-954 (1998).
Facchetti, F., et al., "An unusual Fc receptor-related protein expressed in human centroblasts," *PNAS, USA*, 99(6):3776-3781 (Mar. 19, 2002).
Gaboriaud, C., et al., "The Crystal Structure of the Globular Head of Complement Protein C1q Provides a Basis for Its Versatile Recognition Properties," *J. Biol. Chem.*, 278(47):46974-46982 (2003).

Garman, S. C., et al., "Structure of the Fc fragment of human IgG bound to its high-affinity receptor FcϵRIα," *Nature*, 406:259-266 (2000).
Getahun, A., et al., "IgG2a-Mediated Enhancement of Antibody and T Cell Responses and Its Relation to Inhibitory and Activating Fc γ Receptors," *J. of Immunology*, 172:5269-5276 (2004).
Ghazizadeh, S., et al., "Physical and Functional Association of Src-related Protein Tyrosine Kinases with FcRII in Monocytic THP-1 Cells," *J. Biol. Chem.*, 269(12):8878-8884 (Mar. 25, 1994).
Ghetie, V., et al., "FcRn: the MHC class I-related receptor that is more than an IgG transporter" *Immunology Today*, 18(12):592-598 (Dec. 1997).
Ghetie, V., et al., "Increasing the serum persistence of an IgG fragment random mutagenesis," *Nat. Biotechol.*, 15(7):637-640 (Jul. 1997).
Ghetie, V., et al., "Multiple Roles for the Major Histocompatibility Complex Class I-Related Receptor FcRn," *Annu. Rev. Immunol.* 18:739-766 (2000).
Glennie, M., et al., "Clinical trials of antibody therapy," *Immun. Today*, 21(8):403-410 (2000).
Glennie, M., et al., "Renaissance of cancer therapeutic antibodies," *Drug Discovery Today*, 8(11):503-510 (2003).
Gonzales, N. R., et al., "SDR grafting of a murine antibody using multiple human germline templates to minimize its immunogenicity," *Molecular Immunology*, 41:863-872 (2004).
Greenwood, J. "Molecular Recognition in the Structure and Assembly of Filamentous Bacteriophages," Dissertation submitted to the University of Cambridge (Oct. 1989) pp. 1-251.
Greenwood, J., et al., "Structural motifs involved in human IgG antibody effector functions," *Eur. J. Immunol.*, 23(5):1098-1104 (May 1993).
Greenwood, J., et al., "Dual Importance of Positive Charge in the C-Terminal Region of Filamentous Bacteriophage Coat Protein for Membrane Insertion and DNA-Protein Interaction in Virus Assembly," *Virology*, 171:444-452 (1989).
Greenwood, J., et al., "Effector functions of matched sets of recombinant human IgG subclass antibodies," Dissertation submitted to Cambridge University, Cambridge, UK (Feb. 1993) (final version edited Feb. 11, 1993) pp. 1-23.
Greenwood, J., et al., "Engineering multiple-domain forms of the therapeutic antibody CAMPATH-1H: effects on complement lysis," *Ther Immunol.*, 1(5):247-255 (Oct. 1994).
Groh, V., et al., "Efficient cross-priming of tumor antigen specific T cells by dendritic cells sensitized with diverse anti-MICA opsonized tumor cells" *PNAS*, 102(18):6461-6466 (May 3, 2005).
Harrison, P. T., et al., "Domain swap chimeras to study the binding of IgG by Fc gamm RI, the high affinity receptor for IgG," *Biochem Soc Trans.*, 24(1):1445 (Feb. 1996).
Hayes R.J. et al. "Combining computational and experimental screening for rapid optimization of protein properties", *PNAS*, 2002, vol. 99,.No. 25, pp. 15926-15931.
Hayhurst, A., et al., "High-throughput antibody isolation," *Curr. Opin. Chem. Biol.*, 5:683-689 (2001).
Hazenbos, W.L., et al., "Murine IgG1 complexes Trigger Immune Effector Functions Predominately via Fcγ RIII (CD16)," *J. of Immunology*, 161:3026-3032 (1998).
Henry, A. J., et al., "Participation of the N-Terminal of CE3 in the Binding of Human IgE to Its High-Affinity Receptor FcϵRI," *Biochemistry*, 36:15568-15578 (1997).
Hezareh, M., et al., "Effector Function Activities of a Panel of Mutants of a Broadly Neutralizing Antibody against Human Immunodeficiency Virus Type I," *Journal of Virology*, 75(24):12161-12168 (2001).
Hinton, P. R., et al., "Engineered human IgG Antibodies with Longer Serum Half-Lives Lives in Primates," *J. Biol Chem.*, 279(8):6213-6216 (Feb. 20, 2004).
Hogarth, P., "Fc receptors are major mediators of antibody based inflammation in autoimmunity," *Curr. Opin. Immun.*, 14:798-802 (2002).
Holliger, P., et al., "Antibodies come back from the brink," *Nature Biotechnology*, 16:1015-1016 (1998).

(56) References Cited

OTHER PUBLICATIONS

Hudson, P., "Recombinant antibody constructs in cancer therapy," *Curr. Opin. Immunology*, 11:548-557 (1999).
Hudson, P., "Recombinant antibody fragments," *Curr. Opin in Biotechnology*, 9:395-402 (1998).
Hutchins, et al., "Improved biodistribution, tumor targeting, and reduced immunogenicity in mice with a gamma 4 variant of Campath-1H," *PNAS USA*, 92:11980-11984 (1995).
Idusogie, E. E., et al., "Engineered Antibodies with Increased Activity to Recruit Complement," *J. of Immunology*, 166:2571-2575 (2001).
Idusogie, E.E., et al., "Mapping of the C1q Binding Site on Rituxan, a Chimeric Antibody with a Human IgG1 Fc," *J. of Immunology*, 164:4178-4184 (2000).
Isaacs, J. D., "Improving Serotherapy with Monoclonal Antibodies" dissertation submitted to the University of Cambridge (Mar. 1991) pp. 1-209.
Isaacs, J. D., et al., "From bench to bedside: discovering rules for antibody design, and improving serotherapy with monoclonal antibodies," *Rheumatology*, 40:724-738 (2001).
Issacs, J. D., et al., "Therapy with Monoclonal Antibodies, II. The contribution of Fcγ Receptor binding and the Influenece of $C_H1$ and $C_H3$ Domains on In Vivo Effector Function," *J. of Immunology*, 161:3862-3869 (1998).
Issacs, J. D., et al., "Therapy with Monoclonal Antibodies: an in vivo model for the assessment of therapeutic potential," *J. Immunol.*, 148(10):3062-3071 (May 15, 1992).
Jefferies, et al., "Modulation of Fcγ R and Human Complement Activation by IgG3-core oligosaccharide interractions" *Immunol Lett*, 54:101-104 (1996).
Jefferis, R. et al., "Recognition sites on human IgG for Fc gamma receptors: the role of glycosylatin," *Immunol Letters*, 44(2-3):111-117 (Jan. 1995).
Jefferis, R., et al., "Interaction sites on human IgG-Fc for FcγR: current models," *Immunology Letts.*, 82:57-65 (2002).
Jefferis, R., et al., "Modulation of FcγR and human complement activation by IgG3-core oligosaccharide interactions," *Immunology Letters*, 54:101-104 (1996) and errata at *Immunology Letters*, 58:67 (1997).
Jefferis, R., et al., "Molecular definition of interaction sites on human IgG for Fc receptors (huFc gamma R)," *Mol Immunol.*, 27(12):1237-1240 (Dec. 1990).
Jendeberg, L., et al., "Engineering of $Fc_1$ and $Fc_3$ from human immunoglobulin G to analyse subclass specificity for staphylococcal protein A," *Journal of Immunological Methods*, 201:25-34 (1997).
Johnson, G., et al., "Kabat Database and its applications: 30 years after the first variability plot," *Nucleic Acids Research*, 28(1):214-218 (2000).
Johnson, G., et al., "Kabat Database and its applications: future directions," *Nucleic Acids Research*, 29(1):205-206 (2001).
Junghans, R. P., et al., "The protection receptor for IgG catabolism is the $\beta_2$-microglobulin-containing neonatal intestinal transport receptor," *PNAS*, 93:5512-5516 (May 1996).
Kabat et al., NIH Pub. No. 91-3242, p. 679-687 (1991).
Kalergis, A.M., et al., "Inducing Tumor Immunity through the Selective Engagement of Activating Fcγ Receptors on Dendritic Cells" *J. Exp. Med.* 195(12):1653-1659 (Jun. 17, 2002).
Kan, K. S., et al., "Thioether-Bonded Constructs of Fab'γ and Fcγ Modules Utilizing Differential Reduction of Interchain Disulfide Bonds," *Journal of Immunology*, 166:1320-1326 (2001).
Karassa, F. B., et al., "The role of FcγRIIA and IIIA polymorphisms in autoimmune diseases," *Biomedicine & Pharmacotherapy*, 58:286-291 (2004).
Kato, K. et al., "Analysis of IgG-FcgammaR interactions in solution: Mapping of the FcgammaR binding site and evidence for a conformational change occurring in the Fc region", *Immunology Letters*, vol. 73, No. 2-3 (2000).
Kim, J. et al., "Mapping the site on human IgG for binding of the MHC class I-related receptor, FcRn" *Eur. J. Immunol.*, 29:2819-2825 (1999).

Kim, J. K., et al., "Localization of the site of the murine IgG1 molecule that is involved in binding to the murine intestinal Fc receptor," *Eur J Immunol.*, 24(10):2429-2439 (Oct. 1994).
Kim, J.K., et al., "Identifying amino acid residues that influence plasma clearance of murine IgG1 fragments by site-directed mutagenesis," *Eur J. Immunol.*, 24(3):542-548 (Mar. 1994).
Kim, T. D., et al., "Analysis of FcγRIII and IgG Fc Polymorphism Reveals Functional and Evolutionary Implications of Protein-Protein Interaction," *J. Mol. Evol.*, 53:1-9 (2001).
Krapp, et al., "Structural analysis of human IgG-Fc glycoforms reveals a correlation between glycosylation and structural integrity," *J Mol Biol*, 325:979-989 (2003).
Kurucz, I., et al., "Bacterially expressed human FcγRIIb is soluble and functionally active after in vitro refolding" *Immunology Letts.*, 75:33-40 (2000).
Lazar, et al. "Engineered antibody Fc variants with enhanced effector function" PNAS, 2006, 4005-4010.
Lehrnbecher, et al., "Variant Genotypes of the Low-Affinity Fcγ Receptors in Two Control Populations and a Review of Low-Affinity Fcγ Receptor Polymorphisms in Control and Disease Populations," *Blood*, 94:4220-4232 (1999).
Liu, et al. "Production of a Mouse-Human Chimeric Monoclonal Antibody to CD20 with Potent Fc-Dependent Biologic Activity" *The Journal of Immunology*, 1998, 139-10:3521-3526.
Lund, et al., "Human Fc gamma RI and Fc gamma RII interact with distinct but overlapping sites on human IgG," *J Immunol*, 147:2657-2662 (1991).
Lund, et al., "Multiple binding sites on the CH2 domain of IgG for mouse Fc gamma R11," *Mol Immunol*, 29:53-59 (1992).
Lund, et al., "Multiple interactions of IgG with its core oligosaccharide can modulate recognition by complement and human Fc gamma receptor I and influence the synthesis of its oligosaccharide chains," *J Immunol*, 154:4963-4969 (1996).
Lund, et al., "Oligosaccharide-protein interactions in IgG can modulate recognition by Fc gamma receptors," *Faseb J*, 9:115-119 (1995).
Lund, J., et al., "A protein structural change in aglycosylated IgG3 correlates with loss of huFc gamma R1 and huFc gamma R111 binding and/or activation," *Mol. Immunol.*, 27(11):1145-1153 (Nov. 1990).
Lund, J., et al., "Control of IgG/Fc glycosylation: a comparision of oligosaccharides from chimeric human/mouse and mouse subclass immunoglobulin Gs," *Mol Immunol.*, 30(8):741-748 (Jun. 1993).
Maenaka, K., et al., "The Human Low Affinity FcγReceptors IIa, IIb and III Bind IgG with Fast Kinetics and Distinct Thermodynamic Properties" *J. Biol. Chem.*276(48):44898-44904 (2001).
Martin, W. L., et al., "Characterization of the 2:1 Complex between the Class I MHC-Related Fc Receptor and Its Fc Ligand in Solution," *Biochemistry*, 38:12639-12647 (1999).
Martin, W. L., et al., "Crystal Structure at 2.8 Å of an FcRn/Heterodimeric Fc Complex: Mechanism of pH-Dependent Binding" *Molecular Cell*, 7:867-877 (Apr. 2000).
Masztalerz, A., et al., "Mechanisms of macrophage cytotoxicity in IL-2 and IL-12 mediated tumor regression," *Cancer Immunol Immunother*, 52:235-242 (2003).
Maxwell, K.F., et al., "Crystal structure of the human leukocyte Fc receptor, FcRIIa." *Nature Structural Biology*, 6(5):437-442 (May 1999).
Mayfield, S. P., et al., "Expression and assembly of a fully active antibody algae," *PNAS*, 100(2):438-442 (Jan. 21, 2003).
Maynard, J., et al., "Antibody Engineering," *Annu. Rev. Biomed. Eng.*, 2:339-376 (2000).
Mechetina, L. V., et al., "Identification of CD16-2, a novel mouse receptor homologous to CD16/FcγRIII," *Immunogenetics*, 4:463-468 (2002).
Medesan, et al. "Comparative studies of rat IgG to further delineate the Fc:FcRn interaction site" *Eur.J. Immunol.* (1998) 28:2092-2100.
Merchant, A. M. et al., "An efficient route to human bispecific IgG," *Nat Biotechnol.*, 16(7):677-681 (1998).
Metes. D., et al., "Expression of Functional CD32 Molecules on Human NK Cells Is Determined by and Allelic Polymorphism of the FcγRIIC Gene," *Blood*, 91(7):2369-2380 (Apr. 1, 1998).

(56) References Cited

OTHER PUBLICATIONS

Michaelson, T. E., et al., "Antibody Dependent Cell-Mediated Cytotoxicity Induced by Chimeric Mouse-Human IgG Subclass and IgG3 Antibodies with Altered Hinge Region," *Molecular Immunology*, 29(3):319-326 (1992).
Michaelson, T. E., et al., "One disulfide bond in front of the second heavy chain constant region is necessary and sufficient for effector functions of human IgG3 without a genetic hinge," *PNAS*, 91:9243-9247 (Sep. 1994).
Michaelson, T. E., et al., "Primary Structure of the 'Hinge' Region of Human IgG3," *J Biol Chem.*, 252(3):883-889 (Feb. 1977).
Miller, I., et al., "ITRAs: a new family of immunoglobulinlike receptors differentially expressed in B cells," *Blood*, 99(8):2662-2669 (Apr. 15, 2002).
Mimura, Y., et al., "Role of Oligosaccharide Residues of IgG1-Fc in Fc$\gamma$ RIIb Binding," *J. Biol. Chem.*, 276(49):45539-45547 (Dec. 7, 2001).
Morea, V., et al., "Antibody Modeling: Implications for Engineering and Design," *Methods*, 20:267-279 (2000).
Morgan, A., et al., "The N-terminal end of the CH2 domain of chimeric human IgG1 anti-HLA-DR is necessary for C1q, Fc gamma R1 and Fc gamma RIII binding," *Immunology*, 86(2):319-324 (Oct. 1995).
Morrison, et al. "Variable Region Domain Exchange Influences the Functional Properties of IgG$^1$" *The Journal of Immunology* 1998, 160:2802-2808.
Nakamura, K., et al., "Dissection and optimization of immune effector functions of humanized anti-ganglioside GM2 monoclonal antibody," *Molecular Immunology*, 37:1035-1046 (2000).
Natsume, A. et al. "Engineered Antibodies of IgG1/IgG3 Mixed Isotype with Enhanced Cytotoxic Activities", 2008, *Cancer Research*, 68:(10) pp. 3863-3871.
Neidhardt-Berard, E., et al., "Dendritic cells loaded with killed breast cells induce differentiation of tumor-specific cytoxic T lymphocytes" *Breast Cancer Res.*, 6R322-R328 (Apr. 30, 2004).
Nimmerjahn, F., et al., "Divergent Immunoglobulin-G Subclass Activity Through Selective Fc Receptor Binding" *Science*, 310:1510 (2005).
Nimmerjahn, F., et al., "Fc$\gamma$ RIV: A Novel FcR with Distinct IgG Subclass Specificity," *Immunity*, 23:41-51 (Jul. 2005).
Nimmerjahn, F., et al., "Supporting Online Material for: Divergent Immunoglobulin G Subclass Activity Through Selective Fc Receptor Binding" *Science*, 310:1510 (2005).
Niwa, R., et al., "Defucosylated Chimeric Anti-CC Chemokine Receptor 4 IgG1 with Enhanced Antibody-Dependnent Cellular cytotoxicity Shows Potent Therapeutic Activity to T-Cell Leukemia and Lymphoma," *Cancer Research*, 64:2127-2133 (Mar. 15, 2004).
Norderhaug, L., et al., "Chimeric mouse human IgG3 antibodies with an IgG4-like hinge region induce complement-mediated lysis more efficiently than IgG3 with normal hinge," *Eur J immunol.*, 21(10):2379-2384 (Oct. 1991).
O'Connor, S. J., et al., "Humanization of an antibody against human protein C and calcium-dependence involving framework residues," *Protein Engineering*, 11(4):321-328 (1998).
Ober, R. J., et al., "Differences in promiscuity for antibody-FcRn interactions across species: implications for therapeutic antibodies," *International Immunology*, 13(12):1551-1559 (2001).
Ober, R. J., et al., "Exocytosis of IgG as mediated by the receptor, FcRn: An analysis at the single-molecule level" *PNAS*, 101(30):11076-11081 (Jul. 27, 2004).
Okazaki, A., et al., "Fucose Depletion from Human IgG1 Oligosaccharide Enhances Binding Enthalpy and Association Rate Between IgG1 and Fc$\gamma$ RIIIa," *J. Mol. Biol.*, 336:1239-1249 (2004).
Parren, P. W., et al., "Characterization of IgG FcR-mediated proliferation of human T-cells induced by mouse and human anti-CD3 monoclonal antibodies. Identification of a functional polymorphism to human IgG2 anti-CD3," *J. Immunol.*, 148(3):695-701 (Feb. 1992).
Parren, P. W., et al., "On the interaction of IgG subclasses with the low affinity Fc gamma RIIa (CD32) on human monocytes, neutrophils, and platelets. Analysis of a functional polymorphism to human IgG2," *J Clin Invest.*, 90(4):1537-1546 (Oct. 1992).
Pearce, K. H., et al., "Mutational Analysis of Thrombopoietin for Identification of Receptor and Neutralizing Antibody Sites," *J. Biol. Chem.*, 272(33):20595-20602 (1997).
Pendley C. et al., "Immunogencity of therapeutic monoclonal antibodies", *Current Opinion in Molecular Therapeutics*, 2003, vol. 5, No. 2, pp. 172-179.
Penichet, M., et al., "Antibody-cytokine fusion proteins for the therapy of cancer," *Journal of Immunological Methods*, 248:91-1010 (2001).
Preithner, S., et al., "High concentrations of therapeutic Igg1 antibodies are needed to compensate for inhibition of antibody-dependnent cellular cytotoxicity by excess endogenous immunoglobulin G," *Molecular Immunology*, (2005).
Presta, L.G., et al., "Engineering therapeutic antibodies for improved function," *Biochemical Society Transactions*, 30(part 4):487-490 (2002).
Radaev, S., et al., "Recognition of IgG by Fc$\gamma$ Receptor," *J. Biol. Chem.*, 276(19):16478-16483 (May 11, 2001).
Radaev, S., et al., "Review: Recognition of immunoglobulins by Fc$\gamma$ recptors," *Molecular Immunology*, 38:1073-1083 (2001).
Radaev, S., et al., "The Structure of Human Type III Fc$\gamma$ Receptor in Complex with Fc," *J. Biol. Chem.*, 276(19):16469-16477 (May 11, 2001).
Rafiq, K., et al., "Immune complex-mediated antigen presentation induces tumor immunity" *J. Clin. Invest.* 110:71-79 (2002).
Raghavan, M., et al., "Fc Receptors and Their Interactions with Immunoglobulins" *Annu. Rev. Cell Div. Biol.*, 12:181-220 (1996).
Ravetch, J. V., et al., "IgG Fc Receptors" *Annu. Rev. Immunol.*, 19:275-290 (2001).
Ravetch, J. V., et al., "Immune Inhibitory Receptors," *Science*, 290:84-89 (Oct. 6, 2000).
Ravetch, J.V., et al., "Fc Receptors," *Annu. Rev. Immunol.*, 9:457-492 (1991).
Reddy, P. R., et al., "Elimination of Fc Receptor-Dependent Effector Functions of a Modified IgG4 Monoclonal Antibody to Human CD4" *J. Immunol.*, 164:1925-1933 (2000).
Redpath, S., et al., "The Influence of the Hinge Region Length in Binding of Human IgGto Human Fc$\gamma$ Receptors," *Human Immunology*, 59:720-727 (1998).
Reichert, J., "Monoclonal antibodies in the clinic," *Nature Biotechnology*, 19:819-822 (2001).
Rozsnyay, Z., et al., "Distinctive role of IgG1 and IgG3 isotypes in FcR-mediated functions," *Immunology*, 66(4):491-498 (Apr. 1989).
Sandlie, A.A., "The extended hinge region of IgG3 is not required for high phogocytic capacity mediated by Fc gamma receptors, but the heavy chains must be disulfide bonded," *Eur J. Immunol.* 23(7):1546-1551 (Jul. 1993).
Sarmay, G., et al., "Mapping and Comparison of the Interaction Sites on the Fc Region of IgG Responsible for Triggering Antibody Dependent Cellular Cytotoxicity (ADCC) Through Different Types of Human FC$\gamma$ Receptor," *Molecular Immunology*, 29(5):633-639 (1992).
Sautes-Fridman, C., et al., "Fc Gamma Receptors: A Magic Link with the Outside World," *ASHI Quarterly*, 148-151, (Fourth Quarter 2003).
Sensel, M. G., et al., "Amino Acid Differences in the N-Teminus of $C_H2$ Influence the Relative abilities of IgG2 and IgG3 to Activate Complement" *Mol. Immunol.*, 34(14):1019-1029 (1997).
Shields, R. L., et al., "High Resolution Mapping of the Binding Site on Human IgG1 for Fc$\gamma$ RI, Fc$\gamma$ RII, Fc$\gamma$ RIII, and FcRn and Design of IgG1 Varients with Improved Binding to the Fc$\gamma$ R" *J. Biol. Chem.*, 276(9):6591-6604 (2001).
Shields, R. L., et al., "Lack of Fucose on human IgG1 N-Linked Oligodaccharide Improves Binding to Human Fc$\gamma$ RIII and Antibody-dependent Cellular Toxicity" *J. Biol. Chem.*, 277(30)26733-26740 (2002).
Shinkawa, T., et al., "The Absence of Fucose but Not the Presence of Galactose or Bisecting N-Acetylglucosamine of Human IgG1 com-

(56) References Cited

OTHER PUBLICATIONS plex-type Oligosaccharides Shows the Critical Role of Enhancing Antibody-dependent Cellular Cytotoxicity" *J. Biol. Chem.*, 278(5):3466-3473 (2003).

Shitara et al. "A new vector for the high level expression of chimeric antibodies in myeloma cells" *J. of Immunological Methods*, 1994, 167: 271-278.

Shopes, B., "A genetically engineered human IgG mutant with enhanced cytolytic activity," *J Immunol.*, 148(9):2918-2922 (May 1992).

Shopes, B., et al., "Recombinant human IgG1-murine IgE chimeric Ig. Construction, expression, and binding to human Fc gamma receptors," *J. Immunol.*, 145(11):3842-3848 (Dec. 1, 1990).

Simmons, L. C., et al., "Expression of full-length immunoglobulins in *Escherichia coli*; rapid and efficient production of a glycosylated antibodies" *J. Immunol. Methods*, 263:133-147 (2002).

Smith, I. F. R., et al., "Addition of a μ-Tailpiece to IgG Results in Polymeric Antibodies with Enhanced Effector Functions Including Complement-Mediated Cytolysis by IgG4," *J. Immunology*, pp. 2226-2236 (1995).

Smith, K.G., et al., "T cell activation by anti-T3 antibodies: comparison of IgG1 and IgG2b switch variants and direct evidence for accessory function of macrophage Fc receptors," *Eur J Immunol.*, 16(5):478-486 (May 1986).

Sondermann, P. et al., "Crystal structure of the soluble form of the human FCγ-receptor IIb: a new member of the immunoglobulin superfamily at 1.7Å resolution" *EMBO Journal*, 18(5):1095-1103 (1999).

Sondermann, P., et al., "Human Fcγ Receptor IIb Expressed in *Escherichia coli* Reveals IgG Binding Capability" *Biol. Chem.* 380:717-721 (Jun. 1999).

Sondermann, P., et al., "Molecular Basis for Immune Complex Recognition: A comparison of Fc-Receptor Structures" *J. Mol. Biol.*, 309:737-749 (2001).

Sondermann, P., et al., "The 3.2-Å crystal structure of the human IgG1 Fc fragment-Fcγ RIII complex" *Nature*, 406:267-273 (Jul. 20, 2000).

Sorenson, V., et al., "Effect of the IgM and IgA secretory tailpieces on polymerization and secretion of IgM and IgG," *J Immunol.*, 156(8):2858-2865 (Apr. 1996).

Steplewski, Z., et al., "Biological activity of human-mouse IgG1, IgG2, IgG3, and IgG4 chimeric monoclonal antibodies with antitumor specificity," *PNAS USA*, 85:4852-4856 (Jul. 1988).

Stevenson, G. T., et al., "Preparation of Fcγ for addition to sulfhydryl-expressing ligands with minimal disturbance of the hinge," *J. of Immunological Methods*, 231:169-175 (1999).

Tamm, A. et al., "IgG Binding Sites on Human Fcγ Receptors" 1997, *International Reviews of Immunology*, 16:1,57-85.

Tao, M., et al., "Structural Features of Human immunoglobulin G that Determine Isotype-specific Differences in Complement Activation," *J. Exp. Med.* 178:661-667 (Aug. 1993).

Tao, M., et al., "The Differential Ability of Human IgG1 and IgG4 to Activate Complement Is Determined by the COOH-terminal Sequence of the $C_H2$ domain" *J. Exp. Med*, 173:1025-1028 (Apr. 1991).

Thommesen, J. E., et al., "Lysine 322 in the human IgG3 $C_H2$ domain is crucial for antibody dependent complement activation" *Molecular Immunology*, 37:995-1014 (2000).

Thrush, G., et al., "Immunotoxins: An Update," *Ann. Rev. Immunol.*, 14:49-71 (1996).

Torphy, T., et al., "Pharmaceutical biotechnology Monoclonal antibodies: boundless potential, daunting challenges—Editorial Overview," *Curr. Opin. Biotechnol.*, 13:589-591 (2002).

Trail, P., et al., "Monoclonal antibody drug conjugates in the treatment of cancer" *Curr. Opin. Immunol.*, 11:584-588 (1999).

Trikha, M., "Monoclonal antibodies as therapeutics in oncology," *Curr. Opin. Biotech.*, 13:609-614 (2002).

Tuijnman W. B., et al., "A flow cytometric rosetting assay for the analysis of IgG-Fc receptor interactions," *J Immunol Methods*, 127(2):207-214 (Mar. 1990).

Uchide, J. et al., "The Innate Mononuclear Phagocyte Network Depletes B Lymphocytes through Fc Receptor-dependent mechanisms during Anti-CD20 Antibody Immunotherapy" *J. Exp. Med.* 199(12):1659-1669 (Jun. 21, 2004).

Umana, P., et al., "Engineered glycoforms of an antineuroblastoma IgG1 with optimized antibody-dependent cellular cytotoxic activity," *Nature Biotechnology*, 17:176-180 (1999).

Valerius, T. et al., "Fcalpha RI (CD89) as a Novel Trigger Molecule for Bispecific Antibody Therapy" *Blood*, 1997, 90:4485-4492.

Van Dijk, M., et al., "Human antibodies as next generation therapeutics," *Curr Opin. Chem. Biol.*, 5:368-374 (2001).

Van Royen-Kerkhof, A, et al., "Flow cytometric determination of Fc γ RIIa (CD32) polymorphism," *J. Immunol. Methods*, 294:135-144 (2004).

Van Schie, R.C.A.A., et al., "Evaluation of Human Fcγ RIIA (CD32) and Fcγ RIIIB (CD16) Polymorphisms in Caucasians and African-Americans Using Salivary DNA," *Clinical and Diagnostic Laboratory Immunology*, 7(4):676-681 (Jul. 2000).

Van Sorge, N., et al., "Fcγ R polymorphisms: Implications for function, disease susceptibility and immunotherapy," *Tissue Antigens*, 61:189-202 (2003).

Vasserot, A., et al., "Optimization of protein therapeutics by directed evolution," *Drug Discovery Today*, 8(3):118-126 (2003).

Vidarte, L., et al., "Serine 132 Is the C3 Covalent Attachment Point of the CH1 domain of Human IgG1" *J. Biol. Chem.*, 276(41):38217-38223 (2001).

Vitetta, E., et al., "Considering Therapeutic Antibodies", *Science*, 2006, vol. 313, pp. 308-309.

Waldmann, T., et al., "Emerging Therapies: Spectrum of Application of Monoclonal Antibody Therapy," *Hemotology*, 394-408 (2000).

Ward, E. S., et al., "Evidence to support the cellular mechanism involved in serum IgG homeostatis in humans" *International Immunology*, 15(2):187-195 (2003).

Warmerdam, P. A., et al., "Interaction of a human Fc gamma RIIb1 (CD32) isoform with murine and human IgG subclasses," *Int Immunol.*, 5(3):239-247 (Mar. 1993).

Wawrzynczak, E. J., et al., "Recombinant mouse monoclonal antibodies with single amino acid substitutions affecting Clq and high affinity Fc receptor binding have identical serum half-lives in the BALB/c mouse," *Mol. Immunol.*, 29(2):221-227 (Feb. 1992).

Weiner, L. M., et al., "Tunable antibodies," *Nature Biotechnology*, 23(5):556-557 (May 2005).

Weng, W., et al., "Clinical Outcome of Lymphoma Patients After Idiotype Vaccination Is Correlated With Humoral Immune Response and Immunoglobulin G Fc Receptor Genotype," *J. Clin Oncol.*, 22(23):1-8 (2004).

Weng, W., et al., "Two Immunoglobulin G Fragment C Receptor Polymorphisms Independently Predict Response to Rituximab in Patients With Follicular Lymphoma," *Journal of Clinical Oncology*, 21(21):3940-3947 (Nov. 1, 2003).

West, A. P., et al., "Crystal Structure and immunoglobulin G Binding Properties of the Human Major Histocompatibility Complex-Related Fc Receptor," *Biochemistry*, 39:9698-9708 (2000).

White, et al., "Antibody-targeted immunotherapy for treatment of malignancy," *Annu Rev Med*, 52:125-145 (2001).

WHO Review of the notation for the allotypic and related markers of human immunoglobulins. J Immunogen 1976, 3:357-362.

WHO Review of the notation for the allotypic and related markers of human immunoglobulins. 1976, Eur. J. Immunol. 6, 599-601.

Wines, B.D. et al. "The IgG Fc contains distinct Fc receptor (FcR) binding sites: the leukocyte receptors Fc[gamma] RIIa bind to a region in the Fc distinct from that recognized by neonatal FcR and protein A" *Journal of Immunology*, (2000), pp. 5313-5318.

Wing, M. G., et al., "Mechanism of First-Dose Cytokine-Release Syndrome of CAMPATH 1-H:involvement of CD16 (Fcγ RIII) and CD11a/CD18 (LFA-1)on NK Cells," *J. Clin. Invest.*, 98(12):2819-2826 (Dec. 1996).

(56) References Cited

OTHER PUBLICATIONS

Wolff, E.A., et al., "Monoclonal antibody homodimers: enhanced antitumor activity in nude mice," *Cancer Res.*, 53(11):2560-2565 (Jun. 1, 1993).
Woof, J.M. et al. "Localisation of the Monocyte-Binding Region on Human Immunoglobulin G" *Molecular Immunology*, 1986, vol. 23, No. 3, pp. 319-330.
Wright, A., et al., "Effect of C2-Associated carbohydrate Structure on Ig Effector Function: Studies with Chimeric Mouse-Human IgG1 Antibodies in Glycosylation Mutants of Chinese Hamster Ovary Cells" *J. of Immunology*, 160:3393-3402 (1998).
Wright, A., et al., "In vivo trafficking and catabolism of IgG1 antibodies with Fc associated carbohydrates of differing structure," *Glycobiology*, 10(12):1347-1355 (2000).
Xu, D., et al., "In Vitro Characterization of Five Humanized OKT3 Effector Function Varient Antibodies," *Cellular Immunology*, 200:16-26 (2000).
Xu, M., et al., "Molecular Cloning and Characterization of SPAP1, an Inhibitory Receptor," *Biochemical and Biophysical Research Communications*, 280:768-775 (2001).
Xu, Y., et al., "Residue at Position 331 in the IgG1 and IgG4 $C_H2$ Domains Contributes to Their Differential Ability to Bind and Activate Complement" *J. Biol. Chem.* 269(5):3469-3474 (1994).
Yamane-Ohnuki N. et al., "Establishment of FUT8 knockout chinese hamster ovary cells: an ideal host cell line for producing completely defucosylated antibodies with enhanced antibody-dependent cellular cytoxicity", *Biotechnology and Bioengineering Interscience Publishers, London, GB*, vol. 87, No. 5, Sep. 5, 2004.
Zelaschi, D., et al., "Human immunoglobulin allotypes: previously unrecognized determinants and alleles defined with monoclonal antibodies," *PNAS, USA*, 80:3762-3766 (Jun. 1983).
Zhou, H., et al., "DNA-based vaccines activate innate and adaptive antitumor immunity by engaging the NKG2D receptor" *PNAS*, 102(31):10846-10851 (Aug. 2, 2005).
Zhou, J., et al., "Generation of Mutated Variants of the Human Form of the MHC Class I-related Receptor, FcRn, with Increased Affinity for Mouse Immunoglobulin G," *J. Mol. Biol.*, 332(4):901-13 (Sep. 2003).
Zhu, D., et al., "A novel human immunoglobulin Fc gamma Fc epsilon bifunctional fusion protein inhibits Fc epsilon RI-mediated degranulation," *Nat Med.*, 8(5):518-521 (May 2002).
U.S. Appl. No. 10/339,788, filed Dec. 18, 2001, Abandoned.
Alegre, et al., "A non-activatin "Humanized" Anti-CD3 Monoclonal Antibody Retains Immunosuppressive Properties In Vivo" Transplatation, 1994, 1537-1543, vol. 57.
Amigorena, et al., "Fc receptor signaling and trafficking: a connection for antigen processing" Immunol. Rev., 1999, 279-284, vol. 172.
Anderson, et al., "An expanded genetic code with a functional quadruplet codon" Proc. Nat. Acad. Sci., 2004, 7566-7571, vol. 101.
Atwell, et al. "Stable Heterodimers from Remodeling the Domain Interface of a Homodimer using a Phage Display Library" J. Mol. Bioi, 1997,26-35, vol. 270.
Baca, et al., "Antibody Humanization Using Monovalent Phage Display" J. Biol. Chem., 1997,10678-10684, vol. 272, No. 16.
Bayry, et al "Mechanisms of action of intravenous immunoglobulins in autoimmune and inflammatory diseases" Transfusion Clinique et biologique, 2003,165-169, vol. 10, No. 3.
Beigier-Bompadre, et al "The Formyl Peptide N-Fornyl-methionly-leucyl-phenylalanine Downregulates the Expression of FcγRs in Interferon-γ-Activated Monocytes/Macrophages In Vitro and In Vivo" Scand. J. Immunol., 2003, 221-228, vol. 57.
Binstadt, et al "IgG Fc receptor polymorphisms in human disease: Implications for C10 intravenous immunoglobulin therapy" J. Allergy and Clinical Immuno., (2003), 697-703, vol. 111, No. 4.
Bitonti, et al "Pulmonary delivery of an erythropoietin Fc fusion protein in non-human C11 primates through an immunoglobulin transport pathway" Proc. Natl. Acad. Sci., 2004, 9763-9768, vol. 101.
Bogan & Thorn, 1998, "Anatomy of Hot Spots in Protein Interfaces", *J. Mol. Biol.*, vol. 280, pp. 1-9.

Bruggemann, et al "Production of human antibody repertoires in transgenic mice" Current Opinion in Biotech., 1997,455-458, vol. 8.
Carter, et al., "Bispecific human IgG by design" J. Immunol. Methods, 2001, 7-15, vol. 248.
Chari, et al., "Immunoconjugates containing novel maytansinoids: Promising anticancer drugs" Cancer Res., 1992, 127-131, vol. 52.
Chin, et al "An Expanded Eukaryotic Genetic Code" Science, 2003, 964-967, vol. 301.
Clarkson & Wells, 1995, "A Hot Spot of Binding Energy in a Hormone-Receptor Interface", Science vol. 267, pp. 383-386.
Cobleigh, et al., "Multinational Study of the Efficacy and Safety of Humanized Anti-HER2 Monoclonal Antibody in Women who have HER2-Overexpressing Metastatic Breast Cancer that has progressed after chemotherapy for metastatic disease" J. Clin. Oncol., 1999, 2639-2648, vol. 17.
Cropp, et al., "An expanding genetic code" Trends in Genetics, 2004, 625-630, vol. 20, No. 12.
Cunningham & Wells, 1989, "High-Resolution Epitope Mapping of hGH-Receptor Interactions by Alanine—Scanning Mutagenesisi", Dept. of Biomolecular Chemistry, Genentech—Science vol. 244, pp. 1081-1085.
Dall'Ozzo, et al "Rituximab-Dependent Cytotoxicity by Natural Killer Cells: Influence of FCGR3A Polymorphism on the Concentration-Effect Relationship" Cancer Research, 2004, 4664-4669, vol. 64.
De Pascalis, et al., "Grafting of "Abbreviated" Complementarity-Determining Regions Containing Specificity-Determining Residues Essential for Ligand Contact to Engineer a less Immunogenic Humanized Monoclonal Antibody" J. Immunol., 2002, 3076-3084, vol. 169.
Deisenhofer, et al., "Crystallographic Refinement and Atomic models of a Human Fc Fragment and Its Complex with Fragment B of Protein A from *Staphylococcus aureus* at 2.9- and 2.8 A resolution" Biochem. 1981, 2361-2370 vol. 20, No. 9.
Dhodapkar, K.M., et al., "Selective blockade of inhibitory Fc receptor enables human dendritic cell maturation with IL-12p70 production and immunity to antibody-coated tumor cells" PNAS, 102(8):2910-2915 (Feb. 22, 2005).
Dickinson, et al., "Bidirectional FcRn-dependent IgG transport in a polarized human intestinal epithelial cell line" J. Clin. Invest., 1999, 903-911, vol. 104.
Doronina, et al, "Development of potent monoclonal antibody auristatin conjugates for cancer therapy" Nature Biotech., 2003, 778-784, vol. 21, No. 7.
Dove, et al, "Uncorking the biomanufacturing bottleneck" Nature Biotech., 2002, 777-779, vol. 20.
Dyer, et al., "Effects of CAMPATH-1 antibodies in vivo in patients with lymphoid malignancies: influence of antibody isotype" Blood, 1989, 1431-1439, vol. 73.
Eppstein, et al "Biological activity of liposome-encapsulated murine interferon y is mediated by a cell membrane receptor" Proc. Natl. Acad. Sci., 1985, 3688-3692, vol. 82.
Ernst, L. K., et al., "Molecular characterization of six variant Fc receptor class I (CD64) transcripts," Molecular Immunology, 35:943-954 (1998).
Finkle, et al., "HER2-Targeted Therapy Reduces Incidence and Progession of Midlige Mammary Tumors in Female Murine Mammary Tumor Virus huHER2-Transgenic Mice" Clin. Cancer Res., 2004, 2499-2511, vol. 10.
Francisco, et al "cAC10-voMMAE, an anti-CD30-monomethyl auristatin E conjugate with potent and selective antitumor activity" Blood, 2003, 1458-1465, vol. 102, No. 4.
Friend, et al., "Reversal of allograft rejection using the monoclonal antibody, campath-1G" Transplant. Proceedings., 1991, 2253-2254, vol. 23, No. 4.
Gabizon, et al "Pharmacokinetics and Tissue Distribution of Doxorubicin Encapsulated in Stable Liposomes with Long Circulation Time" J. Natl. Cancer Inst., 1989, 1484-1488, vol. 18.
Garber, et al., "Biotech industry faces new bottleneck" Nature Biotech., 2001, 184-185, vol. 10.
Gerstner, et al., "Sequence plasticity in the antigen-binding site of a therapeutic anti-HER2 antibody" J. Mol. Biol., 2002, 851-862, vol. 321.

(56) References Cited

OTHER PUBLICATIONS

Gorman, et al., "Reshaping a therapeutic CD4 antibody" Proc. Natl. Acad. Sci., 1991, 4181-4185, vol. 88.
Griffiths, et al "Strategies for selection of antibodies by phage display" Current Opinion in Biotech, 1998, 102-108, vol. 9.
Guerois et al., 2002, Predicting Changes in the Stability of Proteins and Protein Complexes: A Study of More than 1000 Mutations, J. Biol. Mol. vol. 320, pp. 369-387.
Hale, et al., "Improving the outcome of bone marrow transplantation by using CD52 monoclonal antibodies to prevent graft-versus-host disease and graft rejection" Blood, 1998, 4581-4590, vol. 92.
Hale, et al., "Synthetic peptide mimotope of the CAMPATH-1 (CD52) antigen, a small glycosylphospatidylinositol-anchored glycoprotein" Immunotech., 1995, 175-187, vol. 1.
Hale, et al., "The CAMPATH-1antigen (CDw2)" Tissue Antigens, 1990, 118-127, vol. 35, No. 3.
Hammer, et al., "Precise prediction of major histocompatibility complex class II-peptide interaction based on peptide side chain scanning" J. Exp. Med., 1994, 2353-2358, vol. 180.
Hazenbos, W.L., et al., "Murine IgG1 complexes Trigger Immune Effector Functions Predominately via Fc RIII (CD16)," J. of Immunology, 161:3026-3032 (1998).
He, et al., "Humanization and Pharmacokinetics of a Monoclonal antibody with specificity for both E- and P-selectin" J. Immunol., 1998, 1029-1035, vol. 160.
Hinman, et al "Preparation and Characterization of Monoclonal Antibody Conjugates of the Calicheamicins: A Novel and Potent Family of Antitumor Antibiotics" Cancer Research, 1993, 3336-3341, vol. 53.
Horton et al., 2008, "Potent In Vitro and In Vivo Activity of an Fc-Engineered Anti-CD19 Monoclonal Antibody against Lymphoma and Leukemia", Cancer Res., vol. 68 (19), pp. 8049-8057.
Hwang, et al, "Hepatic uptake and degradation of unilamellar sphingomyelin/ cholesterol liposomes: A kinetic study" Proc. Natl. Acad. Sci, 1980, 4030-4034, vol. 77, No. 7.
Issacs, J. D., et al., "Therapy with Monoclonal Antibodies, II. The contribution of Fc Receptor binding and the Influenece of CH1 and CH3 Domains on In Vivo Effector Function," J. of Immunology, 161:3862-3869 (1998).
James, et al.,"1.9 A Structure of the Therapeutic Antibody CAMPATH-1H Fab in Complex with a Synthetic Peptide Antigen" J. Mol. Biol., 1999, 293-301, vol. 289.
Janin & Chothia, 1990, "The Structure of Protein-Protein Recognition Sites", J. Bio. Chem. 16207-16030.
Jassal, et al., "Sialylation of human IgG-Fc carbohydrate by transfected rat alpha2, 6-sialytrasnferase" Biochem &Biophysical Res. Comm. vol. 286, No. 2, pp. 243-249 (2001).
Jefferies, et al., "Modulation of Fc R and Human Complement Activation by IgG3-core oligosaccharide interractions" Immunol Lett, 54:101-104 (1996).
Jefferis "Antibody therapeutics: isotype and glycoform selection" Expert Opin. Biol. Ther., 2007, 1401-1413, vol. 7(9).
Jefferis, R., et al., "Interaction sites on human IgG-Fc for Fc R: current models," Immunology Letts., 82:57-65 (2002).
Jefferis, R., et al., "Modulation of Fc R and human complement activation by IgG3-core oligosaccharide interactions," Immunology Letters, 54:101-104 (1996) and errata at Immunology Letters, 58:67 (1997).
Jones & Thorton, 1996, "Principles of protein-protein interactions", PNAS, vol. 93, pp. 13-20.
Jones, et al "Replacing the complementarity-determining regions in a human antibody with those from a mouse" Nature, 1986, 522-525, vol. 321.
Jungbluth, et al., "A monoclonal antibody recognizing human cancers with amplification / overexpression of the human epidermal growth factor receptor" Proc. Natl. Acad. Sci., 2003, 639-644, vol. 100, No. 2.

Kalergis, A.M., et al., "Inducing Tumor Immunity through the Selective Engagement of Activating Fc Receptors on Dendritic Cells" J. Exp. Med. 195(12):1653-1659 (Jun. 17, 2002).
Kan, K. S., et al., "Thioether-Bonded Constructs of Fab' and Fc Modules Utilizing Differential Reduction of Interchain Disulfide Bonds," Journal of Immunology, 166:1320-1326 (2001).
Kettleborough, et al. "Humanization of a mouse monoclonal antibody by CDR-grafting: the importance of framework residues on loop conformation" Protein Engin., 1991, 773-783, vol. 4, No. 7.
Kilmartin, et al "Rat Monoclonal Antitubulin Antibodies Derived by Using a New Nonsecreting Rat Cell Line" Mol. Biol., 1982, 576-582, vol. 93.
Kim, T. D., et al., "Analysis of Fc RIII and IgG Fc Polymorphism Reveals Functional and Evolutionary Implications of Protein-Protein Interaction," J. Mol. Evol., 53:1-9 (2001).
Krauss, et al., "Specificity grafting of human antibody frameworks selected from a phage display library: generation of a highly stable humanized anit-CD22 single-chain Fv fragment" Protein Engineering, 2003, 753-759, vol. 16.
Kurucz, I., et al., "Bacterially expressed human Fc RIIb is soluble and functionally active after in vitro refolding" Immunology Letts., 75:33-40 (2000).
Lehrnbecher, et al., "Variant Genotypes of the Low-Affinity Fc Receptors in Two Control Populations and a Review of Low-Affinity Fc Receptor Polymorphisms in Control and Disease Populations," Blood, 94:4220-4232 (1999).
Little, et al., "Of mice and men: hybridoma and recombinant antibodies" Immunol. Today, 2000, 364-370, vol. 21.
Lo Conte et al., 1999, "The Atomic Structure of Protein-Protein Recognition Sites", J. Mol. Biol. , vol. 285, ps. 2177-2198.
Lode, et al "Targeted therapy with a novel enediyne antibiotic calichemamicin f I I effectively suppresses growth and dissemination of liver metastases in a syngeneic model of murine neuroblastoma" Cancer Research, 1998, 2925-2928, vol. 58.
Lowman, et al "Selecting high-affinity binding proteins by monovalent phage display" Biochemistry, 1991, 10832-10838 , vol. 30, No. 45.
Maenaka, K., et al., "The Human Low Affinity Fc Receptors IIa, IIb and III Bind IgG with Fast Kinetics and Distinct Thermodynamic Properties" J. Biol. Chem.276(48):44898-44904 (2001).
Mallios, et al., "Class II MHC quantitative binding motifs derived from a large molecular database with a versatile iterative stepwise discriminant analysis meta-algorithm" Bioinformatics, 1999, 432-439, vol. 15.
Mallios, et al., "Predicting class II MHC/peptide multi-level binding with an iterative stepwise discriminant analysis meta-algorithm" Bioinformatics, 2001, 942-948, vol. 17.
Marshall, et al., "Prediction of Peptide Affinity to HLA DRB1*0401" J. Immunol., 1995, 5927-5933, vol. 154.
Massey, "Catalytic antibodies catching on" Nature, 1987, 457-458, vol. 320.
Mateo, et al., "Humanization of a mouse monoclonal antibody that blocks the epidermal growth factor receptor: recovery of antagonistic activity" Immunotech., 1997, 71-81, vol. 3.
McLaughlin, et al., "Rituximab Chimeric Anti-CD20 Monoclonal Antibody Therapy for Relapsed Indolent Lymphoma: Half of Patients Respond to a Four-Dose Treatment Program" J. Clin. Oncol., 1998, 2825-2833, vol. 16.
Medesan, et al., "Delineation of the Amino Acid Residues Involved in Transcytosis and Catabolism of Mouse IgG1" J. Immunol., 1997, 2211-2217, vol. 158.
Metes. D., et al., "Expression of Functional CD32 Molecules on Human NK Cells Is Determined by and Allelic Polymorphism of the Fc RIIC Gene," Blood, 91(7):2369-2380 (Apr. 1, 1998).
Mimura, Y., et al., "Role of Oligosaccharide Residues of IgG1-Fc in Fc RIIb Binding," J. Biol. Chem., 276(49):45539-45547 (Dec. 7, 2001).
Modjtahedi, et al., "Antitumor Activity of Combinations of Antibodies Directed Against Different Epitopes on the Extracellular Domain of the Human EGF Receptor" Cell Biophyics, 1993, 129-146,vol. 22.
Modjtahedi, et al., "Phase I trial and tumour localization of the anti-EGFR monoclonal antibody ICR62 in head and neck or lung cancer" Bt. J. Cancer, 1996, 228-235, vol. 73.

(56) References Cited

OTHER PUBLICATIONS

Modjtahedi, et al., "Targeting of Cells Expressing Wild-Type EGFR and Type-III Mutant EGFR (EGFRVIII) by Anti-EGFR MAB ICR62: A Two-Pronged Attack for Tumour Therapy" Int. J. Cancer, 2003, 273-280, vol. 105.
Modjtahedi, et al., "The human EGF receptor as a target for cancer therapy: six new rat mAbs against the receptor on the breast carcinoma MDA-MB 468" Bt. J. Cancer, 1993, 247-253, vol. 67.
Morea, et al "Antibody structure, prediction and redesign" Biophysical Chem., 1997, 9-16, vol. 68.
Murthy, et al., "Binding of an Antagonistic Monoclonal Antibody to an Intact and Fragmented DGF-Receptor Polypeptide" Archives of Biochem and Biophys., 1987, 549-560, vol. 252, No. 2.
Newman, et al., "Primatization of recombinant antibodies for immunotherapy of human diseases: A Macaque/Human chimeric antibody against human CD4" Biotech., 1992, 1455-1460, vol. 10.
Nimmerjahn, F., et al., "Fc RIV: A Novel FcR with Distinct IgG Subclass Specificity," Immunity, 23:41-51 (Jul. 2005).
Okazaki, A., et al., "Fucose Depletion from Human IgG1 Oligosaccharide Enhances Binding Enthalpy and Association Rate Between IgG1 and Fc RIIIa," J. Mol. Biol., 336:1239-1249 (2004).
Otzen & Fersht, 1999, "Anlaysis of protein-protein interactions by mutagenesis: direct versus indirect effects", Protein Engineering, vol. 12, pp. 41-45.
Presta, et al., "Humanization of an Anti-Vascular Endothelial Growht Factor Monoclonal Antibody for the Therapy of Solid Tumors and Other Disorders" Cancer Res., 1997, 4593-4599, vol. 57.
Presta, L.G., et al., "Engineering Antibodies for Therapy" Curr. Pharma. Biotechnology, 2002, vol. 3, 237-256.
Queen, et al., "A humanized antibody that binds to the Interleukin 2 Receptor" *Proc. Natl. Acad. Sci.*, 1989, 10029-10033, vol. 86.
Radaev, S., et al., "Review: Recognition of immunoglobulins by Fc recptors," Molecular Immunology, 38:1073-1083 (2001).
Radaev, S., et al., "The Structure of Human Type III Fc Receptor in Complex with Fc," J. Biol. Chem., 276(19):16469-16477 (May 11, 2001).
Rader, et al.,"A phage display approach for rapid antibody humanization: Designed combinatorial V gene libraries" Proc. Natl. Acad. Sci., 1998, 8910-8915, vol. 95.
Redpath, S., et al., "The Influence of the Hinge Region Length in Binding of Human IgGto Human Fc Receptors," Human Immunology, 59:720-727 (1998).
Reichmann et al., 2007, "Binding Hot Spots in the TEM1-BLIP Interface in Light of its Modular Architecture", J. Mol. Biol., vol. 365, 663-679.
Reichmann et al., 2007, "The molecular architecture of protein-protein binding sites", Curr. Opn. Structc. Biol., vol. 17, pp. 67-76.
Richards et al., 2008, "Optimization of antibody bidning to FCγRIIa enhances macrophage phagocytosis of tumor cells", Mol. Cancer Ther., vol. 7(8), pp. 2517-2527.
Riechmann, et al., "Reshaping human antibodies for therapy" Nature, 1988, 323-327, vol. 332.
Rodeck, et al., "Interactions between growth factor receptors and corresponding monoclonal antibodies in human tumors" J. Cell Biochem., 1987, 315-320, vol. 35.
Roguska, et al., "Humanization of Murine monoclonal Antibodies through variable domain resurfacing" Proc. Natl. Acad. Sci., 1994, 969-973, vol. 91.
Rosok, et al., "A combinatorial library strategy for the rapid humanization of anticarcinoma BR96 Fab" J. Biol. Chem., 1996, 22611-22618, vol. 271, No. 37.
Samuelsson, et al "Anti-inflammatory activity of IVIG mediated through the inhibitory Fc receptor" Science, 2001, 484-486, vol. 291.
Sauer-Eriksson, et al., "Crystal structure of the C2 fragment of streptococcal protein G in complex with the Fc domain of human IgG" Structure, 1995, 265-278, vol. 3.
Schreiber & Fersht, 1995, "Energetics of Protein-Protein Interactions: Analysis of the Barnase-Barstar Interface by Single Mutations and Double Mutant Cycles", J. Biol. Mol., vol. 248, pp. 478-486.
Shields, R. L., et al., "High Resolution Mapping of the Binding Site on Human IgG1 for Fc RI, Fc RII, Fc RIII, and FcRn and Design of IgG1 Varients with Improved Binding to the Fc R" J. Biol. Chem., 276(9):6591-6604 (2001).
Shields, R. L., et al., "Lack of Fucose on human IgG1 N-Linked Oligodaccharide Improves Binding to Human Fc RIII and Antibody-dependent Cellular Toxicity" J. Biol. Chem., 277(30)26733-26740 (2002).
Simon, et al., "Peptoids: A modular approach to drug discovery" Proc. Natl. Acad. Sci., 1992, 9367-9371, vol. 89.
Smith, "Filamentous fusion phage: Novel expression vectors that display cloned antigens on the virion surface" Science, 1985, 1315-1317.
Sondermann, P. et al., "Crystal structure of the soluble form of the human FC-receptor IIb: a new member of the immunoglobulin superfamily at 1.7Å resolution" EMBO Journal, 18(5):1095-1103 (1999).
Sondermann, P., et al., "Human Fc Receptor IIb Expressed in *Escherichia coli* Reveals IgG Binding Capability" Biol. Chem. 380:717-721 (Jun. 1999).
Stella, et al., "Direceted Drug Delivery" 1985, The Humana Press, Inc.
Stevenson, et al "Engineered antibody for treating lymphoma" Recent Res. In Cancer Research, 2002, 105-112, vol. 159.
Stevenson, G. T., et al., "Preparation of Fc for addition to sulfhydryl-expressing ligands with minimal disturbance of the hinge," J. of Immunological Methods, 231:169-175 (1999).
Sturniolo, et al., "Generation of tissue-specific and promiscuous HLA ligand databases using DNA microarrays and virtual HLA class II matrices" Nature Biotech., 1999, 555-561, vol. 17.
Tamm, A. et al., "IgG Binding Sites on Human Fc Receptors" 1997, International Reviews of Immunology, 16:1,57-85.
Tan, et al ""Superhumanized" Antibodies: Reduction of Immunogenic Potential by Complementarity-Determining Region Grafting with Human Germline Sequences: Application to an Anti-CD28" J.Immunol., 2002, 1119-1125, vol. 169.
Tashiro, et al., "Structures of bacterial immunoglobulin-binding domains and their complexes with immunoglobulins" Current Opinion Struct. Biol., 1995, 471-481, vol. 5.
Tsurushita, et al "Humanization of Monoclonal Antibodies" Molecular B Cells, 2004, 533-545.
Tutuncu, et al., "Fcγ receptor type IIIA polymorphisms influence treatment outcomes in patients with inflammatory arthritis treated with tumor necrosis factor a-blocking agents" Arthritis & Rheumatism, 2005, 2693-2696, vol. 52, vol. 9.
Van Mirre, et al., "Monomeric IgG in intravascular Ig preparations is a functional antagonist of FcγRII and FcγRIIIb" J. Immunol., 2004, 332-339, vol. 173.
Van Royen-Kerkhof, A, et al., "Flow cytometric determination of Fc RIIa (CD32) polymorphism," J. Immunol. Methods, 294:135-144 (2004).
Van Schie, R.C.A.A., et al., "Evaluation of Human Fc RIIA (CD32) and Fc RIIIB (CD16) Polymorphisms in Caucasians and African-Americans Using Salivary DNA," Clinical and Diagnostic Laboratory Immunology, 7(4):676-681 (Jul. 2000).
Van Sorge, N., et al., "Fc R polymorphisms: Implications for function, disease susceptibility and immunotherapy," Tissue Antigens, 61:189-202 (2003).
Verhoeyen, et al "Reshaping Human Antibodies: Grafting an Antilysozyme Activity" Science, 1988, 1534-1536, vol. 239, No. 4847.
Vitetta, et al., "Redesigning Nature's Posions to Create Anti-Tumor Reagents" Science, 1987, 1098-1104, vol. 238.
White, et al., "Design and Expression of Poymeric Immunoglobulin Fusin Proteins: A Strategy for Targeting Low-Affinity Fcγ Receptors" *Protein Expression and Purification*, 2001, 446-455, vol. 21.
Wilman, et al., "Prodrugs in cancer chemotherapy" Action Cancer Guest Lecture, 615th meeting, Belfast, 1986, 375-382, vol. 14.
Wing, M. G., et al., "Mechanism of First-Dose Cytokine-Release Syndrome of CAMPATH 1-H:Involvement of CD16 (Fc RIII) and CD11a/CD18 (LFA-1)on NK Cells," J. Clin. Invest., 98(12):2819-2826 (Dec. 1996).

(56) References Cited

OTHER PUBLICATIONS

Wu, et al., "Humanization of a murine monoclonal antibody by simultaneous optimization of framework and CDR residues" J. Mol. Biol., 1999, 151-162, vol. 294.

Yoshida, et al "Human Neonatal Fc Receptor Mediates Transport of IgG into Lumina! Secretions for Delivery of Antigens to Mucosal Dendritic Cells" 2004, 769-783, vol. 20.

Young et al., 1997, "Characterization of the receptor binding determinants of granulocyte colony stimulating factor", Protein Science, vol. 6, pp. 1228-1236.

Zalevsky et al., 2009, "The impact of Fc Engineering on an anti-CD19 antibody: increased Fcγ receptor affinity enhances B-cell clearing in nonhuman primates", Blood, vol. 113 (16), pp. 3735-3743.

Zhang, et al "A new strategy for the synthesis of gylcoproteins" Science, 2004, 371-373, vol. 303.

Dillon T. et al. "Structural and Functional Characterization of Disulfide Isoforms of the Human IgG2 Subclass" J. of Bio Chem vol. 283 No. 023 pp. 16206-16215 (2008).

Cheng Yuping et al. "HBsAg RBC Minibody" Journal of Chinese Immunology vol. 17 No. 6 Dec. 31, 2001.

\* cited by examiner

Figure 1

| Cell type | FcγR-dependent effector function(s) | Activation determined by engagement of which activating vs. inhibitory FcγRs |
|---|---|---|
| NK | ADCC | FcγRIIIa only |
| Neutrophil | Phagocytosis ADCC | FcγRI vs. FcγRIIb<br>FcγRIIa vs. FcγRIIb<br>FcγRIIIa vs. FcγRIIb |
| Macrophage | Phagocytosis ADCC | FcγRI vs. FcγRIIb<br>FcγRIIa vs. FcγRIIb<br>FcγRIIIa vs. FcγRIIb |
| Dendritic cell | CTL cross-priming B-cell ag presentation | FcγRI vs. FcγRIIb<br>FcγRIIa vs. FcγRIIb<br>FcγRIIIa vs. FcγRIIb |

Figure 2a

| CH1 | | | | | | | | | | | | | | | | | | | | |
|---|---|---|---|---|---|---|---|---|---|---|---|---|---|---|---|---|---|---|---|---|
| EU Index | 118 | 119 | 120 | 121 | 122 | 123 | 124 | 125 | 126 | 127 | 128 | 129 | 130 | 131 | 132 | 133 | 134 | 135 | 136 | 137 | 138 |
| IgG1 | A | S | T | K | G | P | S | V | F | P | L | A | P | S | S | K | S | T | S | G | G |
| IgG2 | A | S | T | K | G | P | S | V | F | P | L | A | P | C | S | R | S | T | S | E | S |
| IgG3 | A | S | T | K | G | P | S | V | F | P | L | A | P | C | S | R | S | T | S | G | G |
| IgG4 | A | S | T | K | G | P | S | V | F | P | L | A | P | C | S | R | S | T | S | E | S |

| EU Index | 139 | 140 | 141 | 142 | 143 | 144 | 145 | 146 | 147 | 148 | 149 | 150 | 151 | 152 | 153 | 154 | 155 | 156 | 157 | 158 | 159 |
|---|---|---|---|---|---|---|---|---|---|---|---|---|---|---|---|---|---|---|---|---|---|
| IgG1 | T | A | A | L | G | C | L | V | K | D | Y | F | P | E | P | V | T | V | S | W | N |
| IgG2 | T | A | A | L | G | C | L | V | K | D | Y | F | P | E | P | V | T | V | S | W | N |
| IgG3 | T | A | A | L | G | C | L | V | K | D | Y | F | P | E | P | V | T | V | S | W | N |
| IgG4 | T | A | A | L | G | C | L | V | K | D | Y | F | P | E | P | V | T | V | S | W | N |

| EU Index | 160 | 161 | 162 | 163 | 164 | 165 | 166 | 167 | 168 | 169 | 170 | 171 | 172 | 173 | 174 | 175 | 176 | 177 | 178 | 179 | 180 |
|---|---|---|---|---|---|---|---|---|---|---|---|---|---|---|---|---|---|---|---|---|---|
| IgG1 | S | G | A | L | T | S | G | V | H | T | F | P | A | V | L | Q | S | S | G | L | Y |
| IgG2 | S | G | A | L | T | S | G | V | H | T | F | P | A | V | L | Q | S | S | G | L | Y |
| IgG3 | S | G | A | L | T | S | G | V | H | T | F | P | A | V | L | Q | S | S | G | L | Y |
| IgG4 | S | G | A | L | T | S | G | V | H | T | F | P | A | V | L | Q | S | S | G | L | Y |

| EU Index | 181 | 182 | 183 | 184 | 185 | 186 | 187 | 188 | 189 | 190 | 191 | 192 | 193 | 194 | 195 | 196 | 197 | 198 | 199 | 200 | 201 |
|---|---|---|---|---|---|---|---|---|---|---|---|---|---|---|---|---|---|---|---|---|---|
| IgG1 | S | L | S | S | V | V | T | V | P | S | S | S | L | G | T | Q | T | Y | I | C | N |
| IgG2 | S | L | S | S | V | V | T | V | P | S | S | N | F | G | T | Q | T | Y | T | C | N |
| IgG3 | S | L | S | S | V | V | T | V | P | S | S | S | L | G | T | Q | T | Y | T | C | N |
| IgG4 | S | L | S | S | V | V | T | V | P | S | S | S | L | G | T | K | T | Y | T | C | N |

| EU Index | 202 | 203 | 204 | 205 | 206 | 207 | 208 | 209 | 210 | 211 | 212 | 213 | 214 | 215 | 216 | 217 | 218 | 219 | 220 |
|---|---|---|---|---|---|---|---|---|---|---|---|---|---|---|---|---|---|---|---|
| IgG1 | V | N | H | K | P | S | N | T | K | V | D | K | K | V | E | P | K | S | C |
| IgG2 | V | D | H | K | P | S | N | T | K | V | D | K | T | V | E | R | K | C | C |
| IgG3 | V | N | H | K | P | S | N | T | K | V | D | K | R | V | E | L | K | T | P |
| IgG4 | V | D | H | K | P | S | N | T | K | V | D | K | R | V | E | S | K | Y | G |

Hinge                  Fc >

| EU Index | 221 | 222 | 223 | 224 | 225 | 226 | 227 | 228 | | | | | | | | | | | |
|---|---|---|---|---|---|---|---|---|---|---|---|---|---|---|---|---|---|---|---|
| IgG1 | D | | K | T | H | T | C | P | P | | | | | | | | | | |
| IgG2 | | | V | E | | | C | P | P | | | | | | | | | | |
| IgG3 | L | G | D | T | H | T | C | P | R | C | P | E | P | K | S | C | D | T | P | P |
| IgG4 | | | | P | P | | C | P | S | | | | | | | | | | |

| EU Index | | | | | | | | | | | | | | | | | |
|---|---|---|---|---|---|---|---|---|---|---|---|---|---|---|---|---|---|
| IgG1 | | | | | | | | | | | | | | | | | |
| IgG2 | | | | | | | | | | | | | | | | | |
| IgG3 | P | C | P | R | C | P | E | P | K | S | C | D | T | P | P | P | C | P | R | C | P |
| IgG4 | | | | | | | | | | | | | | | | | |

Fc >

| EU Index | | | | | | | | | | | | | 229 | 230 | 231 | 232 | 233 | 234 | 235 | 236 | |
|---|---|---|---|---|---|---|---|---|---|---|---|---|---|---|---|---|---|---|---|---|---|
| IgG1 | | | | | | | | | | | | | C | P | A | P | E | L | L | G | SEQ ID NO: 21 |
| IgG2 | | | | | | | | | | | | | C | P | A | P | P | V | A | | SEQ ID NO: 22 |
| IgG3 | E | P | K | S | C | D | T | P | P | P | C | P | R | C | P | A | P | E | L | L | G | SEQ ID NO: 23 |
| IgG4 | | | | | | | | | | | | | C | P | A | P | E | F | L | G | SEQ ID NO: 24 |

| Allotype | Allotype | Position | | |
|---|---|---|---|---|
| | | 214 | 356 358 | 431 |
| G1m(1,17) | G1m(a,z) | K | D L | A |
| G1m(1,2,17) | G1m(a,x,z) | K | D L | G |
| G1m(3) | G1m(f) | R | E M | A |
| G1m(1,3) | G1m(a,f) | R | D L | A |

Figure 3b

| Allotype | Allotype | Position |
|---|---|---|
| | | 282 |
| G2m(23) | G2m(n+) | V |
| | G2m(n-) | M |

| Variant | FcγRI IC50 (M) | FcγRI Fold WT | R131 FcγRIIa IC50 (M) | R131 FcγRIIa Fold WT | H131 FcγRIIa IC50 (M) | H131 FcγRIIa Fold WT | FcγRIIb IC50 (M) | FcγRIIb Fold WT | V158 FcγRIIIa IC50 (M) | V158 FcγRIIIa Fold WT |
|---|---|---|---|---|---|---|---|---|---|---|
| WT | 7.5E-09 | 1.00 | 1.4E-07 | 1.00 | | | 1.8E-07 | 1.00 | 7.7E-08 | 1.00 |
| | | | 1.3E-07 | 1.00 | 6.4E-07 | 1.00 | 2.8E-07 | 1.00 | | |
| I332E | 2.3E-09 | 3.21 | 7.7E-08 | 1.79 | | | 1.2E-07 | 1.59 | 3.2E-09 | 24.15 |
| | | | 3.3E-08 | 4.01 | 7.0E-08 | 9.03 | 7.2E-08 | 3.94 | | |
| S239D | 3.3E-09 | 2.29 | 1.6E-08 | 8.40 | | | 4.3E-08 | 4.22 | 1.6E-09 | 46.88 |
| | | | 2.2E-08 | 6.05 | 2.6E-07 | 2.46 | 5.3E-08 | 5.37 | | |
| S239D/I332E | 1.4E-09 | 5.41 | 2.6E-09 | 53.03 | | | 1.0E-08 | 17.81 | 1.2E-10 | 664.25 |
| | | | 7.9E-09 | 16.88 | 7.7E-08 | 8.21 | 1.4E-08 | 20.91 | | |
| S324I | 5.4E-09 | 1.38 | 2.2E-07 | 0.64 | | | 4.8E-07 | 0.38 | 1.1E-07 | 0.72 |
| A327H | 1.2E-08 | 0.60 | no binding | no binding | | | 6.5E-04 | 0.00 | no binding | no binding |
| L235Y | 7.0E-05 | 0.00 | 1.4E-07 | 1.00 | | | 2.4E-07 | 0.76 | 2.7E-07 | 0.28 |
| | | | 1.4E-07 | 0.99 | 4.8E-07 | 1.33 | 4.1E-07 | 0.69 | | |
| E293R | 5.1E-09 | 1.47 | 1.2E-07 | 1.14 | | | 3.5E-07 | 0.53 | 1.6E-07 | 0.49 |
| A330L | 4.7E-09 | 1.60 | 3.2E-06 | 0.04 | | | 6.4E-06 | 0.03 | 8.8E-08 | 0.87 |
| A330I | 4.4E-09 | 1.70 | 2.2E-04 | 0.00 | | | 5.7E-04 | 0.00 | 1.7E-07 | 0.45 |
| G236A | 2.2E-08 | 0.34 | 1.7E-08 | 7.86 | | | 2.1E-04 | 0.00 | 1.3E-07 | 0.59 |
| | | | 7.4E-09 | 18.04 | 2.5E-08 | 25.79 | 7.7E-06 | 0.04 | | |
| I332D | 3.4E-09 | 2.20 | 5.5E-08 | 2.48 | | | 1.0E-07 | 1.84 | 8.3E-09 | 9.31 |
| | | | 5.6E-08 | 2.40 | 1.5E-07 | 4.28 | 1.3E-07 | 2.25 | | |
| L234I/I332E | 3.2E-09 | 2.33 | 2.9E-07 | 0.48 | | | 1.9E-07 | 0.98 | 3.3E-09 | 23.61 |
| | | | 2.6E-07 | 0.51 | 5.9E-07 | 1.08 | 2.9E-07 | 0.99 | | |
| L234G/I332E | 2.5E-08 | 0.30 | no binding | no binding | | | 6.4E-04 | 0.00 | 7.8E-08 | 0.99 |
| L235D/I332E | 3.5E-07 | 0.02 | 1.3E-06 | 0.11 | | | 5.0E-04 | 0.00 | 4.8E-09 | 16.22 |
| L235E/I332E | 2.0E-08 | 0.38 | 6.6E-05 | 0.00 | | | 3.3E-04 | 0.00 | 1.4E-08 | 5.66 |
| G236S/I332E | 6.7E-09 | 1.12 | 6.2E-08 | 2.20 | | | 7.7E-07 | 0.24 | 6.1E-08 | 1.27 |
| G236A/I332E | 4.4E-09 | 1.69 | 1.4E-08 | 9.78 | | | 5.3E-07 | 0.35 | 5.8E-09 | 13.29 |
| | | | 2.9E-08 | 4.68 | 2.0E-08 | 31.32 | 6.0E-07 | 0.47 | | |
| S267D/I332E | 2.3E-09 | 3.22 | 1.3E-08 | 10.76 | | | 6.8E-08 | 2.71 | 3.0E-09 | 25.89 |
| | | | 2.4E-08 | 5.47 | 4.4E-07 | 1.46 | 8.0E-08 | 3.56 | | |
| Q295E/I332E | 3.6E-09 | 2.09 | 5.9E-07 | 0.23 | | | 8.6E-07 | 0.21 | 1.5E-08 | 5.26 |
| S324I/I332E | 4.1E-09 | 1.85 | 1.9E-07 | 0.71 | | | 2.9E-07 | 0.63 | 1.1E-08 | 6.89 |
| S324G/I332E | 3.5E-09 | 2.17 | 6.0E-07 | 0.23 | | | 8.7E-07 | 0.21 | 6.6E-09 | 11.62 |
| | | | 1.8E-07 | 0.76 | 3.5E-07 | 1.82 | 3.4E-07 | 0.84 | | |
| L328A/I332E | 3.8E-09 | 1.96 | 7.8E-08 | 1.77 | | | 9.5E-08 | 1.93 | 1.7E-07 | 0.46 |
| | | | 6.4E-08 | 2.09 | 1.5E-06 | 0.42 | 9.4E-08 | 3.02 | | |
| L328I/I332E | 2.8E-09 | 2.65 | 1.4E-07 | 1.01 | | | 1.6E-07 | 1.12 | 1.5E-08 | 5.21 |
| S267Q | 4.8E-09 | 1.55 | 4.3E-08 | 3.22 | | | 3.5E-08 | 5.19 | 5.7E-07 | 0.14 |
| | | | 2.2E-08 | 6.06 | 1.0E-04 | 0.01 | 7.8E-08 | 3.62 | | |
| H268D | 2.2E-09 | 3.46 | 1.2E-08 | 11.75 | | | 2.2E-08 | 8.45 | 1.8E-08 | 4.34 |
| | | | 5.2E-08 | 2.57 | 8.1E-07 | 0.78 | 7.7E-08 | 3.67 | | |
| L235I/I332E | 3.3E-09 | 2.26 | 4.1E-08 | 3.31 | | | 3.8E-08 | 4.78 | 2.4E-09 | 32.43 |
| L328F/I332E | 2.0E-09 | 3.80 | 5.2E-08 | 2.62 | | | 5.3E-08 | 3.43 | 1.9E-07 | 0.40 |
| H268E | 2.9E-09 | 2.58 | 2.3E-08 | 6.04 | | | 3.0E-08 | 6.02 | 2.4E-08 | 3.15 |
| | | | 7.2E-09 | 18.59 | 1.8E-07 | 3.58 | 3.7E-08 | 7.67 | | |
| S267E/I332E | 2.1E-09 | 3.60 | 2.5E-09 | 55.29 | | | 8.0E-09 | 22.93 | 2.3E-08 | 3.32 |
| | | | 1.9E-08 | 7.09 | 5.1E-07 | 1.25 | 7.7E-08 | 3.67 | | |
| L235D | no binding | no binding | 3.8E-07 | 0.37 | | | 4.3E-07 | 0.43 | 1.0E-07 | 0.77 |

Figure 9

| | FcγRI | | H131 FcγRIIa | | R131 FcγRIIa | | FcγRIIb | | V158 FcγRIIIa | |
|---|---|---|---|---|---|---|---|---|---|---|
| | IC50 (M) | Fold WT | IC50 (M) | Fold WT | IC50 (M) | Fold WT | IC50 (M) | Fold WT | IC50 (M) | Fold WT |
| WT | 1.22E-09 | 1.00 | 1.0E-07 | 1.00 | 1.6E-07 | 1.00 | 2.6E-07 | 1.00 | 5.6E-08 | 1.00 |
| G236A/I332E | 6.55E-10 | 1.86 | 9.4E-09 | 10.66 | 9.3E-09 | 17.18 | 9.2E-08 | 2.86 | 1.6E-08 | 3.46 |
| S267D/I332E | 3.75E-10 | 3.24 | 1.4E-07 | 0.70 | 1.7E-08 | 9.23 | 2.7E-08 | 9.90 | 6.8E-09 | 8.25 |
| G236A | 3.79E-09 | 0.32 | 1.4E-08 | 7.00 | 2.0E-08 | 8.07 | 8.7E-07 | 0.30 | 9.0E-08 | 0.62 |
| S239D/S267E | 2.70E-10 | 4.51 | 8.1E-08 | 1.24 | 1.6E-09 | 97.43 | 3.8E-07 | 0.69 | 1.7E-08 | 3.31 |
| S239D/H268E/G236A | 5.31E-10 | 2.29 | 4.8E-09 | 20.98 | 1.6E-09 | 97.08 | 2.7E-08 | 9.88 | 4.2E-09 | 13.47 |
| S239D/I332E/L234I | 2.91E-10 | 4.18 | 3.9E-08 | 2.53 | 2.3E-08 | 6.96 | 6.5E-09 | 40.67 | 2.0E-09 | 28.49 |
| S239D/I332E/A330Y/L234I | 2.92E-10 | 4.16 | 3.0E-08 | 3.37 | 3.2E-08 | 5.01 | 3.4E-09 | 78.51 | 1.4E-09 | 39.87 |
| S239D/I332E | 2.93E-10 | 4.16 | 4.7E-08 | 2.11 | 2.4E-08 | 6.66 | 6.8E-09 | 38.95 | 1.9E-09 | 30.16 |
| S239D/I332E/S267E | | | | | | | | | | |
| S239D/I332E/S267D | | | | | | | | | | |
| S239D/I332E/L234I/G236A | 4.91E-10 | 2.48 | 8.4E-09 | 11.84 | 7.1E-09 | 22.34 | 1.2E-08 | 21.55 | 3.9E-09 | 14.39 |
| S239D/I332E/A330Y/G236A | 3.52E-10 | 3.45 | 1.0E-08 | 9.85 | 7.3E-09 | 21.86 | 1.4E-08 | 19.51 | 2.8E-09 | 19.92 |
| L235Y | 3.00E-08 | 0.02 | 6.4E-08 | 1.03 | 9.4E-08 | 1.61 | 2.0E-05 | 0.02 | 1.9E-07 | 0.15 |
| S267E/I332E | 2.10E-10 | 2.46 | 5.4E-08 | 1.21 | 2.8E-09 | 53.46 | 1.1E-07 | 3.90 | 2.4E-08 | 1.15 |
| A330Y/I332E | 2.54E-10 | 2.03 | 6.2E-08 | 1.06 | 7.3E-08 | 2.08 | 1.5E-08 | 29.08 | 3.6E-09 | 7.71 |
| S239D/G236A | 4.79E-10 | 1.08 | 4.9E-09 | 13.34 | 8.8E-10 | 172.06 | 6.4E-08 | 6.64 | 6.7E-09 | 4.11 |
| S239D/S267D | 2.45E-10 | 2.10 | 8.8E-08 | 0.75 | 9.7E-10 | 156.19 | 1.9E-08 | 21.80 | 5.3E-09 | 5.18 |
| S239D/I332E/G236A | 2.62E-10 | 1.97 | 6.9E-09 | 9.52 | 4.0E-09 | 37.65 | 1.3E-08 | 32.11 | 2.1E-09 | 13.00 |
| S239D/I332E/G236A/S267E | | | | | | | | | | |
| S239D/I332E/G236A/S267D | | | | | | | | | | |
| L235Y/S267E | 3.86E-08 | 0.01 | 1.0E-07 | 0.65 | 1.8E-09 | 85.88 | 1.2E-04 | 0.00 | 6.4E-07 | 0.04 |
| I332E | 3.86E-10 | 1.34 | 6.9E-08 | 0.95 | 6.5E-08 | 2.33 | 2.8E-08 | 15.21 | 6.6E-09 | 4.21 |
| S239D/H268E | 3.15E-10 | 1.64 | 3.8E-08 | 1.73 | 4.6E-09 | 33.30 | 1.6E-08 | 26.10 | 2.6E-09 | 10.66 |
| S239D/H268E/S267E | | | | | | | | | | |
| S239D/H268E/S267D | | | | | | | | | | |
| L235Y/S267Q | 1.65E-08 | 0.03 | 4.5E-05 | 0.00 | 5.3E-07 | 0.29 | 3.7E-01 | 0.00 | 7.2E-07 | 0.04 |

Figure 11

| Antibody | IgG | ka (1:Ms) | kd (1:s) | KD (M) | Fold(KD) parent IgG | Fold(KD) WT IgG1 | -log(KD) | ka (1:Ms) | kd (1:s) | KD (M) | Fold(KD) parent IgG | Fold(KD) WT IgG1 | -log(KD) |
|---|---|---|---|---|---|---|---|---|---|---|---|---|---|
| | | | | FcγRI | | | | | | FcγRIIb | | | |
| WT | IgG1 | 2.24E+05 | 2.24E-04 | 1.00E-09 | 1.0 | 1.0 | 9.0 | 4.93E+05 | 1.16 | 2.35E-06 | 1.0 | 1.0 | 5.6 |
| I332E | IgG1 | 1.13E+05 | 1.47E-04 | 1.31E-09 | 0.8 | 0.8 | 8.9 | 3.69E+05 | 0.542 | 1.47E-06 | 1.6 | 1.6 | 5.8 |
| S239D | IgG1 | 1.23E+05 | 1.69E-04 | 1.37E-09 | 0.7 | 0.7 | 8.9 | 7.55E+05 | 0.221 | 2.93E-07 | 8.0 | 8.0 | 6.5 |
| I332E/G236A | IgG1 | 1.05E+05 | 1.06E-04 | 1.01E-09 | 1.0 | 1.0 | 9.0 | 4.55E+05 | 0.448 | 9.83E-07 | 2.4 | 2.4 | 6.0 |
| WT | IgG(hybrid) | 1.11E+05 | 2.17E-04 | 1.96E-09 | 1.0 | 0.5 | 8.7 | 6.36E+05 | 0.403 | 6.35E-07 | 1.0 | 3.7 | 6.2 |
| S239D/I332E | IgG(hybrid) | 1.35E+05 | 8.71E-05 | 6.46E-10 | 3.0 | 1.5 | 9.2 | 4.72E+05 | 0.067 | 1.42E-07 | 4.5 | 16.5 | 6.8 |
| S239D/H268E | IgG(hybrid) | 1.22E+05 | 1.35E-04 | 1.11E-09 | 1.8 | 0.9 | 9.0 | 5.22E+05 | 0.0425 | 8.15E-08 | 7.8 | 28.8 | 7.1 |
| I332E/H268E | IgG(hybrid) | 1.29E+05 | 1.12E-04 | 8.67E-10 | 2.3 | 1.2 | 9.1 | 6.82E+05 | 0.0796 | 1.17E-07 | 5.4 | 20.1 | 6.9 |
| S239D/I332E/G236A | IgG(hybrid) | 1.24E+05 | 1.55E-04 | 1.25E-09 | 1.6 | 0.8 | 8.9 | 4.65E+05 | 0.0678 | 1.46E-07 | 4.3 | 16.1 | 6.8 |
| S239D/I332E/A330Y | IgG(hybrid) | 1.36E+05 | 1.45E-04 | 1.07E-09 | 1.8 | 0.9 | 9.0 | 5.40E+05 | 0.0779 | 1.44E-07 | 4.4 | 16.3 | 6.8 |
| I332E/G236A | IgG(hybrid) | 1.16E+05 | 2.07E-04 | 1.78E-09 | 1.1 | 0.6 | 8.7 | 4.38E+05 | 0.244 | 5.57E-07 | 1.1 | 4.2 | 6.3 |
| I332E/H268E/G236A | IgG(hybrid) | 1.19E+05 | 1.97E-04 | 1.65E-09 | 1.2 | 0.6 | 8.8 | 6.23E+05 | 0.0958 | 1.54E-07 | 4.1 | 15.3 | 6.8 |
| | | | | R131 FcγRIIa | | | | | | H131 FcγRIIa | | | |
| WT | IgG1 | 3.43E+05 | 0.272 | 7.95E-07 | 1.0 | 1.0 | 6.1 | 3.56E+05 | 0.295 | 8.29E-07 | 1.0 | 1.0 | 6.1 |
| I332E | IgG1 | 4.49E+05 | 0.227 | 5.06E-07 | 1.6 | 1.6 | 6.3 | 3.27E+05 | 0.205 | 6.29E-07 | 1.3 | 1.3 | 6.2 |
| S239D | IgG1 | 4.84E+05 | 0.126 | 2.61E-07 | 3.0 | 3.0 | 6.6 | 2.92E+05 | 0.202 | 6.92E-07 | 1.2 | 1.2 | 6.2 |
| I332E/G236A | IgG1 | 5.05E+05 | 0.064 | 1.27E-07 | 6.3 | 6.3 | 6.9 | 2.98E+05 | 0.0285 | 9.56E-08 | 8.7 | 8.7 | 7.0 |
| WT | IgG(hybrid) | 5.15E+05 | 0.212 | 4.11E-07 | 1.0 | 1.9 | 6.4 | 3.28E+05 | 0.161 | 4.93E-07 | 1.0 | 1.7 | 6.3 |
| S239D/I332E | IgG(hybrid) | 6.40E+05 | 0.0499 | 7.80E-08 | 5.3 | 10.2 | 7.1 | 3.30E+05 | 0.0655 | 1.99E-07 | 2.5 | 4.2 | 6.7 |
| S239D/H268E | IgG(hybrid) | 6.44E+05 | 0.0339 | 5.26E-08 | 7.8 | 15.1 | 7.3 | 3.10E+05 | 0.0867 | 2.66E-07 | 1.7 | 2.9 | 6.5 |
| I332E/H268E | IgG(hybrid) | 6.42E+05 | 0.056 | 8.73E-08 | 4.7 | 9.1 | 7.1 | 3.67E+05 | 0.0864 | 2.36E-07 | 2.1 | 3.5 | 6.6 |
| S239D/I332E/G236A | IgG(hybrid) | 6.55E+05 | 9.68E-03 | 1.48E-08 | 27.8 | 53.7 | 7.8 | 3.57E+05 | 0.0127 | 3.57E-08 | 13.8 | 23.2 | 7.4 |
| S239D/I332E/A330Y | IgG(hybrid) | 5.24E+05 | 0.0505 | 9.64E-08 | 4.3 | 8.2 | 7.0 | 3.23E+05 | 0.0779 | 2.42E-07 | 2.0 | 3.4 | 6.6 |
| I332E/G236A | IgG(hybrid) | 5.69E+05 | 0.0235 | 4.14E-08 | 9.9 | 19.2 | 7.4 | 3.70E+05 | 0.0207 | 5.59E-08 | 8.8 | 14.8 | 7.3 |
| I332E/H268E/G236A | IgG(hybrid) | 6.44E+05 | 0.0136 | 2.12E-08 | 19.4 | 37.5 | 7.7 | 3.84E+05 | 0.0181 | 4.70E-08 | 10.5 | 17.6 | 7.3 |
| | | | | V158 FcγRIIIa | | | | | | F158 FcγRIIIa | | | |
| WT | IgG1 | 1.07E+05 | 0.0247 | 2.32E-07 | 1.0 | 1.0 | 6.6 | 1.54E+05 | 0.154 | 1.00E-06 | 1.0 | 1.0 | 6.0 |
| I332E | IgG1 | 1.81E+05 | 8.19E-03 | 4.54E-08 | 5.1 | 5.1 | 7.3 | 1.88E+05 | 0.0323 | 1.71E-07 | 5.8 | 5.8 | 6.8 |
| S239D | IgG1 | 1.70E+05 | 7.00E-03 | 4.11E-08 | 5.6 | 5.6 | 7.4 | 1.83E+05 | 3.25E-02 | 1.77E-07 | 5.6 | 5.6 | 6.8 |
| I332E/G236A | IgG1 | 1.38E+05 | 0.0111 | 8.00E-08 | 2.9 | 2.9 | 7.1 | 1.56E+05 | 0.0337 | 2.16E-07 | 4.6 | 4.6 | 6.7 |
| WT | IgG(hybrid) | 1.24E+05 | 0.0212 | 1.71E-07 | 1.0 | 1.4 | 6.8 | 1.79E+05 | 0.092 | 5.13E-07 | 1.0 | 1.9 | 6.3 |
| S239D/I332E | IgG(hybrid) | 2.59E+05 | 3.73E-03 | 1.44E-08 | 11.9 | 16.1 | 7.8 | 2.90E+05 | 1.30E-02 | 4.47E-08 | 11.5 | 22.4 | 7.3 |
| S239D/H268E | IgG(hybrid) | 2.46E+05 | 3.97E-03 | 1.61E-08 | 10.6 | 14.4 | 7.8 | 2.18E+05 | 1.36E-02 | 6.24E-08 | 8.2 | 16.0 | 7.2 |
| I332E/H268E | IgG(hybrid) | 2.20E+05 | 5.90E-03 | 2.69E-08 | 6.4 | 8.6 | 7.6 | 2.96E+05 | 2.30E-02 | 7.76E-08 | 6.6 | 12.9 | 7.1 |
| S239D/I332E/G236A | IgG(hybrid) | 2.15E+05 | 4.81E-03 | 2.24E-08 | 7.6 | 10.4 | 7.6 | 2.81E+05 | 1.28E-02 | 4.55E-08 | 11.3 | 22.0 | 7.3 |
| S239D/I332E/A330Y | IgG(hybrid) | 2.93E+05 | 3.22E-03 | 1.10E-08 | 15.5 | 21.1 | 8.0 | 3.21E+05 | 1.01E-02 | 3.15E-08 | 16.3 | 31.7 | 7.5 |
| I332E/G236A | IgG(hybrid) | 1.28E+05 | 0.0126 | 9.89E-08 | 1.7 | 2.3 | 7.0 | 1.75E+05 | 0.0325 | 1.85E-07 | 2.8 | 5.4 | 6.7 |
| I332E/H268E/G236A | IgG(hybrid) | 1.78E+05 | 8.83E-03 | 4.97E-08 | 3.4 | 4.7 | 7.3 | 2.29E+05 | 0.0271 | 1.18E-07 | 4.3 | 8.5 | 6.9 |

Figure 13a
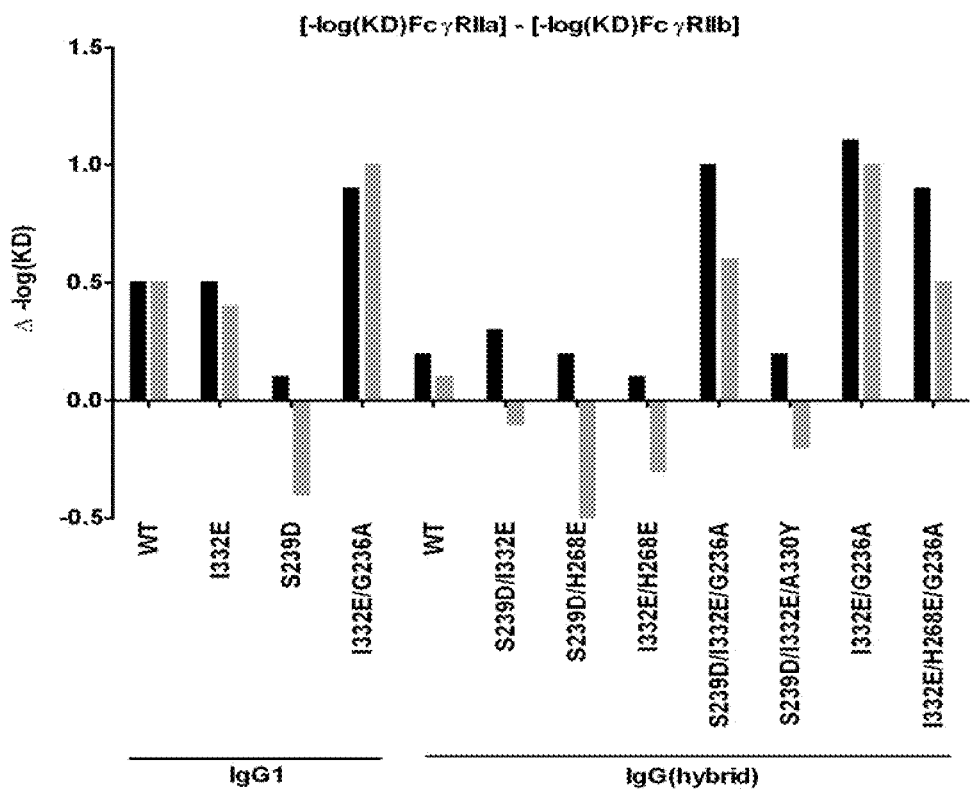
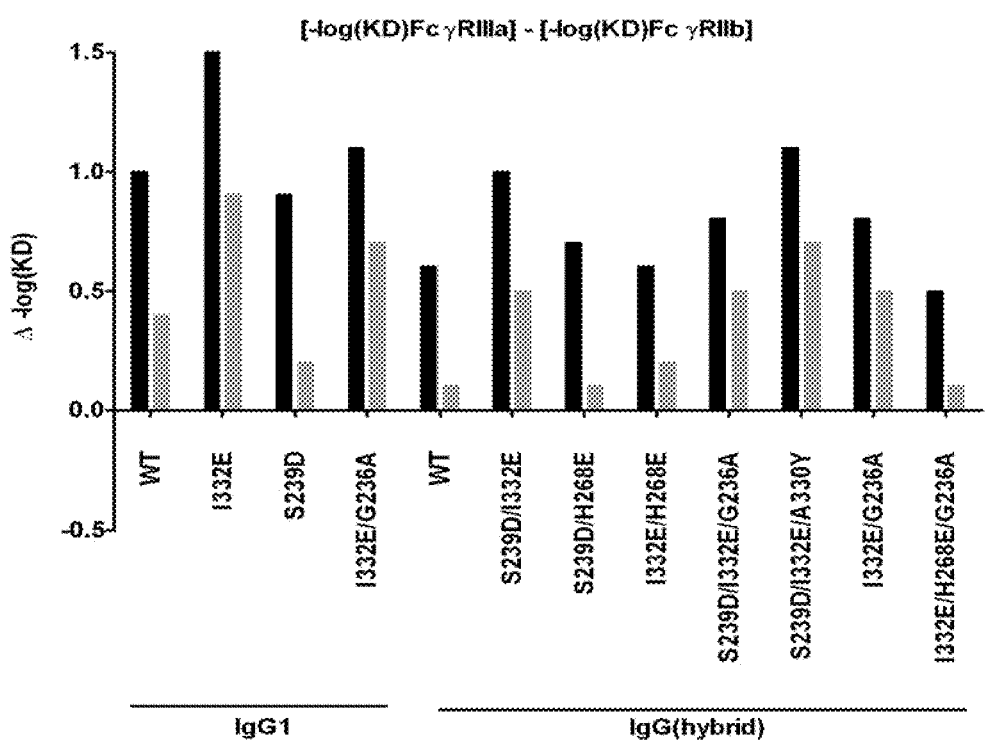

Figure 13b

| Antibody | IgG | Fold(KD)$_{RIIa}$ : Fold(KD)$_{IIb}$ | Fold(KD)$_{HIIa}$ : Fold(KD)$_{IIb}$ |
|---|---|---|---|
| WT | IgG1 | 1.0 | 1.0 |
| I332E | IgG1 | 1.0 | 0.8 |
| S239D | IgG1 | 0.4 | 0.1 |
| I332E/G236A | IgG1 | 2.6 | 3.6 |
| WT | IgG(hybrid) | 1.0 | 1.0 |
| S239D/I332E | IgG(hybrid) | 1.2 | 0.6 |
| S239D/H268E | IgG(hybrid) | 1.0 | 0.2 |
| I332E/H268E | IgG(hybrid) | 0.9 | 0.4 |
| S239D/I332E/G236A | IgG(hybrid) | 6.4 | 3.2 |
| S239D/I332E/A330Y | IgG(hybrid) | 1.0 | 0.5 |
| I332E/G236A | IgG(hybrid) | 8.7 | 7.7 |
| I332E/H268E/G236A | IgG(hybrid) | 4.7 | 2.5 |

| Antibody | IgG | Fold(KD)$_{VIIIa}$ : Fold(KD)$_{IIb}$ | Fold(KD)$_{FIIIa}$ : Fold(KD)$_{IIb}$ |
|---|---|---|---|
| WT | IgG1 | 1.0 | 1.0 |
| I332E | IgG1 | 3.2 | 3.7 |
| S239D | IgG1 | 0.7 | 0.7 |
| I332E/G236A | IgG1 | 1.2 | 1.9 |
| WT | IgG(hybrid) | 1.0 | 1.0 |
| S239D/I332E | IgG(hybrid) | 2.7 | 2.6 |
| S239D/H268E | IgG(hybrid) | 1.4 | 1.1 |
| I332E/H268E | IgG(hybrid) | 1.2 | 1.2 |
| S239D/I332E/G236A | IgG(hybrid) | 1.8 | 2.6 |
| S239D/I332E/A330Y | IgG(hybrid) | 3.5 | 3.7 |
| I332E/G236A | IgG(hybrid) | 1.5 | 2.4 |
| I332E/H268E/G236A | IgG(hybrid) | 0.8 | 1.1 |

Figure 17a
✻ PBS control
■ WT IgG1
▲ S298A
◇ S298A/E333A/K334A
● S298A/K326A/E333A/K334A
Figure 17b
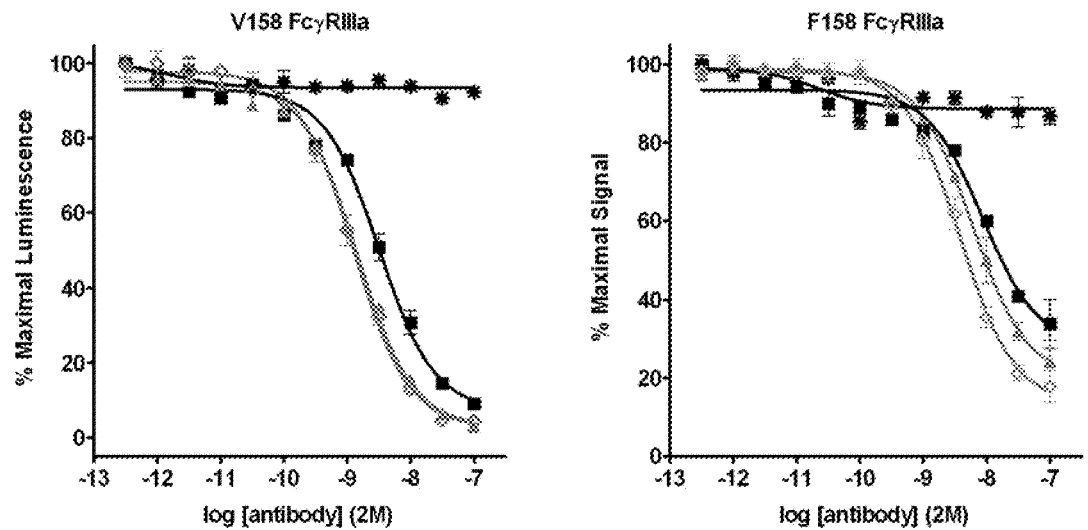
Figure 17c
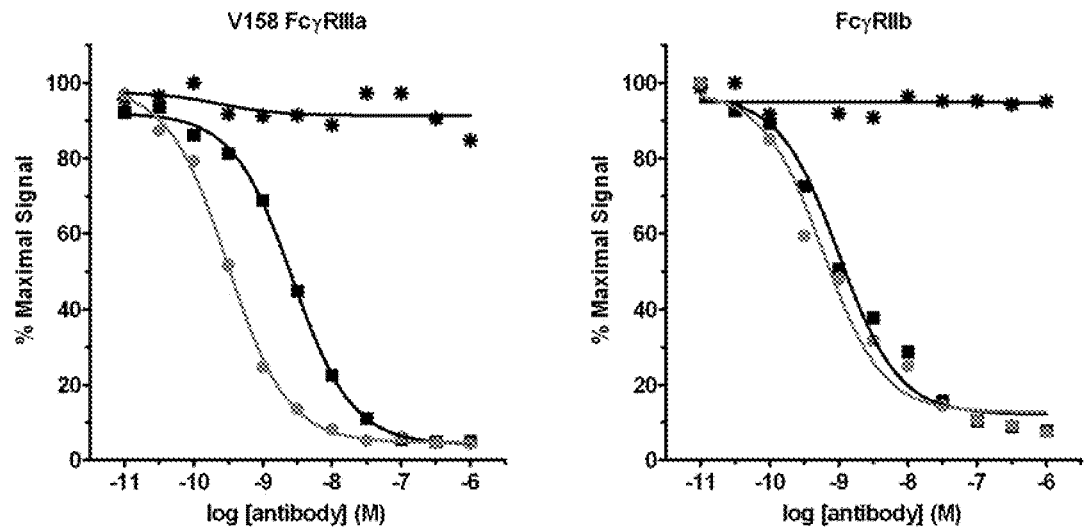

Figure 18

| Preferred positions based on structural analysis (Figure 5) | Most preferred positions | Most preferred substitutions | Alternately preferred positions | Alternately preferred substitutions |
|---|---|---|---|---|
| 235 | 234 | G I | 247 | L |
| 236 | 235 | D E I Y | 255 | L |
| 237 | 236 | A S | 270 | E |
| 238 | 239 | D | 280 | H Q Y |
| 239 | 267 | D E Q | 298 | A T |
| 265 | 268 | D E | 392 | T |
| 266 | 293 | R | 396 | L |
| 267 | 295 | E | 326 | A D E W |
| 268 | 324 | G I | 333 | A |
| 269 | 327 | H | 334 | A L |
| 270 | 328 | A F I | 421 | K |
| 295 | 330 | I L Y | | |
| 296 | 332 | D E | | |
| 298 | | | | |
| 299 | | | | |
| 325 | | | | |
| 326 | | | | |
| 327 | | | | |
| 328 | | | | |
| 329 | | | | |
| 330 | | | | |
| 332 | | | | |

Figure 19

| Antibody | IgG | Expression cell line | FcγRI KD (M) | Fold KD | -log(KD) | V158 FcγRIIIa KD (M) | Fold KD | -log(KD) |
|---|---|---|---|---|---|---|---|---|
| WT | IgG1 | 293T | 8.13E-10 | 1.0 | 9.1 | 2.63E-07 | 1.0 | 6.6 |
| WT | IgG1 | Lec13 | 7.08E-10 | 1.1 | 9.2 | 2.09E-08 | 12.6 | 7.7 |
| G236A | IgG1 | 293T | 5.75E-09 | 0.1 | 8.2 | 3.24E-07 | 0.8 | 6.5 |
| G236A | IgG1 | Lec13 | 5.50E-09 | 0.1 | 8.3 | 5.50E-08 | 4.8 | 7.3 |
| S239D/I332E | IgG(hybrid) | 293T | 3.98E-10 | 2.0 | 9.4 | 1.26E-08 | 20.9 | 7.9 |
| S239D/I332E | IgG(hybrid) | Lec13 | 3.24E-10 | 2.5 | 9.5 | 3.09E-09 | 85.1 | 8.5 |

| Antibody | IgG | Expression cell line | R131 FcγRIIa KD (M) | Fold KD | -log(KD) | H131 FcγRIIa KD (M) | Fold KD | -log(KD) | FcγRIIb KD (M) | Fold KD | -log(KD) |
|---|---|---|---|---|---|---|---|---|---|---|---|
| WT | IgG1 | 293T | 8.13E-07 | 1.0 | 6.1 | 8.13E-07 | 1.0 | 6.1 | 4.68E-06 | 1.0 | 5.3 |
| WT | IgG1 | Lec13 | 5.50E-07 | 1.5 | 6.3 | 8.51E-07 | 1.0 | 6.1 | n.d. | n.d. | n.d. |
| G236A | IgG1 | 293T | 2.14E-07 | 3.8 | 6.7 | 1.51E-07 | 5.4 | 6.8 | 1.07E-05 | 0.4 | 5.0 |
| G236A | IgG1 | Lec13 | 1.82E-07 | 4.5 | 6.7 | 1.62E-07 | 5.0 | 6.8 | 3.24E-06 | 1.4 | 5.5 |
| S239D/I332E | IgG(hybrid) | 293T | 1.05E-07 | 7.8 | 7.0 | 2.00E-07 | 4.1 | 6.7 | 1.70E-07 | 27.5 | 6.8 |
| S239D/I332E | IgG(hybrid) | Lec13 | 1.00E-07 | 8.1 | 7.0 | 2.34E-07 | 3.5 | 6.6 | 1.55E-07 | 30.2 | 6.8 |

Figure 20

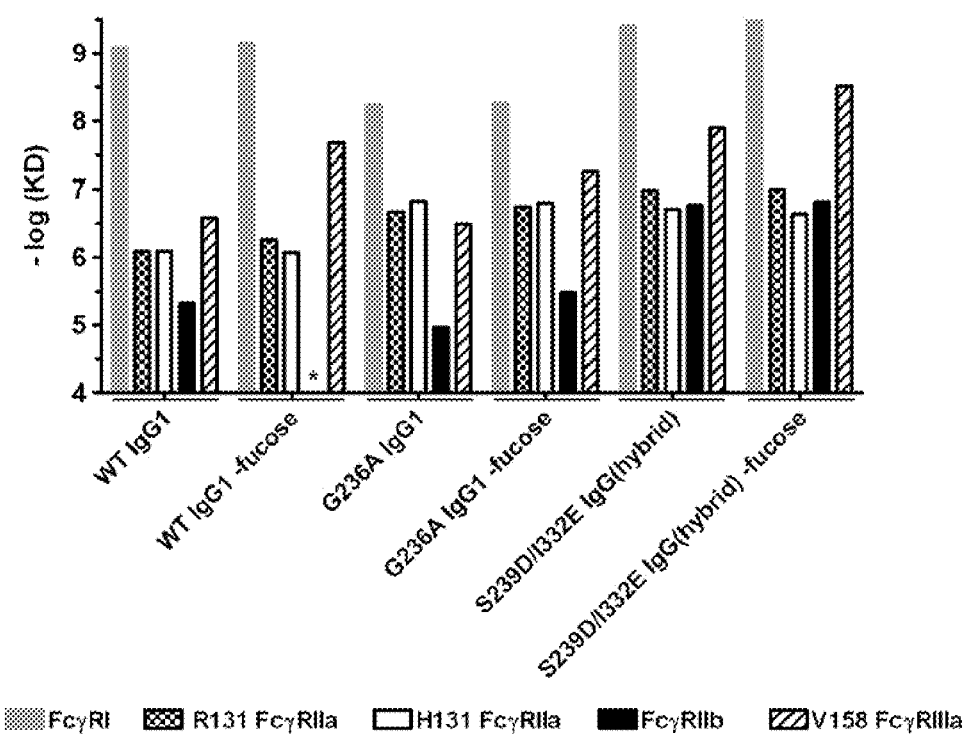

Figure 22

| Substitution(s) | FcγRIIIa Fold IC50 Relative to WT |
|---|---|
| WT | 1 |
| S239D/I332E | 36.5 |
| S239D/H268E | 28.6 |
| S239D/F241H | 0.5 |
| F241H/I332E | 1.3 |
| S239D/D265N | 0.1 |
| D265N/I332E | 0.1 |
| E233H/S239D/I332E | 2.7 |
| S239D/L234K/I332E | 10.3 |
| S239D/F241H/I332E | 2.7 |
| S239D/F241Q/I332E | 1.6 |
| S239D/F241R/I332E | |
| S239D/V264T/I332E | 11.1 |
| S239D/D265N/I332E | 0.2 |
| S239D/D265K/I332E | 0.1 |
| S239D/D265H/I332E | |
| S239D/D265Q/I332E | |
| S239D/D265G/I332E | 0 |
| S239D/D265S/I332E | 0.3 |
| S239D/D265L/I332E | |
| S239D/L328K/I332E | 0 |
| S239D/I332E/E333T | 13 |
| S239D/I332E/E333H | 39.7 |
| S239D/I332E/K334R | 19.8 |

Figure 23a

| Organism | Receptor | Gene | Signaling | Expression | | | | | |
|---|---|---|---|---|---|---|---|---|---|
| | | | | B cells | Dendritic cells | Macrophages | NK cells | Neutrophils | Mast cells |
| human | FcγRI | CD64 | activating | | yes | yes | | yes | |
| human | FcγRIIa | CD32a | activating | | yes | yes | | yes | |
| human | FcγRIIb | CD32b | inhibitory | yes | yes | yes | | | yes |
| human | FcγRIIc | CD32c | activating | yes | yes | yes | yes | yes | |
| human | FcγRIIIa | CD16a | activating | | yes | yes | yes | | yes |
| human | FcγRIIIb | CD16b | co-activating | | | | | yes | |
| mouse | FcγRI | CD64 | activating | | yes | yes | | yes | |
| mouse | FcγRIIb | CD32b | inhibitory | yes | yes | yes | | yes | yes |
| mouse | FcγRIII | CD16 | activating | | yes | yes | yes | yes | |
| mouse | FcγRIV | CD16-2, FcRL3 | activating | | yes | yes | | yes | |

Figure 23b

| | h I | h IIa | h IIb | h IIc | h IIIa | h IIIb | m I | m IIb | m III | m IV |
|---|---|---|---|---|---|---|---|---|---|---|
| h I | 100 | 41 | 42 | 42 | 43 | 44 | 62 | 42 | 42 | 43 |
| h IIa | | 100 | 93 | 91 | 49 | 50 | 38 | 62 | 60 | 49 |
| h IIb | | | 100 | 98 | 48 | 49 | 39 | 62 | 61 | 49 |
| h IIc | | | | 100 | 49 | 49 | 39 | 61 | 59 | 48 |
| h IIIa | | | | | 100 | 98 | 40 | 49 | 49 | 65 |
| h IIIb | | | | | | 100 | 41 | 49 | 49 | 64 |
| m I | | | | | | | 100 | 40 | 41 | 37 |
| m IIb | | | | | | | | 100 | 93 | 43 |
| m III | | | | | | | | | 100 | 45 |
| m IV | | | | | | | | | | 100 |

Figure 24

| Variant | Fv | CL | CH |
|---|---|---|---|
| WT | H4.40/L3.32 C225 | human Cκ | human IgG1 |
| I332E | H4.40/L3.32 C225 | human Cκ | human IgG1 |
| S239D | H4.40/L3.32 C225 | human Cκ | human IgG1 |
| H268E | H4.40/L3.32 C225 | human Cκ | human IgG1 |
| S239D/I332E | H4.40/L3.32 C225 | human Cκ | human IgG1 |
| H268E/I332E | H4.40/L3.32 C225 | human Cκ | human IgG1 |
| S239D/H268E | H4.40/L3.32 C225 | human Cκ | human IgG1 |
| S239D/I332E/H268E | H4.40/L3.32 C225 | human Cκ | human IgG1 |
| I332E/G236A | H4.40/L3.32 C225 | human Cκ | human IgG1 |
| I332E/A330Y | H4.40/L3.32 C225 | human Cκ | human IgG1 |
| WT | H4.40/L3.32 C225 | mouse Cκ | mouse IgG2a |
| I332E | H4.40/L3.32 C225 | mouse Cκ | mouse IgG2a |
| S239D | H4.40/L3.32 C225 | mouse Cκ | mouse IgG2a |
| S239D/I332E | H4.40/L3.32 C225 | mouse Cκ | mouse IgG2a |
| WT | H4.40/L3.32 C225 | mouse Cκ | mouse IgG2b |
| I332E | H4.40/L3.32 C225 | mouse Cκ | mouse IgG2b |
| S239D | H4.40/L3.32 C225 | mouse Cκ | mouse IgG2b |
| S239D/I332E | H4.40/L3.32 C225 | mouse Cκ | mouse IgG2b |
| WT | H4.40/L3.32 C225 | mouse Cκ | mouse IgG1 |
| S239D/I332E | H4.40/L3.32 C225 | mouse Cκ | mouse IgG1 |

| Substitution(s) | IgG | mouse FcγRI | | | mouse FcγRII | | | mouse FcγRIII | | | mouse FcγRIV | | |
|---|---|---|---|---|---|---|---|---|---|---|---|---|---|
| | | KD (nM) | neg log(KD) | Fold | KD (nM) | neg log(KD) | Fold | KD (nM) | neg log(KD) | Fold | KD (nM) | neg log(KD) | Fold |
| WT | human IgG1 | 216 | 6.67 | 0.3 | 859 | 6.07 | 1.7 | 72.50 | 7.14 | 7.0 | 70.9 | 7.15 | 0.1 |
| I332E | human IgG1 | 63.1 | 7.20 | 1.0 | 389 | 6.41 | 3.8 | 72.40 | 7.14 | 7.0 | 3.86 | 8.41 | 1.7 |
| H268E | human IgG1 | 115 | 6.94 | 0.5 | 363 | 6.44 | 4.0 | 75.30 | 7.12 | 6.7 | 15.1 | 7.82 | 0.4 |
| I332E/H268E | human IgG1 | 27.10 | 7.57 | 2.2 | 133 | 6.88 | 11.1 | 73.00 | 7.14 | 6.9 | 2.33 | 8.63 | 2.9 |
| S239D | human IgG1 | 89.20 | 7.05 | 0.7 | 339 | 6.47 | 4.3 | 81.20 | 7.09 | 6.2 | 5.75 | 8.24 | 1.2 |
| S239D/I332E | human IgG1 | 32.00 | 7.49 | 1.9 | 134 | 6.87 | 11.0 | 75.60 | 7.12 | 6.7 | 1.05 | 8.98 | 6.4 |
| S239D/H268E | human IgG1 | 58.10 | 7.24 | 1.0 | 185 | 6.73 | 7.9 | 83.10 | 7.08 | 6.1 | 2.69 | 8.57 | 2.5 |
| I332E/G236A | human IgG1 | 608.00 | 6.22 | 0.1 | 416 | 6.38 | 3.5 | 90.90 | 7.04 | 5.6 | 23.80 | 7.62 | 0.3 |
| I332E/A330Y | human IgG1 | 33.90 | 7.47 | 1.8 | 216 | 6.67 | 6.8 | 76.30 | 7.12 | 6.6 | 5.65 | 8.25 | 1.2 |
| WT | mouse IgG2a | 60.4 | 7.22 | 1.0 | 1470 | 5.83 | 1.0 | 505.00 | 6.30 | 1.0 | 6.75 | 8.17 | 1.0 |
| S239D/I332E | mouse IgG2a | 5.38 | 8.27 | 11.2 | 240 | 6.62 | 6.1 | 400.00 | 6.40 | 1.3 | 0.005 | 11.30 | 1350.0 |
| I332E | mouse IgG2a | 11.1 | 7.95 | 5.4 | 530 | 6.28 | 2.8 | 330.00 | 6.48 | 1.5 | 0.491 | 9.31 | 13.7 |
| WT | mouse IgG2b | unable to fit | | | 981 | 6.01 | 1.5 | 353.00 | 6.45 | 1.4 | 104 | 6.98 | 0.1 |

Figure 27a (SEQ ID NO:1)
Anti-CD20 PRO70769 variable light chain (VL)
DIQMTQSPSSLSASVGDRVTITCRASSSVSYMHWYQQKPGKAPKPLIYAPSNLASGVPSRF
SGSGSGTDFTLTISSLQPEDFATYYCQQWSFNPPTFGQGTKVEIK

Figure 27b (SEQ ID NO:2)
Anti-CD20 PRO70769 variable heavy chain (VH)
EVQLVESGGGLVQPGGSLRLSCAASGYTFTSYNMHWVRQAPGKGLEWVGAIYPGNGDTS
YNQKFKGRFTISVDKSKNTLYLQMNSLRAEDTAVYYCARVVYYSNSYWYFDVWGQGTLVT
VSS

Figure 27c (SEQ ID NO:3)
Anti-EGFR L3.32 C225 variable light chain (VL)
DIQLTQSPSSLSASVGDRVTITCRASQSISSNLHWYQQKPDQSPKLLIKYASESISGVPSRFS
GSGSGTDFTLTISSLQAEDVAVYYCQQNNNWPTTFGQGTKLEIK

Figure 27d (SEQ ID NO:4)
Anti-EGFR H4.40 C225 variable heavy chain (VH)
QVQLQQSGPGLVKPSQTLSLTCTVSGFSLSNYGVHWVRQAPGKGLEWMGIIWSGGSTDY
NTSLKSRLTISKDTSKSQVVLTMTNMDPVDTATYYCARALTYYDYEFAYWGQGTLVTVSS

Figure 27e (SEQ ID NO:5)
Anti-EpCAM L3 17-1A variable light chain (VL)
NIVMTQSPDSLAVSLGERATLSCRASENVVTYVSWYQQKPGQSPQLLIYGASNRYTGVPD
RFTGSGSATDFTLTINSLEAEDAATYYCGQGYSYPYTFGGGTKLEIK

Figure 27f (SEQ ID NO:6)
Anti-EpCAM H3.77 17-1A heavy chain (VH)
EVQLVESGGGLVQPGGSLRLSCAASGYSFTNYLIEWVRQAPGQGLEWMGVINPGSGGTN
Y
NPSLKSRVTISADKSISTAYMELSSLRSEDTAVYFCARDGPWFAYWGQGTLVTVSS

Figure 27g (SEQ ID NO:7)
Anti-CD30 L3.71 AC10 variable light chain (VL)
EIVLTQSPDSLAVSLGERATINCKASQSVDFDGDSYLNWYQQKPGQPPKVLIYAASTLQSG
VPSRFSGSGSGTDFTLTINSLEAEDAATYYCQQSNEDPWTFGGGTKVEIK

Figure 27h (SEQ ID NO:8)
Anti-CD30 H3.69_V2 AC10 variable heavy chain (VH)
QVQLVQSGAEVKKPGASVKVSCKVSGYTFTDYYITWVRQAPGQALEWMGWIYPGSGNTK
YSQKFQGRFVFSVDTSASTAYLQISSLKAEDTAVYYCANYGNYWFAYWGQGTLVTVSS

Figure 28a (SEQ ID NO:9)
Human kappa constant light chain (Cκ)
RTVAAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC

Figure 28b (SEQ ID NO:10)
Human IgG1 constant heavy chain (CH1-hinge-CH2-CH3)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSRDELTKN
QVSLTCLVKGFYPSDIAVEWESNGQPENNYKTTPPVLDSDGSFFLYSKLTVDKSRWQQGN
VFSCSVMHEALHNHYTQKSLSLSPGK

Figure 28c (SEQ ID NO:11)
Human IgG2 constant heavy chain (CH1-hinge-CH2-CH3)
ASTKGPSVFPLAPCSRSTSESTAALGCLVKDYFPEPVTVSWNSGALTSGVHTFPAVLQSSG
LYSLSSVVTVPSSNFGTQTYTCNVDHKPSNTKVDKTVERKCCVECPPCPAPPVAGPSVFLF
PPKPKDTLMISRTPEVTCVVVDVSHEDPEVQFNWYVDGVEVHNAKTKPREEQFNSTFRVV
SVLTVVHQDWLNGKEYKCKVSNKGLPAPIEKTISKTKGQPREPQVYTLPPSREEMTKNQVS
LTCLVKGFYPSDIAVEWESNGQPENNYKTTPPMLDSDGSFFLYSKLTVDKSRWQQGNVFS
CSVMHEALHNHYTQKSLSLSPGK

Figure 28d (SEQ ID NO:12)
Human IgG3 constant heavy chain (CH1-hinge-CH2-CH3)
ASTKGPSVFPLAPCSRSTSGGTAALGCLVKDYFPEPVTVSWNSGALTSGVHTFPAVLQSS
GLYSLSSVVTVPSSSLGTQTYTCNVNHKPSNTKVDKRVELKTPLGDTTHTCPRCPEPKSCD
TPPPCPRCPEPKSCDTPPPCPRCPEPKSCDTPPPCPRCPAPELLGGPSVFLFPPKPKDTL
MISRTPEVTCVVVDVSHEDPEVQFKWYVDGVEVHNAKTKPREEQYNSTFRVVSVLTVLHQ
DWLNGKEYKCKVSNKALPAPIEKTISKTKGQPREPQVYTLPPSREEMTKNQVSLTCLVKGF
YPSDIAVEWESSGQPENNYNTTPPMLDSDGSFFLYSKLTVDKSRWQQGNIFSCSVMHEAL
HNRFTQKSLSLSPGK

Figure 28e (SEQ ID NO:13)
Human IgG4 constant heavy chain (CH1-hinge-CH2-CH3)
ASTKGPSVFPLAPCSRSTSESTAALGCLVKDYFPEPVTVSWNSGALTSGVHTFPAVLQSSG
LYSLSSVVTVPSSSLGTKTYTCNVDHKPSNTKVDKRVESKYGPPCPSCPAPEFLGGPSVFL
FPPKPKDTLMISRTPEVTCVVVDVSQEDPEVQFNWYVDGVEVHNAKTKPREEQFNSTYRV
VSVLTVLHQDWLNGKEYKCKVSNKGLPSSIEKTISKAKGQPREPQVYTLPPSQEEMTKNQV
SLTCLVKGFYPSDIAVEWESNGQPENNYKTTPPVLDSDGSFFLYSRLTVDKSRWQEGNVF
SCSVMHEALHNHYTQKSLSLSLGK

Figure 28f (SEQ ID NO:14)
Human IgG(hybrid) constant heavy chain (CH1-hinge-CH2-CH3)
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVQFNWYVDGVEVHNAKTKPREEQFNSTF
RVVSVLTVVHQDWLNGKEYKCKVSNKALPAPIEKTISKTKGQPREPQVYTLPPSREEMTKN
QVSLTCLVKGFYPSDIAVEWESNGQPENNYKTTPPMLDSDGSFFLYSKLTVDKSRWQQGN
VFSCSVMHEALHNHYTQKSLSLSPGK

Figure 29a (SEQ ID NO:15)
Murine kappa constant light chain (Cκ)
RADAAPTVSIFPPSSEQLTSGGASVVCFLNNFYPKDINVKWKIDGSERQNGVLNSWTDQDS
KDSTYSMSSTLTLTKDEYERHNSYTCEATHKTSTSPIVKSFNRGEC

Figure 29b (SEQ ID NO:16)
Murine IgG1 constant heavy chain (CH1-hinge-CH2-CH3)
AKTTPPSVYPLAPGSAAQTNSMVTLGCLVKGYFPEPVTVTWNSGSLSSGVHTFPAVLQSDL
YTLSSSVTVPSSTWPSQTVTCNVAHPASSTKVDKKIVPRDCGCKPCICTVPEVSSVFIFPPK
PKDVLTITLTPKVTCVVVDISKDDPEVQFSWFVDDVEVHTAQTKPREEQFNSTFRSVSELPI
MHQDWLNGKEFKCRVNSAAFPAPIEKTISKTKGRPKAPQVYTIPPPKEQMAKDKVSLTCMIT
DFFPEDITVEWQWNGQPAENYKNTQPIMDTDGSYFVYSKLNVQKSNWEAGNTFTCSVLHE
GLHNHHTEKSLSHSPGK

Figure 29c (SEQ ID NO:17)
Murine IgG2a allele a constant heavy chain (CH1-hinge-CH2-CH3)
AKTTAPSVYPLAPVCGDTTGSSVTLGCLVKGYFPEPVTLTWNSGSLSSGVHTFPAVLQSDL
YTLSSSVTVTSSTWPSQSITCNVAHPASSTKVDKKIEPRGPTIKPCPPCKCPAPNLLGGPSV
FIFPPKIKDVLMISLSPMVTCVVVDVSEDDPDVQISWFVNNVEVLTAQTQTHREDYNSTLRV
VSALPIQHQDWMSGKEFKCKVNNKALPAPIERTISKPKGSVRAPQVYVLPPPEEEMTKKQV
TLTCMVTDFMPEDIYVEWTNNGKTELNYKNTEPVLDSDGSYFMYSKLRVEKKNWVERNSY
SCSVVHEGLHNHHTTKSFSRTPGK

Figure 29d (SEQ ID NO:18)
Murine IgG2a allele b constant heavy chain (CH1-hinge-CH2-CH3)
AKTTAPSVYPLAPVCGGTTGSSVTLGCLVKGYFPEPVTLTWNSGSLSSGVHTFPALLQSGL
YTLSSSVTVTSNTWPSQTITCNVAHPASSTKVDKKIEPRVPITQNPCPPLKECPPCAAPDLL
GGPSVFIFPPKIKDVLMISLSPMVTCVVVDVSEDDPDVQISWFVNNVEVHTAQTQTHREDY
NSTLRVVSALPIQHQDWMSGKEFKCKVNNRALPSPIEKTISKPRGPVRAPQVYVLPPPAEE
MTKKEFSLTCMITGFLPAEIAVDWTSNGRTEQNYKNTATVLDSDGSYFMYSKLRVQKSTWE
RGSLFACSVVHEGLHNHLTTKTISRSLGK

Figure 29e (SEQ ID NO:19)
Murine IgG2b constant heavy chain (CH1-hinge-CH2-CH3)
AKTTPPSVYPLAPGCGDTTGSSVTLGCLVKGYFPESVTVTWNSGSLSSSVHTFPALLQSGL
YTMSSSVTVPSSTWPSQTVTCSVAHPASSTTVDKKLEPSGPISTINPCPPCKECHKCPAPN
LEGGPSVFIFPPNIKDVLMISLTPKVTCVVVDVSEDDPDVQISWFVNNVEVHTAQTQTHRED
YNSTIRVVSALPIQHQDWMSGKEFKCKVNNKDLPSPIERTISKIKGLVRAPQVYILPPPAEQL
SRKDVSLTCLVVGFNPGDISVEWTSNGHTEENYKDTAPVLDSDGSYFIYSKLDIKTSKWEKT
DSFSCNVRHEGLKNYYLKKTISRSPGK

Figure 29f (SEQ ID NO:20)
Murine IgG3 constant heavy chain (CH1-hinge-CH2-CH3)
ATTTAPSVYPLVPGCGDTSGSSVTLGCLVKGYFPEPVTVKWNYGALSSGVRTVSSVLQSG
FYSLSSLVTVPSSTWPSQTVICNVAHPASKTELIKRIEPRIPKPSTPPGSSCPPGNILGGPSV
FIFPPKPKDALMISLTPKVTCVVVDVSEDDPDVHVSWFVDNKEVHTAWTQPREAQYNSTFR
VVSALPIQHQDWMRGKEFKCKVNNKALPAPIERTISKPKGRAQTPQVYTIPPPREQMSKKK
VSLTCLVTNFFSEAISVEWERNGELEQDYKNTPPILDSDGTYFLYSKLTVDTDSWLQGEIFT
CSVVHEALHNHHTQKNLSRSPGK

SEQUENCE LISTING

```
<160> NUMBER OF SEQ ID NOS: 30

<210> SEQ ID NO 1
<211> LENGTH: 106
<212> TYPE: PRT
<213> ORGANISM: Homo sapiens

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30
```

```
His Trp Tyr Gln Gln Lys Pro Gly Lys Ala Pro Lys Pro Leu Ile Tyr
            35                  40                  45

Ala Pro Ser Asn Leu Ala Ser Gly Val Pro Ser Arg Phe Ser Gly Ser
 50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Trp Ser Phe Asn Pro Pro Thr
                 85                  90                  95

Phe Gly Gln Gly Thr Lys Val Glu Ile Lys
            100                 105

<210> SEQ ID NO 2
<211> LENGTH: 122
<212> TYPE: PRT
<213> ORGANISM: Homo sapiens

<400> SEQUENCE: 2

Glu Val Gln Leu Val Glu Ser Gly Gly Gly Leu Val Gln Pro Gly Gly
 1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
            35                  40                  45

Gly Ala Ile Tyr Pro Gly Asn Gly Asp Thr Ser Tyr Asn Gln Lys Phe
 50                  55                  60

Lys Gly Arg Phe Thr Ile Ser Val Asp Lys Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Val Tyr Tyr Ser Asn Ser Tyr Trp Tyr Phe Asp Val Trp
            100                 105                 110

Gly Gln Gly Thr Leu Val Thr Val Ser Ser
            115                 120

<210> SEQ ID NO 3
<211> LENGTH: 107
<212> TYPE: PRT
<213> ORGANISM: Homo sapiens

<400> SEQUENCE: 3

Asp Ile Gln Leu Thr Gln Ser Pro Ser Ser Leu Ser Ala Ser Val Gly
 1               5                   10                  15

Asp Arg Val Thr Ile Thr Cys Arg Ala Ser Gln Ser Ile Ser Ser Asn
            20                  25                  30

Leu His Trp Tyr Gln Gln Lys Pro Asp Gln Ser Pro Lys Leu Leu Ile
            35                  40                  45

Lys Tyr Ala Ser Glu Ser Ile Ser Gly Val Pro Ser Arg Phe Ser Gly
 50                  55                  60

Ser Gly Ser Gly Thr Asp Phe Thr Leu Thr Ile Ser Ser Leu Gln Ala
 65                  70                  75                  80

Glu Asp Val Ala Val Tyr Tyr Cys Gln Gln Asn Asn Asn Trp Pro Thr
                 85                  90                  95

Thr Phe Gly Gln Gly Thr Lys Leu Glu Ile Lys
            100                 105

<210> SEQ ID NO 4
<211> LENGTH: 119
```

<212> TYPE: PRT
<213> ORGANISM: Homo sapiens

<400> SEQUENCE: 4

Gln Val Gln Leu Gln Gln Ser Gly Pro Gly Leu Val Lys Pro Ser Gln
1               5                   10                  15

Thr Leu Ser Leu Thr Cys Thr Val Ser Gly Phe Ser Leu Ser Asn Tyr
            20                  25                  30

Gly Val His Trp Val Arg Gln Ala Pro Gly Lys Gly Leu Glu Trp Met
        35                  40                  45

Gly Ile Ile Trp Ser Gly Gly Ser Thr Asp Tyr Asn Thr Ser Leu Lys
    50                  55                  60

Ser Arg Leu Thr Ile Ser Lys Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 5
<211> LENGTH: 107
<212> TYPE: PRT
<213> ORGANISM: Mus musculus

<400> SEQUENCE: 5

Asn Ile Val Met Thr Gln Ser Pro Asp Ser Leu Ala Val Ser Leu Gly
1               5                   10                  15

Glu Arg Ala Thr Leu Ser Cys Arg Ala Ser Glu Asn Val Val Thr Tyr
            20                  25                  30

Val Ser Trp Tyr Gln Gln Lys Pro Gly Gln Ser Pro Gln Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Asn Ser Leu Glu Ala
65                  70                  75                  80

Glu Asp Ala Ala Thr Tyr Tyr Cys Gly Gln Gly Tyr Ser Tyr Pro Tyr
                85                  90                  95

Thr Phe Gly Gly Gly Thr Lys Leu Glu Ile Lys
            100                 105

<210> SEQ ID NO 6
<211> LENGTH: 116
<212> TYPE: PRT
<213> ORGANISM: Mus musculus

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Pro Ser Leu
    50                  55                  60

Lys Ser Arg Val Thr Ile Ser Ala Asp Lys Ser Ile Ser Thr Ala Tyr

-continued

```
                65                  70                  75                  80
Met Glu Leu Ser Ser Leu Arg Ser Glu Asp Thr Ala Val Tyr Phe Cys
                    85                  90                  95

Ala Arg Asp Gly Pro Trp Phe Ala Tyr Trp Gly Gln Gly Thr Leu Val
                100                 105                 110

Thr Val Ser Ser
        115

<210> SEQ ID NO 7
<211> LENGTH: 111
<212> TYPE: PRT
<213> ORGANISM: Homo sapiens

<400> SEQUENCE: 7

Glu Ile Val Leu Thr Gln Ser Pro Asp Ser Leu Ala Val Ser Leu Gly
1               5                   10                  15

Glu Arg Ala Thr Ile Asn Cys Lys Ala Ser Gln Ser Val Asp Phe Asp
                20                  25                  30

Gly Asp Ser Tyr Leu Asn Trp Tyr Gln Gln Lys Pro Gly Gln Pro Pro
            35                  40                  45

Lys Val Leu Ile Tyr Ala Ala Ser Thr Leu Gln Ser Gly Val Pro Ser
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Thr Tyr Tyr Cys Gln Gln Ser Asn
                85                  90                  95

Glu Asp Pro Trp Thr Phe Gly Gly Gly Thr Lys Val Glu Ile Lys
                100                 105                 110

<210> SEQ ID NO 8
<211> LENGTH: 117
<212> TYPE: PRT
<213> ORGANISM: Homo sapiens

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Asp Tyr
                20                  25                  30

Tyr Ile Thr Trp Val Arg Gln Ala Pro Gly Gln Ala Leu Glu Trp Met
            35                  40                  45

Gly Trp Ile Tyr Pro Gly Ser Gly Asn Thr Lys Tyr Ser Gln Lys Phe
    50                  55                  60

Gln Gly Arg Phe Val Phe Ser Val Asp Thr Ser Ala Ser Thr Ala Tyr
65                  70                  75                  80

Leu Gln Ile Ser Ser Leu Lys Ala Glu Asp Thr Ala Val Tyr Tyr Cys
                85                  90                  95

Ala Asn Tyr Gly Asn Tyr Trp Phe Ala Tyr Trp Gly Gln Gly Thr Leu
                100                 105                 110

Val Thr Val Ser Ser
        115

<210> SEQ ID NO 9
<211> LENGTH: 107
<212> TYPE: PRT
<213> ORGANISM: Homo sapiens

<400> SEQUENCE: 9
```

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65              70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 10
<211> LENGTH: 330
<212> TYPE: PRT
<213> ORGANISM: Homo sapiens

<400> SEQUENCE: 10

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65              70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
```

```
            260                 265                 270
Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 11
<211> LENGTH: 326
<212> TYPE: PRT
<213> ORGANISM: Homo sapiens

<400> SEQUENCE: 11

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300
```

```
Ser Val Met His Glu Ala Leu His Asn His Tyr Thr Gln Lys Ser Leu
305                 310                 315                 320

Ser Leu Ser Pro Gly Lys
                325

<210> SEQ ID NO 12
<211> LENGTH: 377
<212> TYPE: PRT
<213> ORGANISM: Homo sapiens

<400> SEQUENCE: 12

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350
```

```
Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 13
<211> LENGTH: 327
<212> TYPE: PRT
<213> ORGANISM: Homo sapiens

<400> SEQUENCE: 13

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 14
<211> LENGTH: 330
<212> TYPE: PRT
<213> ORGANISM: Homo sapiens

<400> SEQUENCE: 14

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175

Glu Gln Phe Asn Ser Thr Phe Arg Val Val Ser Val Leu Thr Val Val
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Thr Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Met Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 15
<211> LENGTH: 107
<212> TYPE: PRT
<213> ORGANISM: Mus musculus

<400> SEQUENCE: 15

Arg Ala Asp Ala Ala Pro Thr Val Ser Ile Phe Pro Pro Ser Ser Glu

```
1               5                   10                  15
Gln Leu Thr Ser Gly Gly Ala Ser Val Val Cys Phe Leu Asn Asn Phe
            20                  25                  30
Tyr Pro Lys Asp Ile Asn Val Lys Trp Lys Ile Asp Gly Ser Glu Arg
            35                  40                  45
Gln Asn Gly Val Leu Asn Ser Trp Thr Asp Gln Asp Ser Lys Asp Ser
    50                  55                  60
Thr Tyr Ser Met Ser Ser Thr Leu Thr Leu Thr Lys Asp Glu Tyr Glu
65                  70                  75                  80
Arg His Asn Ser Tyr Thr Cys Glu Ala Thr His Lys Thr Ser Thr Ser
                85                  90                  95
Pro Ile Val Lys Ser Phe Asn Arg Gly Glu Cys
            100                 105

<210> SEQ ID NO 16
<211> LENGTH: 324
<212> TYPE: PRT
<213> ORGANISM: Mus musculus

<400> SEQUENCE: 16

Ala Lys Thr Thr Pro Pro Ser Val Tyr Pro Leu Ala Pro Gly Ser Ala
1               5                   10                  15
Ala Gln Thr Asn Ser Met Val Thr Leu Gly Cys Leu Val Lys Gly Tyr
            20                  25                  30
Phe Pro Glu Pro Val Thr Val Thr Trp Asn Ser Gly Ser Leu Ser Ser
            35                  40                  45
Gly Val His Thr Phe Pro Ala Val Leu Gln Ser Asp Leu Tyr Thr Leu
    50                  55                  60
Ser Ser Ser Val Thr Val Pro Ser Ser Thr Trp Pro Ser Gln Thr Val
65                  70                  75                  80
Thr Cys Asn Val Ala His Pro Ala Ser Ser Thr Lys Val Asp Lys Lys
                85                  90                  95
Ile Val Pro Arg Asp Cys Gly Cys Lys Pro Cys Ile Cys Thr Val Pro
            100                 105                 110
Glu Val Ser Ser Val Phe Ile Phe Pro Pro Lys Pro Lys Asp Val Leu
            115                 120                 125
Thr Ile Thr Leu Thr Pro Lys Val Thr Cys Val Val Val Asp Ile Ser
    130                 135                 140
Lys Asp Asp Pro Glu Val Gln Phe Ser Trp Phe Val Asp Asp Val Glu
145                 150                 155                 160
Val His Thr Ala Gln Thr Lys Pro Arg Glu Glu Gln Phe Asn Ser Thr
                165                 170                 175
Phe Arg Ser Val Ser Glu Leu Pro Ile Met His Gln Asp Trp Leu Asn
            180                 185                 190
Gly Lys Glu Phe Lys Cys Arg Val Asn Ser Ala Ala Phe Pro Ala Pro
            195                 200                 205
Ile Glu Lys Thr Ile Ser Lys Thr Lys Gly Arg Pro Lys Ala Pro Gln
    210                 215                 220
Val Tyr Thr Ile Pro Pro Pro Lys Glu Gln Met Ala Lys Asp Lys Val
225                 230                 235                 240
Ser Leu Thr Cys Met Ile Thr Asp Phe Phe Pro Glu Asp Ile Thr Val
                245                 250                 255
Glu Trp Gln Trp Asn Gly Gln Pro Ala Glu Asn Tyr Lys Asn Thr Gln
            260                 265                 270
```

```
Pro Ile Met Asp Thr Asp Gly Ser Tyr Phe Val Tyr Ser Lys Leu Asn
            275                 280                 285

Val Gln Lys Ser Asn Trp Glu Ala Gly Asn Thr Phe Thr Cys Ser Val
290                 295                 300

Leu His Glu Gly Leu His Asn His His Thr Glu Lys Ser Leu Ser His
305                 310                 315                 320

Ser Pro Gly Lys

<210> SEQ ID NO 17
<211> LENGTH: 330
<212> TYPE: PRT
<213> ORGANISM: Mus musculus

<400> SEQUENCE: 17

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Met Val Thr Cys
130                 135                 140

Val Val Val Asp Val Ser Glu Asp Asp Pro Asp Val Gln Ile Ser Trp
145                 150                 155                 160

Phe Val Asn Asn Val Glu Val Leu Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Ala Leu Pro Ala Pro Ile Glu Arg Thr Ile Ser Lys Pro Lys Gly
    210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
305                 310                 315                 320
```

-continued

```
Thr Lys Ser Phe Ser Arg Thr Pro Gly Lys
            325                 330

<210> SEQ ID NO 18
<211> LENGTH: 335
<212> TYPE: PRT
<213> ORGANISM: Mus musculus

<400> SEQUENCE: 18

Ala Lys Thr Thr Ala Pro Ser Val Tyr Pro Leu Ala Pro Val Cys Gly
  1               5                  10                  15

Gly Thr Thr Gly Ser Ser Val Thr Leu Gly Cys Leu Val Lys Gly Tyr
             20                  25                  30

Phe Pro Glu Pro Val Thr Leu Thr Trp Asn Ser Gly Ser Leu Ser Ser
         35                  40                  45

Gly Val His Thr Phe Pro Ala Leu Leu Gln Ser Gly Leu Tyr Thr Leu
     50                  55                  60

Ser Ser Ser Val Thr Val Thr Ser Asn Thr Trp Pro Ser Gln Thr Ile
 65                  70                  75                  80

Thr Cys Asn Val Ala His Pro Ala Ser Ser Thr Lys Val Asp Lys Lys
                 85                  90                  95

Ile Glu Pro Arg Val Pro Ile Thr Gln Asn Pro Cys Pro Pro Leu Lys
            100                 105                 110

Glu Cys Pro Pro Cys Ala Ala Pro Asp Leu Leu Gly Gly Pro Ser Val
        115                 120                 125

Phe Ile Phe Pro Pro Lys Ile Lys Asp Val Leu Met Ile Ser Leu Ser
    130                 135                 140

Pro Met Val Thr Cys Val Val Asp Val Ser Glu Asp Asp Pro Asp
145                 150                 155                 160

Val Gln Ile Ser Trp Phe Val Asn Asn Val Glu Val His Thr Ala Gln
                165                 170                 175

Thr Gln Thr His Arg Glu Asp Tyr Asn Ser Thr Leu Arg Val Val Ser
            180                 185                 190

Ala Leu Pro Ile Gln His Gln Asp Trp Met Ser Gly Lys Glu Phe Lys
        195                 200                 205

Cys Lys Val Asn Asn Arg Ala Leu Pro Ser Pro Ile Glu Lys Thr Ile
    210                 215                 220

Ser Lys Pro Arg Gly Pro Val Arg Ala Pro Gln Val Tyr Val Leu Pro
225                 230                 235                 240

Pro Pro Ala Glu Glu Met Thr Lys Lys Glu Phe Ser Leu Thr Cys Met
                245                 250                 255

Ile Thr Gly Phe Leu Pro Ala Glu Ile Ala Val Asp Trp Thr Ser Asn
            260                 265                 270

Gly Arg Thr Glu Gln Asn Tyr Lys Asn Thr Ala Thr Val Leu Asp Ser
        275                 280                 285

Asp Gly Ser Tyr Phe Met Tyr Ser Lys Leu Arg Val Gln Lys Ser Thr
    290                 295                 300

Trp Glu Arg Gly Ser Leu Phe Ala Cys Ser Val Val His Glu Gly Leu
305                 310                 315                 320

His Asn His Leu Thr Thr Lys Thr Ile Ser Arg Ser Leu Gly Lys
                325                 330                 335

<210> SEQ ID NO 19
<211> LENGTH: 336
<212> TYPE: PRT
<213> ORGANISM: Mus musculus
```

<400> SEQUENCE: 19

Ala Lys Thr Thr Pro Pro Ser Val Tyr Pro Leu Ala Pro Gly Cys Gly
1               5                   10                  15

Asp Thr Thr Gly Ser Ser Val Thr Leu Gly Cys Leu Val Lys Gly Tyr
            20                  25                  30

Phe Pro Glu Ser Val Thr Val Thr Trp Asn Ser Gly Ser Leu Ser Ser
        35                  40                  45

Ser Val His Thr Phe Pro Ala Leu Leu Gln Ser Gly Leu Tyr Thr Met
    50                  55                  60

Ser Ser Ser Val Thr Val Pro Ser Ser Thr Trp Pro Ser Gln Thr Val
65                  70                  75                  80

Thr Cys Ser Val Ala His Pro Ala Ser Ser Thr Thr Val Asp Lys Lys
                85                  90                  95

Leu Glu Pro Ser Gly Pro Ile Ser Thr Ile Asn Pro Cys Pro Pro Cys
            100                 105                 110

Lys Glu Cys His Lys Cys Pro Ala Pro Asn Leu Glu Gly Gly Pro Ser
        115                 120                 125

Val Phe Ile Phe Pro Pro Asn Ile Lys Asp Val Leu Met Ile Ser Leu
130                 135                 140

Thr Pro Lys Val Thr Cys Val Val Asp Val Ser Glu Asp Asp Pro
145                 150                 155                 160

Asp Val Gln Ile Ser Trp Phe Val Asn Asn Val Glu Val His Thr Ala
            165                 170                 175

Gln Thr Gln Thr His Arg Glu Asp Tyr Asn Ser Thr Ile Arg Val Val
        180                 185                 190

Ser Ala Leu Pro Ile Gln His Gln Asp Trp Met Ser Gly Lys Glu Phe
    195                 200                 205

Lys Cys Lys Val Asn Asn Lys Asp Leu Pro Ser Pro Ile Glu Arg Thr
210                 215                 220

Ile Ser Lys Ile Lys Gly Leu Val Arg Ala Pro Gln Val Tyr Ile Leu
225                 230                 235                 240

Pro Pro Pro Ala Glu Gln Leu Ser Arg Lys Asp Val Ser Leu Thr Cys
            245                 250                 255

Leu Val Val Gly Phe Asn Pro Gly Asp Ile Ser Val Glu Trp Thr Ser
        260                 265                 270

Asn Gly His Thr Glu Glu Asn Tyr Lys Asp Thr Ala Pro Val Leu Asp
    275                 280                 285

Ser Asp Gly Ser Tyr Phe Ile Tyr Ser Lys Leu Asp Ile Lys Thr Ser
290                 295                 300

Lys Trp Glu Lys Thr Asp Ser Phe Ser Cys Asn Val Arg His Glu Gly
305                 310                 315                 320

Leu Lys Asn Tyr Tyr Leu Lys Lys Thr Ile Ser Arg Ser Pro Gly Lys
            325                 330                 335

<210> SEQ ID NO 20
<211> LENGTH: 330
<212> TYPE: PRT
<213> ORGANISM: Mus musculus

<400> SEQUENCE: 20

Ala Thr Thr Thr Ala Pro Ser Val Tyr Pro Leu Val Pro Gly Cys Gly
1               5                   10                  15

Asp Thr Ser Gly Ser Ser Val Thr Leu Gly Cys Leu Val Lys Gly Tyr
            20                  25                  30

Phe Pro Glu Pro Val Thr Val Lys Trp Asn Tyr Gly Ala Leu Ser Ser
            35                  40                  45

Gly Val Arg Thr Val Ser Ser Val Leu Gln Ser Gly Phe Tyr Ser Leu
 50                  55                  60

Ser Ser Leu Val Thr Val Pro Ser Ser Thr Trp Pro Ser Gln Thr Val
 65                  70                  75                  80

Ile Cys Asn Val Ala His Pro Ala Ser Lys Thr Glu Leu Ile Lys Arg
                85                  90                  95

Ile Glu Pro Arg Ile Pro Lys Pro Ser Thr Pro Pro Gly Ser Ser Cys
            100                 105                 110

Pro Pro Gly Asn Ile Leu Gly Gly Pro Ser Val Phe Ile Phe Pro Pro
            115                 120                 125

Lys Pro Lys Asp Ala Leu Met Ile Ser Leu Thr Pro Lys Val Thr Cys
130                 135                 140

Val Val Val Asp Val Ser Glu Asp Asp Pro Asp Val His Val Ser Trp
145                 150                 155                 160

Phe Val Asp Asn Lys Glu Val His Thr Ala Trp Thr Gln Pro Arg Glu
                165                 170                 175

Ala Gln Tyr Asn Ser Thr Phe Arg Val Val Ser Ala Leu Pro Ile Gln
            180                 185                 190

His Gln Asp Trp Met Arg Gly Lys Glu Phe Lys Cys Lys Val Asn Asn
            195                 200                 205

Lys Ala Leu Pro Ala Pro Ile Glu Arg Thr Ile Ser Lys Pro Lys Gly
            210                 215                 220

Arg Ala Gln Thr Pro Gln Val Tyr Thr Ile Pro Pro Pro Arg Glu Gln
225                 230                 235                 240

Met Ser Lys Lys Lys Val Ser Leu Thr Cys Leu Val Thr Asn Phe Phe
                245                 250                 255

Ser Glu Ala Ile Ser Val Glu Trp Glu Arg Asn Gly Glu Leu Glu Gln
            260                 265                 270

Asp Tyr Lys Asn Thr Pro Pro Ile Leu Asp Ser Asp Gly Thr Tyr Phe
            275                 280                 285

Leu Tyr Ser Lys Leu Thr Val Asp Thr Asp Ser Trp Leu Gln Gly Glu
            290                 295                 300

Ile Phe Thr Cys Ser Val Val His Glu Ala Leu His Asn His His Thr
305                 310                 315                 320

Gln Lys Asn Leu Ser Arg Ser Pro Gly Lys
                325                 330

<210> SEQ ID NO 21
<211> LENGTH: 330
<212> TYPE: PRT
<213> ORGANISM: Homo sapiens

<400> SEQUENCE: 21

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Val
                20                  25                  30

Phe Pro Glu Pro Val Ile Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr

```
              65                  70                  75                  80
Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Ile Pro Glu Val Thr Cys
            130                 135                 140

Val Val Val Asp Val Ser His Glu Asp Pro Glu Val Lys Phe Asn Trp
145                 150                 155                 160

Val Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Ile Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gly Pro Glu Asn
            260                 265                 270

Asn Tyr Lys Thr Thr Pro Pro Val Leu Asp Ser Asp Gly Ser Phe Phe
            275                 280                 285

Leu Val Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 22
<211> LENGTH: 326
<212> TYPE: PRT
<213> ORGANISM: Homo sapiens

<400> SEQUENCE: 22

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Val
                20                  25                  30

Phe Pro Glu Pro Val Ile Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
                100                 105                 110
```

```
Pro Val Ala Gly Pro Ser Val Phe Leu Phe Pro Pro Lys Pro Lys Asp
            115                 120                 125

Thr Leu Met Ile Ser Arg Ile Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gly Pro Glu Asn Asn Tyr Lys Thr
            260                 265                 270

Thr Pro Pro Met Leu Asp Ser Asp Gly Ser Phe Phe Leu Val Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 23
<211> LENGTH: 377
<212> TYPE: PRT
<213> ORGANISM: Homo sapiens

<400> SEQUENCE: 23

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Val
            20                  25                  30

Phe Pro Glu Pro Val Ile Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160
```

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Val Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gly Pro Glu Asn Asn
305                 310                 315                 320

Tyr Asn Thr Thr Pro Pro Met Leu Asp Ser Asp Gly Ser Phe Phe Leu
                325                 330                 335

Val Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 24
<211> LENGTH: 326
<212> TYPE: PRT
<213> ORGANISM: Homo sapiens

<400> SEQUENCE: 24

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Val
                20                  25                  30

Phe Pro Glu Pro Val Ile Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Lys Trp Tyr Val Asp Gly

```
145                 150                 155                 160
Val Glu Tyr His Asn Ala Lys Thr Lys Pro Arg Glu Gln Phe Asn
                165                 170                 175

Ser Thr Tyr Arg Val Val Ser Val Leu Thr Val Leu His Gln Asp Trp
                180                 185                 190

Leu Asn Gly Lys Glu Tyr Lys Cys Lys Val Ser Asn Lys Gly Leu Pro
                195                 200                 205

Ser Ser Ile Glu Lys Thr Ile Ser Lys Ala Lys Gly Gln Pro Arg Glu
210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gly Pro Glu Asn Asn Tyr Lys Thr
                260                 265                 270

Thr Pro Pro Val Leu Asp Ser Asp Gly Ser Phe Phe Leu Val Ser Arg
                275                 280                 285

Leu Thr Val Asp Lys Ser Arg Trp Gln Glu Gly Asn Val Phe Ser Cys
290                 295                 300

Ser Val Met His Glu Ala Leu His Asn His Tyr Thr Gln Lys Ser Leu
305                 310                 315                 320

Ser Leu Ser Leu Gly Lys
                325

<210> SEQ ID NO 25
<211> LENGTH: 174
<212> TYPE: PRT
<213> ORGANISM: Homo sapiens

<400> SEQUENCE: 25

Gly Gln Val Asp Thr Thr Lys Ala Val Ile Thr Leu Gln Pro Pro Trp
1               5                   10                  15

Val Ser Val Phe Gln Glu Glu Thr Val Thr Leu His Cys Glu Val Leu
                20                  25                  30

His Leu Pro Gly Ser Ser Thr Gln Trp Phe Leu Asn Gly Thr Ala
            35                  40                  45

Thr Gln Thr Ser Thr Pro Ser Tyr Arg Ile Thr Ser Ala Ser Val Asn
        50                  55                  60

Asp Ser Gly Glu Tyr Arg Cys Gln Arg Gly Leu Ser Gly Arg Ser Asp
65                  70                  75                  80

Pro Ile Gln Leu Glu Ile His Arg Gly Trp Leu Leu Leu Gln Val Ser
                85                  90                  95

Ser Arg Val Phe Met Glu Gly Glu Pro Leu Ala Leu Arg Cys His Ala
                100                 105                 110

Trp Lys Asp Lys Leu Val Tyr Asn Val Leu Tyr Tyr Arg Asn Gly Lys
            115                 120                 125

Ala Phe Lys Phe Phe His Trp Asn Ser Asn Leu Thr Ile Leu Lys Thr
        130                 135                 140

Asn Ile Ser His Asn Gly Thr Tyr His Cys Ser Gly Met Gly Lys His
145                 150                 155                 160

Arg Tyr Thr Ser Ala Gly Ile Ser Gln Tyr Thr Val Lys Glu
                165                 170

<210> SEQ ID NO 26
<211> LENGTH: 176
```

```
<212> TYPE: PRT
<213> ORGANISM: Homo sapiens

<400> SEQUENCE: 26

Gln Ala Ala Pro Pro Lys Ala Val Leu Lys Leu Glu Pro Pro Trp
1               5                   10                  15

Ile Asn Val Leu Gln Glu Asp Ser Val Thr Leu Thr Cys Gln Gly Ala
                20                  25                  30

Arg Ser Pro Glu Ser Asp Ser Ile Gln Trp Phe His Asn Gly Asn Leu
            35                  40                  45

Ile Pro Thr His Thr Gln Pro Ser Tyr Arg Phe Lys Ala Asn Asn Asn
        50                  55                  60

Asp Ser Gly Glu Tyr Thr Cys Gln Thr Gly Gln Thr Ser Leu Ser Asp
65                  70                  75                  80

Pro Val His Leu Thr Val Leu Ser Glu Trp Leu Val Leu Gln Thr Pro
                85                  90                  95

His Leu Glu Phe Gln Glu Gly Glu Thr Ile Met Leu Arg Cys His Ser
                100                 105                 110

Trp Lys Asp Lys Pro Leu Val Lys Val Thr Phe Phe Gln Asn Gly Lys
            115                 120                 125

Ser Gln Lys Phe Ser His Arg Leu Asp Pro Thr Phe Ser Ile Pro Gln
        130                 135                 140

Ala Asn His Ser His Ser Gly Asp Tyr His Cys Thr Gly Asn Ile Gly
145                 150                 155                 160

Tyr Thr Leu Phe Ser Ser Lys Pro Val Thr Ile Thr Val Gln Val Pro
                165                 170                 175

<210> SEQ ID NO 27
<211> LENGTH: 175
<212> TYPE: PRT
<213> ORGANISM: Homo sapiens

<400> SEQUENCE: 27

Thr Pro Ala Ala Pro Pro Lys Ala Val Leu Lys Leu Glu Pro Gln Trp
1               5                   10                  15

Ile Asn Val Leu Gln Glu Asp Ser Val Thr Leu Thr Cys Arg Gly Thr
                20                  25                  30

His Ser Pro Glu Ser Asp Ser Ile Gln Trp Phe His Asn Gly Asn Leu
            35                  40                  45

Ile Pro Thr His Thr Gln Pro Ser Tyr Arg Phe Lys Ala Asn Asn Asn
        50                  55                  60

Asp Ser Gly Glu Tyr Thr Cys Gln Thr Gly Gln Thr Ser Leu Ser Asp
65                  70                  75                  80

Pro Val His Leu Thr Val Leu Ser Glu Trp Leu Val Leu Gln Thr Pro
                85                  90                  95

His Leu Glu Phe Gln Glu Gly Glu Thr Ile Val Leu Arg Cys His Ser
                100                 105                 110

Trp Lys Asp Lys Pro Leu Val Lys Val Thr Phe Phe Gln Asn Gly Lys
            115                 120                 125

Ser Lys Lys Phe Ser Arg Ser Asp Pro Asn Phe Ser Ile Pro Gln Ala
        130                 135                 140

Asn His Ser His Ser Gly Asp Tyr His Cys Thr Gly Asn Ile Gly Tyr
145                 150                 155                 160

Thr Leu Tyr Ser Ser Lys Pro Val Thr Ile Thr Val Gln Ala Pro
                165                 170                 175
```

```
<210> SEQ ID NO 28
<211> LENGTH: 174
<212> TYPE: PRT
<213> ORGANISM: Homo sapiens

<400> SEQUENCE: 28

Thr Pro Ala Ala Pro Lys Ala Val Leu Lys Leu Glu Pro Gln Trp
1               5                   10                  15

Ile Asn Val Leu Gln Glu Asp Ser Val Thr Leu Thr Cys Arg Gly Thr
                20                  25                  30

His Ser Pro Glu Ser Asp Ser Ile Gln Trp Phe His Asn Gly Asn Leu
            35                  40                  45

Ile Pro Thr His Thr Gln Pro Ser Tyr Arg Phe Lys Ala Asn Asn Asn
    50                  55                  60

Asp Ser Gly Glu Tyr Thr Cys Gln Thr Gly Thr Ser Leu Ser Asp
65                  70                  75                  80

Pro Val His Leu Thr Val Leu Ser Glu Trp Leu Val Leu Gln Thr Pro
                85                  90                  95

His Leu Glu Phe Gln Glu Gly Glu Thr Ile Val Leu Arg Cys His Ser
            100                 105                 110

Trp Lys Asp Lys Pro Leu Val Lys Val Thr Phe Phe Gln Asn Gly Lys
        115                 120                 125

Ser Lys Lys Phe Ser Arg Ser Asp Pro Asn Phe Ser Ile Pro Gln Ala
    130                 135                 140

Asn His Ser His Ser Gly Asp Tyr His Cys Thr Gly Asn Ile Gly Tyr
145                 150                 155                 160

Thr Leu Tyr Ser Ser Lys Pro Val Thr Ile Thr Val Gln Ala
                165                 170

<210> SEQ ID NO 29
<211> LENGTH: 176
<212> TYPE: PRT
<213> ORGANISM: Homo sapiens

<400> SEQUENCE: 29

Arg Thr Glu Asp Leu Pro Lys Ala Val Val Phe Leu Glu Pro Gln Trp
1               5                   10                  15

Tyr Arg Val Leu Glu Lys Asp Ser Val Thr Leu Lys Cys Gln Gly Ala
                20                  25                  30

Tyr Ser Pro Glu Asp Asn Ser Thr Gln Trp Phe His Asn Glu Ser Leu
            35                  40                  45

Ile Ser Ser Gln Ala Ser Ser Tyr Phe Ile Asp Ala Ala Thr Val Asp
    50                  55                  60

Asp Ser Gly Glu Tyr Arg Cys Gln Thr Asn Leu Ser Thr Leu Ser Asp
65                  70                  75                  80

Pro Val Gln Leu Glu Val His Ile Gly Trp Leu Leu Leu Gln Ala Pro
                85                  90                  95

Arg Trp Val Phe Lys Glu Glu Asp Pro Ile His Leu Arg Cys His Ser
            100                 105                 110

Trp Lys Asn Thr Ala Leu His Lys Val Thr Tyr Leu Gln Asn Gly Lys
        115                 120                 125

Gly Arg Lys Tyr Phe His His Asn Ser Asp Phe Tyr Ile Pro Lys Ala
    130                 135                 140

Thr Leu Lys Asp Ser Gly Ser Tyr Phe Cys Arg Gly Leu Val Phe Gly
145                 150                 155                 160
```

-continued

```
Ser Lys Asn Val Ser Ser Glu Thr Val Asn Ile Thr Ile Thr Gln Gly
            165                 170                 175

<210> SEQ ID NO 30
<211> LENGTH: 175
<212> TYPE: PRT
<213> ORGANISM: Homo sapiens

<400> SEQUENCE: 30

Arg Thr Glu Asp Leu Pro Lys Ala Val Val Phe Leu Glu Pro Gln Trp
1               5                   10                  15

Tyr Ser Val Leu Glu Lys Asp Ser Val Thr Leu Lys Cys Gln Gly Ala
            20                  25                  30

Tyr Ser Pro Glu Asp Asn Ser Thr Gln Trp Phe His Asn Glu Ser Leu
        35                  40                  45

Ile Ser Ser Gln Ala Ser Ser Tyr Phe Ile Asp Ala Ala Thr Val Asn
    50                  55                  60

Asp Ser Gly Glu Tyr Arg Cys Gln Thr Asn Leu Ser Thr Leu Ser Asp
65                  70                  75                  80

Pro Val Gln Leu Glu Val His Ile Gly Trp Leu Leu Leu Gln Ala Pro
                85                  90                  95

Arg Trp Val Phe Lys Glu Glu Asp Pro Ile His Leu Arg Cys His Ser
            100                 105                 110

Trp Lys Asn Thr Ala Leu His Lys Val Thr Tyr Leu Gln Asn Gly Lys
        115                 120                 125

Asp Arg Lys Tyr Phe His His Asn Ser Asp Phe His Ile Pro Lys Ala
    130                 135                 140

Thr Leu Lys Asp Ser Gly Ser Tyr Phe Cys Arg Gly Leu Val Gly Ser
145                 150                 155                 160

Lys Asn Val Ser Ser Glu Thr Val Asn Ile Thr Ile Thr Gln Gly
            165                 170                 175
```

MODIFIED FC MOLECULES

This application is a continuation of U.S. application Ser. No. 11/981,647, filed Oct. 31, 2007, now abandoned, which is a continuation of U.S. application Ser. No. 11/538,406, filed Oct. 3, 2006, now abandoned, which claims benefit under 35 U.S.C. §119(e) of U.S. Provisional Application No. 60/741,966 filed Dec. 2, 2005, U.S. Provisional Application No. 60/779,961 filed Mar. 6, 2006, U.S. Provisional Application No. 60/745,078 filed Apr. 18, 2006, U.S. Provisional Application No. 60/723,294 filed Oct. 3, 2005, U.S. Provisional Application No. 60/723,335 filed Oct. 3, 2005, U.S. Provisional Application No. 60/739,696 filed Nov. 23, 2005, U.S. Provisional Application No. 60/750,699 filed Dec. 15, 2005, U.S. Provisional Application No. 60/774,358 filed Feb. 17, 2006; this application is also a Continuation-in-Part of U.S. patent application Ser. No. 11/396,495 filed Mar. 31, 2006, now abandoned, each of which is incorporated by reference in its entirety.

FIELD OF THE INVENTION

The present invention relates to Fc variants with optimized Fc receptor binding properties, engineering methods for their generation, and their application, particularly for therapeutic purposes.

BACKGROUND OF THE INVENTION

Antibodies are immunological proteins that bind a specific antigen. Generally, antibodies are specific for targets, have the ability to mediate immune effector mechanisms, and have a long half-life in serum. Such properties make antibodies powerful therapeutics. Monoclonal antibodies are used therapeutically for the treatment of a variety of conditions including cancer, inflammation, and cardiovascular disease. There are currently over ten antibody products on the market and hundreds in development.

Antibodies have found widespread application in oncology, particularly for targeting cellular antigens selectively expressed on tumor cells with the goal of cell destruction. There are a number of mechanisms by which antibodies destroy tumor cells, including anti-proliferation via blockage of needed growth pathways, intracellular signaling leading to apoptosis, enhanced down regulation and/or turnover of receptors, CDC, ADCC, ADCP, and promotion of an adaptive immune response (Cragg et al., 1999, *Curr Opin Immunol* 11:541-547; Glennie et al., 2000, *Immunol Today* 21:403-410, both hereby entirely incorporated by reference). Antitumor efficacy may be due to a combination of these mechanisms, and their relative importance in clinical therapy appears to be cancer dependent. Despite this arsenal of anti-tumor weapons, the potency of antibodies as anti-cancer agents is unsatisfactory, particularly given their high cost. Patient tumor response data show that monoclonal antibodies provide only a small improvement in therapeutic success over normal single-agent cytotoxic chemotherapeutics. For example, just half of all relapsed low-grade non-Hodgkin's lymphoma patients respond to the anti-CD20 antibody rituximab (McLaughlin et al., 1998, *J Clin Oncol* 16:2825-2833, hereby entirely incorporated by reference). Of 166 clinical patients, 6% showed a complete response and 42% showed a partial response, with median response duration of approximately 12 months. Trastuzumab (Herceptin®, Genentech), an anti-HER2/neu antibody for treatment of metastatic breast cancer, has less efficacy. The overall response rate using trastuzumab for the 222 patients tested was only 15%, with 8 complete and 26 partial responses and a median response duration and survival of 9 to 13 months (Cobleigh et al., 1999, *J Clin Oncol* 17:2639-2648, hereby entirely incorporated by reference). Currently for anticancer therapy, any small improvement in mortality rate defines success. Thus there is a significant need to enhance the capacity of antibodies to destroy targeted cancer cells.

Because all FcγRs interact with the same binding site on Fc, and because of the high homology among the FcγRs, obtaining variants that selectively increase or reduce FcγR affinity is a major challenge. Useful variants for selectively engaging activating versus inhibitory FcγRs are not currently available. There is a need to make Fc variants that selectively increase or reduce FcγR affinity.

A challenge for development of Fc variants with optimized Fc receptor binding properties is the difference between human and murine Fc receptor biology. Fc variants are typically engineered for optimal binding to human FcγRs. Yet experiments in animal models are important for ultimately developing a drug for clinical use in humans. In particular, mouse models available for a variety of diseases are typically used to test properties such as efficacy, toxicity, and pharmacokinetics for a given drug candidate. There is a need for murine Fc variants.

These and other needs are addressed by the present invention.

SUMMARY OF THE INVENTION

In one aspect, the present invention is directed to an Fc variant of a parent Fc polypeptide comprising at least a first and a second substitution. The first and second substitutions are each at a position selected from group consisting of 234, 235, 236, 239, 267, 268, 293, 295, 324, 327, 328, 330, and 332 according to the EU index. The Fc variant exhibits an increase in affinity for one or more receptors selected from the group consisting of FcγRI, FcγRIIa, and FcγRIIIa as compared to the increase in a affinity of the Fc variant for the FcγRIIb receptor. The increases in affinities are relative to the parent polypeptide.

The present invention is further directed to methods of activating a receptor selected from the group consisting of FcγRI, FcγRIIa, and FcγRIIIa relative to the FcγRIIb receptor. A cell that includes the FcγRIIb receptor and one or more receptors selected from among FcγRI, FcγRIIa, and FcγRIIIa is contacted with an Fc variant described above. The method can be performed in vitro or in vivo.

In another aspect, the Fc variant exhibits an increase in affinity of the Fc variant for the FcγRIIb receptor as compared to the increase in affinity for one or more activating receptors. Activating receptors include FcγRI, FcγRIIa, and FcγRIIIa. Increased affinities are relative to the parent polypeptide. The first and second substitutions each at a position selected from group consisting of 234, 235, 236, 239, 267, 268, 293, 295, 324, 327, 328, 330 and 332 according to the EU index.

The present invention is further directed to methods of activating the FcγRIIb receptor relative to a receptor selected from FcγRI, FcγRIIa, and FcγRIIIa. The method is accomplished by contacting cell that includes the FcγRIIb receptor and one or more receptors selected from among FcγRI, FcγRIIa, and FcγRIIIa with an Fc variant described above. The method can be performed in vitro or in vivo.

In another aspect, the Fc variant has a reduced level of fucosylation relative to the parent Fc variant. In a variation, the Fc variant includes a glycosylated Fc region in which about 80-100% of the glycosylated Fc polypeptide in the composition having a mature core carbohydrate structure with no fucose.

The present invention also includes Fc variants of a parent mouse Fc polypeptide. In certain aspects, the Fc variant includes a substitution at a position selected from the group consisting of 236, 239, 268, 330, and 332. In further variations, the Fc variant includes a substitution selected from among 236A, 239D, 268E, 330Y, and 332E.

The present invention provides isolated nucleic acids encoding the Fc variants described herein. The present invention provides vectors comprising the nucleic acids, optionally, operably linked to control sequences. The present invention provides host cells containing the vectors, and methods for producing and optionally recovering the Fc variants.

The present invention provides novel Fc polypeptides, including antibodies, Fc fusions, isolated Fc, and Fc fragments, that comprise the Fc variants disclosed herein. The novel Fc polypeptides may find use in a therapeutic product. In certain embodiments, the Fc polypeptides of the invention are antibodies.

The present invention provides compositions comprising Fc polypeptides that comprise the Fc variants described herein, and a physiologically or pharmaceutically acceptable carrier or diluent.

The present invention contemplates therapeutic and diagnostic uses for Fc polypeptides that comprise the Fc variants disclosed herein.

BRIEF DESCRIPTION OF THE DRAWINGS

FIG. 1. FcγR-dependent effector functions and potentially relevant FcγRs for select immune cell types that may be involved in antibody-targeted tumor therapy. The third column presents interactions that may regulate activation or inhibition of the indicated cell type, with those that are thought to be particularly important highlighted in bold.

FIG. 2. Alignment of the amino acid sequences of the human IgG immunoglobulins IgG1, IgG2, IgG3, and IgG4. FIG. 2a provides the sequences of the CH1 (Cγ1) and hinge domains (SEQ ID NOS: 21-24), and FIG. 2b provides the sequences of the CH2 (Cγ2) (SEQ ID NOS: 25-28) and CH3 (Cγ3) (SEQ ID NOS: 29-32) domains. Positions are numbered according to the EU index of the IgG1 sequence, and differences between IgG1 and the other immunoglobulins IgG2, IgG3, and IgG4 are shown in gray. Allotypic polymorphisms exist at a number of positions, and thus slight differences between the presented sequences and sequences in the prior art may exist. The possible beginnings of the Fc region are labeled, defined herein as either EU position 226 or 230.

FIG. 3. Common haplotypes of the human gamma1 (FIG. 3a) and gamma2 (FIG. 3b) chains.

FIG. 4. Sequence alignment of human FcγRs. Differences from FcγRIIb are highlighted in gray, and positions at the Fc interface are indicated with an i. Numbering is shown according to both the 1IIS.pdb and 1E4K.pdb structures (SEQ ID NOS: 33-38).

FIG. 7. Summary of FcγR binding properties of anti-CD20 Fc variants for binding to human FcγRI, R131 FcγRIIa, H131 FcγRIIa, FcγRIIb, and V158 FcγRIIIa. Shown are the IC50s obtained from the AlphaScreen, and the Fold(IC50) relative to WT. Duplicate binding results, shown on separate lines, are provided for some variants.

FIG. 9. Summary of FcγR binding properties of anti-EGFR Fc variants for binding to human FcγRI, R131 FcγRIIa, H131 FcγRIIa, FcγRIIb, and V158 FcγRIIIa. Shown are the IC50s obtained from the AlphaScreen, and the Fold(IC50) relative to WT.

FIG. 11. Affinity data for binding of anti-EpCAM Fc variants to human FcγRI, R131 and H131 FcγRIIa, FcγRIIb, V158 FcγRIIIa, and F158 FcγRIIIa as determined by SPR. Provided are the association (ka) and dissociation (kd) rate constants, the equilibrium dissociation constant (KD), the Fold KD relative to WT, and the negative log of the KD (-log(KD)).

FIG. 13. Affinity differences between activating and inhibitory FcγRs for select anti-EpCAM Fc variants. FIG. 13a shows the absolute affinity differences between the activating receptors and the inhibitory receptor FcγRIIb. The top graph shows the affinity differences between both isoforms of FcγRIIa and FcγRIIb, represented mathematically as [-log(KD)FcγRIIa]-[-log(KD)FcγRIIb]. Black represents logarithmic affinity difference between R131 FcγRIIa and FcγRIIb, and gray represents the logarithmic affinity difference between H131 FcγRIIa and FcγRIIb. The bottom graph shows the affinity differences between both isoforms of FcγRIIIa and FcγRIIb, represented mathematically as [-log(KD)FcγRIIIa]-[-log(KD)FcγRIIb]. Black represents logarithmic affinity difference between V158 FcγRIIIa and FcγRIIb, and gray represents the logarithmic affinity difference between F158 FcγRIIIa and FcγRIIb. FIG. 13b provides the fold affinity improvement of each variant for FcγRIIa and FcγRIIIa relative to the fold affinity improvement to FcγRIIb. Here RIIa represents R131 FcγRIIa, HIIa represents H131 FcγRIIa, VIIIa represents V158 FcγRIIIa, FIIIa represents F158 FcγRIIIa, and IIb represents FcγRIIb. As an example, for the R131 isoform of FcγRIIa this quantity is represented mathematically as $Fold(KD)_{RIIa}:Fold(KD)_{IIb}$ or $Fold(KD)_{RIIa}/Fold(KD)_{IIb}$. See the Examples for a mathematical description of these quantities.

FIG. 14 shows the data for select Fc variant antibodies.

FIG. 15b shows the results of an ADCP assay of select anti-EpCAM Fc variants in the presence of macrophages. FIG. 15c show a repeat experiment with some of these variants.

FIG. 16. Cell-based DC activation assay of anti-EpCAM Fc variants.

FIG. 17. Binding of Fc variant antibodies comprising substitutions 298A, 326A, 333A, and 334A to human V158 FcγRIIIa, F158 FcγRIIIa, and FcγRIIb as measured by competition AlphaScreen assay. FIG. 17a shows the legend for the data. Antibodies in FIG. 17b comprise the variable region of the anti-CD52 antibody alemtuzumab (Hale et al., 1990, *Tissue Antigens* 35:118-127; Hale, 1995, *Immunotechnology* 1:175-187), and antibodies in FIG. 17c comprise the variable region of the anti-CD20 PRO70769 (PCT/US2003/040426).

FIG. 18. Preferred positions and substitutions of the invention that may be used to engineer Fc variants with selective FcγR affinity.

FIG. 19. Affinity data for binding of 293T-expressed (fucosylated) and Lec13-expressed (defucosylated) anti-EpCAM antibodies to human FcγR1, R131 and H131 FcγRIIa, FcγRIIb, and V158 FcγRIIIa as determined by SPR. Provided are the equilibrium dissociation constant (KD), the Fold KD relative to WT, and the negative log of the KD (-log(KD)). n.d.=not determined.

FIG. 20. Plot of the negative log of the KD for binding of 293T-expressed (fucosylated) and Lec13-expressed (defucosylated) anti-EpCAM antibodies to human FcγR1, R131 FcγRIIa, H131 FcγRIIa, FcγRIIb, and V158 FcγRIIIa. *=the data for binding of WT IgG1 defucosylated to FcγRIIb was not determined due to insufficiency of sample.

FIG. 22. Summary of V158 FcγRIIIa binding properties of anti-CD30 Fc variants. Shown are the Fold-IC50s relative to WT as determined by competition AlphaScreen.

FIG. 23. Differences between human and mouse FcγR biology. FIG. 23a shows the putative expression patterns of different FcγRs on various effector cell types. "yes" indicates that the receptor is expressed on that cell type. Inhibitory receptors in the human and mouse are shown in gray. FIG. 23b shows the % identity between the human (h) and mouse (m) FcγR extracellular domains. Human receptors are shown in black and mouse receptors are shown in gray.

FIG. 24. Summary of human and mouse anti-EGFR antibodies constructed. For each variant are listed the variable region (Fv), constant light chain (CL), and constant heavy chain (CH).

FIG. 27. Amino acid sequences of variable light (VL) and heavy (VH) chains used in the present invention, including PRO70769 (FIGS. 27a and 27b), H4.40/L3.32 C225 (FIGS. 27c and 27d), H3.77/L3 17-1A (FIGS. 27e and 27f), and H3.69_V2/L3.71 AC10 (FIGS. 27g and 27h) (SEQ ID NOS: 1-8).

FIG. 28. Amino acid sequences of human constant light kappa (FIG. 28a) and heavy (FIGS. 28b-28f) chains used in the present invention (SEQ ID NOS: 9-14).

FIG. 29. Amino acid sequences of mouse constant light kappa (FIG. 29a) and heavy (FIGS. 29b-29f) chains of the present invention (SEQ ID NOS: 15-20).

DETAILED DESCRIPTION OF THE INVENTION

Figure 5:
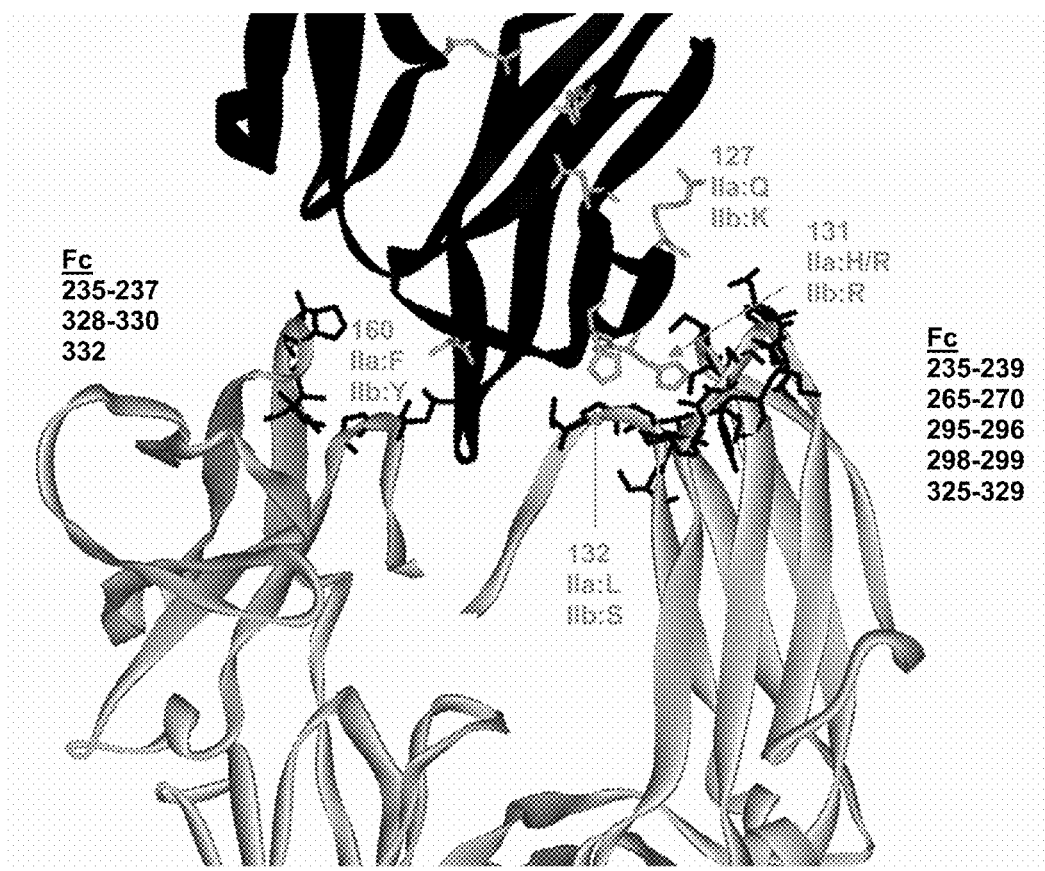
FIG. 5. Structure of the Fc/FcγR interface indicating differences between the FcγRIIa and FcγRIIb structures, and proximal Fc residues. The structure is that of the 1E4K.pdb Fc/FcγRIIIb complex. FcγR is represented by black ribbon and Fc is represented as gray ribbon. FcγR positions that differ between FcγRIIa and FcγRIIb are shown in gray, and proximal Fc residues to these FcγR residues are shown in black.

In order that the invention may be more completely understood, several definitions are set forth below. Such definitions are meant to encompass grammatical equivalents.

By "ADCC" or "antibody dependent cell-mediated cytotoxicity" as used herein is meant the cell-mediated reaction wherein nonspecific cytotoxic cells that express FcγRs recognize bound antibody on a target cell and subsequently cause lysis of the target cell.

By "ADCP" or antibody dependent cell-mediated phagocytosis as used herein is meant the cell-mediated reaction wherein nonspecific cytotoxic cells that express FcγRs recognize bound antibody on a target cell and subsequently cause phagocytosis of the target cell.

By "amino acid modification" herein is meant an amino acid substitution, insertion, and/or deletion in a polypeptide sequence. By "amino acid substitution" or "substitution" herein is meant the replacement of an amino acid at a particular position in a parent polypeptide sequence with another amino acid. For example, the substitution L328R refers to a variant polypeptide, in this case an Fc variant, in which the leucine at position 328 is replaced with arginine. By "amino acid insertion" or "insertion" as used herein is meant the addition of an amino acid at a particular position in a parent polypeptide sequence. For example, insert G>235-236 designates an insertion of glycine between positions 235 and 236. By "amino acid deletion" or "deletion" as used herein is meant the removal of an amino acid at a particular position in a parent polypeptide sequence. For example, G236-designates the deletion of glycine at position 236. Amino acids of the invention may be further classified as either isotypic or novel.

By "antibody" herein is meant a protein consisting of one or more polypeptides substantially encoded by all or part of the recognized immunoglobulin genes. The recognized immunoglobulin genes, for example in humans, include the kappa (κ), lambda (κ), and heavy chain genetic loci, which together comprise the myriad variable region genes, and the constant region genes mu (μ), delta (δ), gamma (γ), sigma (σ), and alpha (α) which encode the IgM, IgD, IgG (IgG1, IgG2, IgG3, and IgG4), IgE, and IgA (IgA1 and IgA2) isotypes respectively. Antibody herein is meant to include full length antibodies and antibody fragments, and may refer to a natural antibody from any organism, an engineered antibody, or an antibody generated recombinantly for experimental, therapeutic, or other purposes.

By "CDC" or "complement dependent cytotoxicity" as used herein is meant the reaction wherein one or more complement protein components recognize bound antibody on a target cell and subsequently cause lysis of the target cell.

By "isotypic modification" as used herein is meant an amino acid modification that converts one amino acid of one isotype to the corresponding amino acid of a different, aligned isotype. For example, because IgG1 has a tyrosine and IgG2 a phenylalanine at EU position 296, a F296Y substitution in IgG2 is considered an isotypic modification.

By "novel modification" as used herein is meant an amino acid modification that is not isotypic. For example, because none of the IgGs has a glutamic acid at position 332, the substitution I332E in IgG1, IgG2, IgG3, or IgG4 is considered a novel modification.

By "amino acid" and "amino acid identity" as used herein is meant one of the 20 naturally occurring amino acids or any non-natural analogues that may be present at a specific, defined position.

By "effector function" as used herein is meant a biochemical event that results from the interaction of an antibody Fc region with an Fc receptor or ligand. Effector functions include FcγR-mediated effector functions such as ADCC and ADCP, and complement-mediated effector functions such as CDC.

By "effector cell" as used herein is meant a cell of the immune system that expresses one or more Fc receptors and mediates one or more effector functions. Effector cells include but are not limited to monocytes, macrophages, neutrophils, dendritic cells, eosinophils, mast cells, platelets, B cells, large granular lymphocytes, Langerhans' cells, natural killer (NK) cells, and γδ T cells, and may be from any organism including but not limited to humans, mice, rats, rabbits, and monkeys.

By "Fab" or "Fab region" as used herein is meant the polypeptides that comprise the $V_H$, CH1, $V_H$, and $C_L$ immunoglobulin domains. Fab may refer to this region in isolation, or this region in the context of a full length antibody or antibody fragment.

By "Fc" or "Fc region", as used herein is meant the polypeptide comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, as illustrated in FIG. 1, Fc comprises immunoglobulin domains Cgamma2 and Cgamma3 (Cγ2 and Cγ3) and the hinge between Cgamma1 (Cγ1) and Cgamma2 (Cγ2). Although the boundaries of the Fc region may vary, the human IgG heavy chain Fc region is usually defined to comprise residues C226 or P230 to its carboxyl-terminus, wherein the numbering is according to the EU index as in Kabat. Fc may refer to this region in isolation, or this region in the context of an Fc polypeptide, as described below. By "Fc polypeptide" as used herein is meant a polypeptide that comprises all or part of an Fc region. Fc polypeptides include antibodies, Fc fusions, isolated Fcs, and Fc fragments.

By "Fc fusion" as used herein is meant a protein wherein one or more polypeptides is operably linked to Fc. Fc fusion is herein meant to be synonymous with the terms "immunoadhesin", "Ig fusion", "Ig chimera", and "receptor globulin" (sometimes with dashes) as used in the prior art (Chamow et al., 1996, *Trends Biotechnol* 14:52-60; Ashkenazi at al., 1997, *Curr Opin Immunol* 9:195-200, both hereby entirely incorporated by reference). An Fc fusion combines the Fc region of an immunoglobulin with a fusion partner, which in general may be any protein, polypeptide or small molecule. The role of the non-Fc part of an Fc fusion, i.e., the fusion partner, is to mediate target binding, and thus it is functionally analogous to the variable regions of an antibody. Virtually any protein or small molecule may be linked to Fc to generate an Fc fusion. Protein fusion partners may include, but are not limited to, the target-binding region of a receptor, an adhesion molecule, a ligand, an enzyme, a cytokine, a chemokine, or some other protein or protein domain. Small molecule fusion partners may include any therapeutic agent that directs the Fc fusion to a therapeutic target. Such targets may be any molecule, preferably an extracellular receptor that is implicated in disease.

By "Fc gamma receptor" or "FcγR" as used herein is meant any member of the family of proteins that bind the IgG antibody Fc region and are substantially encoded by the FcγR genes. In humans this family includes but is not limited to FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIIb-NA1 and FcγRIIIb-NA2) (Jefferis et al., 2002, *Immunol Lett* 82:57-65, hereby entirely incorporated by reference), as well as any undiscovered human FcγRs or FcγR isoforms or allotypes. An FcγR may be from any organism, including but not limited to humans, mice, rats, rabbits, and monkeys. Mouse FcγRs include but are not limited to FcγRI (CD64), FcγRII (CD32), FcγRIII (CD16), and FcγRIII-2 (CD16-2), as well as any undiscovered mouse FcγRs or FcγR isoforms or allotypes.

By "Fc receptor" or "Fc ligand" as used herein is meant a molecule, preferably a polypeptide, from any organism that binds to the Fc region of an antibody to form an Fc/Fc ligand complex. Fc ligands include but are not limited to FcγRs, FcγRs, FcγRs, FcRn, C1q, C3, mannan binding lectin, mannose receptor, staphylococcal protein A, streptococcal protein G, and viral FcγR. Fc ligands also include Fc receptor homologs (FcRH), which are a family of Fc receptors that are homologous to the FcγRs (Davis et al., 2002, *Immunological Reviews* 190:123-136, hereby entirely incorporated by reference). Fc ligands may include undiscovered molecules that bind Fc.

By "full length antibody" as used herein is meant the structure that constitutes the natural biological form of an antibody, including variable and constant regions. For example, in most mammals, including humans and mice, the full length antibody of the IgG isotype is a tetramer and consists of two identical pairs of two immunoglobulin chains, each pair having one light and one heavy chain, each light chain comprising immunoglobulin domains $V_L$ and $C_L$, and each heavy chain comprising immunoglobulin domains $V_H$, Cγ1, Cγ2, and Cγ3. In some mammals, for example in camels and llamas, IgG antibodies may consist of only two heavy chains, each heavy chain comprising a variable domain attached to the Fc region.

By "IgG" as used herein is meant a polypeptide belonging to the class of antibodies that are substantially encoded by a recognized immunoglobulin gamma gene. In humans this IgG comprises the subclasses or isotypes IgG1, IgG2, IgG3, and IgG4. In mice IgG comprises IgG1, IgG2a, IgG2b, IgG3.

By "immunoglobulin (Ig)" herein is meant a protein consisting of one or more polypeptides substantially encoded by immunoglobulin genes. Immunoglobulins include but are not limited to antibodies. Immunoglobulins may have a number of structural forms, including but not limited to full length antibodies, antibody fragments, and individual immunoglobulin domains.

By "immunoglobulin (Ig) domain" as used herein is meant a region of an immunoglobulin that exists as a distinct structural entity as ascertained by one skilled in the art of protein structure. Ig domains typically have a characteristic β-sandwich folding topology. The known Ig domains in the IgG isotype of antibodies are $V_H$, Cγ1, Cγ2, Cγ3, $V_L$, and $C_L$.

By "IgG" or "IgG immunoglobulin" as used herein is meant a polypeptide belonging to the class of antibodies that are substantially encoded by a recognized immunoglobulin gamma gene. In humans this class comprises the subclasses or isotypes IgG1, IgG2, IgG3, and IgG4. By "isotype" as used herein is meant any of the subclasses of immunoglobulins defined by the chemical and antigenic characteristics of their constant regions. The known human immunoglobulin isotypes are IgG1, IgG2, IgG3, IgG4, IgA1, IgA2, IgM, IgD, and IgE.

By "parent polypeptide", "parent protein", "precursor polypeptide", or "precursor protein" as used herein is meant an unmodified polypeptide that is subsequently modified to generate a variant. The parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. Accordingly, by "parent Fc polypeptide" as used herein is meant an Fc polypeptide that is modified to generate a variant, and by "parent antibody" as used herein is meant an antibody that is modified to generate a variant antibody.

By "position" as used herein is meant a location in the sequence of a protein. Positions may be numbered sequentially, or according to an established format, for example the EU index as in Kabat. For example, position 297 is a position in the human antibody IgG1.

By "polypeptide" or "protein" as used herein is meant at least two covalently attached amino acids, which includes proteins, polypeptides, oligopeptides and peptides.

By "residue" as used herein is meant a position in a protein and its associated amino acid identity. For example, Asparagine 297 (also referred to as Asn297, also referred to as N297) is a residue in the human antibody IgG1.

By "target antigen" as used herein is meant the molecule that is bound specifically by the variable region of a given antibody. A target antigen may be a protein, carbohydrate, lipid, or other chemical compound.

By "target cell" as used herein is meant a cell that expresses a target antigen.

By "variable region" as used herein is meant the region of an immunoglobulin that comprises one or more Ig domains substantially encoded by any of the Vκ, Vλ, and/or $V_H$ genes that make up the kappa, lambda, and heavy chain immunoglobulin genetic loci respectively.

By "variant polypeptide", "polypeptide variant", or "variant" as used herein is meant a polypeptide sequence that differs from that of a parent polypeptide sequence by virtue of at least one amino acid modification. The parent polypeptide may be a naturally occurring or wild-type (WT) polypeptide, or may be a modified version of a WT polypeptide. Variant polypeptide may refer to the polypeptide itself, a composition comprising the polypeptide, or the amino sequence that encodes it. Preferably, the variant polypeptide has at least one amino acid modification compared to the parent polypeptide, e.g. from about one to about ten amino acid modifications, and preferably from about one to about five amino acid modifications compared to the parent. The variant polypeptide sequence herein will preferably possess at least about 80% homology with a parent polypeptide sequence, and most preferably at least about 90% homology, more preferably at least about 95% homology. Accordingly, by "Fc variant" or "variant Fc" as used herein is meant an Fc sequence that differs from that of a parent Fc sequence by virtue of at least one amino acid modification. An Fc variant may only encompass an Fc region, or may exist in the context of an antibody, Fc fusion, isolated Fc, Fc fragment, or other polypeptide that is substantially encoded by Fc. Fc variant may refer to the Fc polypeptide itself, compositions comprising the Fc variant polypeptide, or the amino acid sequence that encodes it. By "Fc polypeptide variant" or "variant Fc polypeptide" as used herein is meant an Fc polypeptide that differs from a parent Fc polypeptide by virtue of at least one amino acid modification. By "protein variant" or "variant protein" as used herein is meant a protein that differs from a parent protein by virtue of at least one amino acid modification. By "antibody variant" or "variant antibody" as used herein is meant an antibody that differs from a parent antibody by virtue of at least one amino acid modification. By "IqG variant" or "variant IgG" as used herein is meant an antibody that differs from a parent IgG by virtue of at least one amino acid modification. By "immunoglobulin variant" or "variant immunoglobluin" as used herein is meant an immunoglobulin sequence that differs from that of a parent immunoglobulin sequence by virtue of at least one amino acid modification.

By "wild type or WT" herein is meant an amino acid sequence or a nucleotide sequence that is found in nature, including allelic variations. A WT protein, polypeptide, antibody, immunoglobulin, IgG, etc. has an amino acid sequence or a nucleotide sequence that has not been intentionally modified.

Antibodies

Antibodies are immunological proteins that bind a specific antigen. In most mammals, including humans and mice, antibodies are constructed from paired heavy and light polypeptide chains. The light and heavy chain variable regions show significant sequence diversity between antibodies, and are responsible for binding the target antigen. Each chain is made up of individual immunoglobulin (Ig) domains, and thus the generic term immunoglobulin is used for such proteins.

Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. IgA has several subclasses, including but not limited to IgA1 and IgA2. Thus, "isotype" as used herein is meant any of the subclasses of immunoglobulins defined by the chemical and antigenic characteristics of their constant regions. The known human immunoglobulin isotypes are IgG1, IgG2, IgG3, IgG4, IgA1, IgA2, IgM1, IgM2, IgD, and IgE.

Each of the light and heavy chains are made up of two distinct regions, referred to as the variable and constant regions. The IgG heavy chain is composed of four immunoglobulin domains linked from N- to C-terminus in the order $V_H$-CH1-CH2-CH3, referring to the heavy chain variable domain, heavy chain constant domain 1, heavy chain constant domain 2, and heavy chain constant domain 3 respectively (also referred to as $V_H$-Cγ1-Cγ2-Cγ3, referring to the heavy chain variable domain, constant gamma 1 domain, constant gamma 2 domain, and constant gamma 3 domain respectively). The IgG light chain is composed of two immunoglobulin domains linked from N- to C-terminus in the order $V_L$-$C_L$, referring to the light chain variable domain and the light chain constant domain respectively. The constant regions show less sequence diversity, and are responsible for binding a number of natural proteins to elicit important biochemical events. The distinguishing features between these antibody classes are their constant regions, although subtler differences may exist in the V region.

The variable region of an antibody contains the antigen binding determinants of the molecule, and thus determines the specificity of an antibody for its target antigen. The variable region is so named because it is the most distinct in sequence from other antibodies within the same class. The amino-terminal portion of each chain includes a variable region of about 100 to 110 or more amino acids primarily responsible for antigen recognition. In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant. There are 6 CDRs total, three each per heavy and light chain, designated $V_H$ CDR1, $V_H$ CDR2, $V_H$ CDR3, $V_L$ CDR1, $V_L$ CDR2, and $V_L$ CDR3. The variable region outside of the CDRs is referred to as the framework (FR) region. Although not as diverse as the CDRs, sequence variability does occur in the FR region between different antibodies. Overall, this characteristic architecture of antibodies provides a stable scaffold (the FR region) upon which substantial antigen binding diversity (the CDRs) can be explored by the immune system to obtain specificity for a broad array of antigens. A number of high-resolution structures are available for a variety of variable region fragments from different organisms, some unbound and some in complex with antigen.

Sequence and structural features of antibody variable regions are disclosed, for example, in Morea et al., 1997, *Biophys Chem* 68:9-16; Morea et al., 2000, *Methods* 20:267-279, hereby entirely incorporated by reference, and the conserved features of antibodies are disclosed, for example, in Maynard et al., 2000, *Annu Rev Biomed Eng* 2:339-376, hereby entirely incorporated by reference.

The carboxy-terminal portion of each chain defines a constant region primarily responsible for effector function. Kabat et al. collected numerous primary sequences of the variable regions of heavy chains and light chains. Based on the degree of conservation of the sequences, they classified individual primary sequences into the CDR and the framework and made a list thereof (see SEQUENCES OF IMMUNOLOGICAL INTEREST, 5th edition, NIH publication, No. 91-3242, E. A. Kabat et al.).

In the IgG subclass of immunoglobulins, there are several immunoglobulin domains in the heavy chain. By "immunoglobulin (Ig) domain" herein is meant a region of an immunoglobulin having a distinct tertiary structure. Of interest in the present invention are the heavy chain domains, including, the constant heavy (CH) domains and the hinge domains. In the context of IgG antibodies, the IgG isotypes each have three CH regions. Accordingly, "CH" domains in the context of IgG are as follows: "CH1" refers to positions 118-220 according to the EU index as in Kabat. "CH2" refers to positions 237-340 according to the EU index as in Kabat, and "CH3" refers to positions 341-447 according to the EU index as in Kabat.

Another type of Ig domain of the heavy chain is the hinge region. By "hinge" or "hinge region" or "antibody hinge region" or "immunoglobulin hinge region" herein is meant the flexible polypeptide comprising the amino acids between the first and second constant domains of an antibody. Structurally, the IgG CH1 domain ends at EU position 220, and the IgG CH2 domain begins at residue EU position 237. Thus for IgG the antibody hinge is herein defined to include positions 221 (D221 in IgG1) to 236 (G236 in IgG1), wherein the numbering is according to the EU index as in Kabat. In some embodiments, for example in the context of an Fc region, the lower hinge is included, with the "lower hinge" generally referring to positions 226 or 230.

Fc Variants

Of particular interest in the present invention are the Fc regions. By "Fc" or "Fc region", as used herein is meant the polypeptide comprising the constant region of an antibody excluding the first constant region immunoglobulin domain and in some cases, part of the hinge. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains Cgamma2 and Cgamma3 (Cγ2 and Cγ3) and the lower hinge region between Cgamma1 (Cγ1) and Cgamma2 (Cγ2). Although the boundaries of the Fc region may vary, the human IgG heavy chain Fc region is usually defined to include residues C226 or P230 to its carboxyl-terminus, wherein the numbering is according to the EU index as in Kabat. Fc may refer to this region in isolation, or this region in the context of an Fc polypeptide, as described below. By "Fc polypeptide" as used herein is meant a polypeptide that comprises all or part of an Fc region. Fc polypeptides include antibodies, Fc fusions, isolated Fcs, and Fc fragments.

An Fc variant comprises one or more amino acid modifications relative to a parent Fc polypeptide, wherein the amino acid modification(s) provide one or more optimized properties. An Fc variant of the present invention differs in amino acid sequence from its parent IgG by virtue of at least one amino acid modification. Thus Fc variants of the present invention have at least one amino acid modification compared to the parent. Alternatively, the Fc variants of the present invention may have more than one amino acid modification as compared to the parent, for example from about one to fifty amino acid modifications, preferrably from about one to ten amino acid modifications, and most preferably from about one to about five amino acid modifications compared to the parent. Thus the sequences of the Fc variants and those of the parent Fc polypeptide are substantially homologous. For example, the variant Fc variant sequences herein will possess about 80% homology with the parent Fc variant sequence, preferably at least about 90% homology, and most preferably at least about 95% homology. Modifications may be made genetically using molecular biology, or may be made enzymatically or chemically.

Figure 2B:
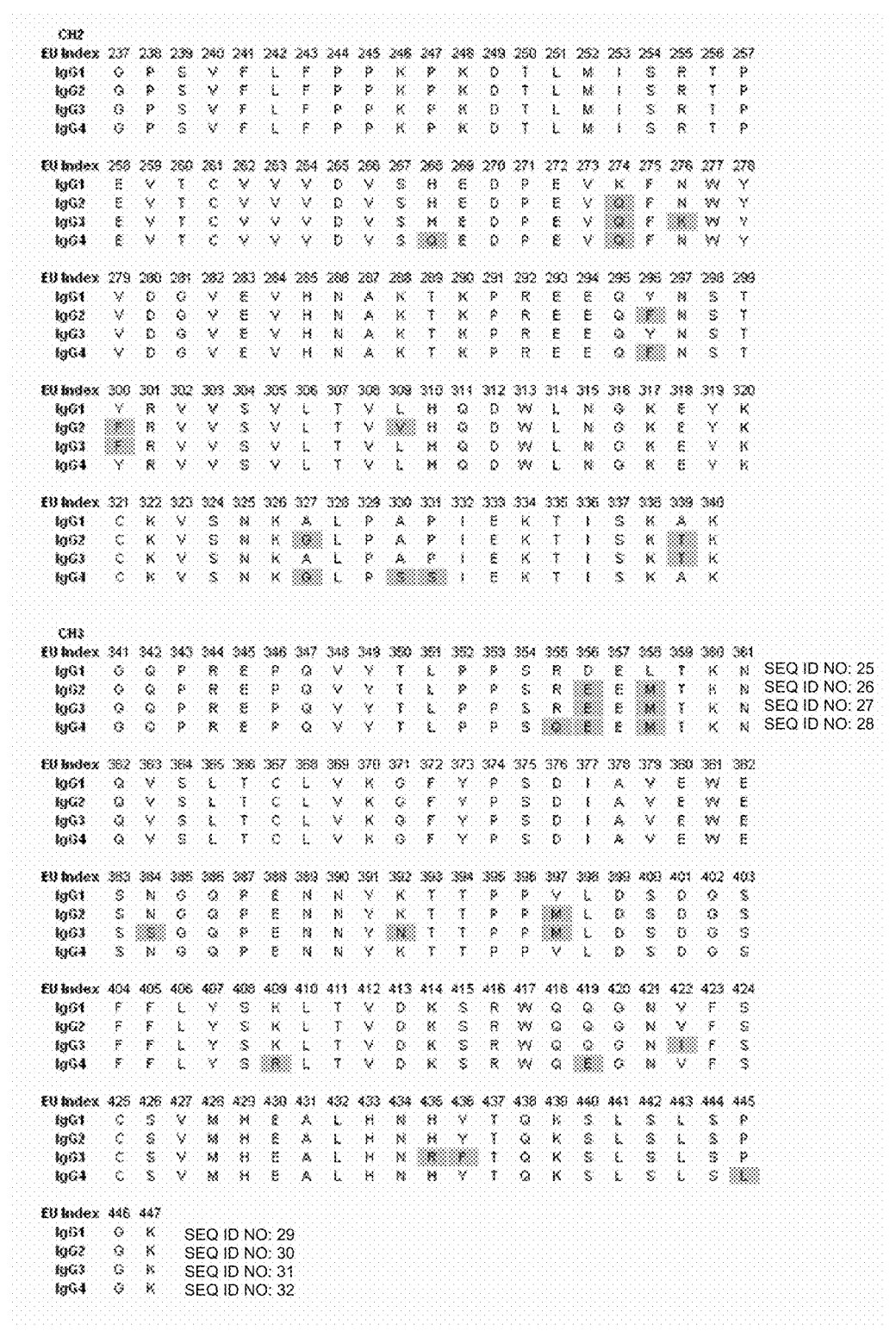

The Fc variants of the present invention may be substantially encoded by immunoglobulin genes belonging to any of the antibody classes. In certain embodiments, the Fc variants of the present invention find use in antibodies or Fc fusions that comprise sequences belonging to the IgG class of antibodies, including IgG1, IgG2, IgG3, or IgG4. FIG. 2 provides an alignment of these human IgG sequences. In an alternate embodiment the Fc variants of the present invention find use in antibodies or Fc fusions that comprise sequences belonging to the IgA (including subclasses IgA1 and IgA2), IgD, IgE, IgG, or IgM classes of antibodies. The Fc variants of the present invention may comprise more than one protein chain. That is, the present invention may find use in an antibody or Fc fusion that is a monomer or an oligomer, including a homo- or hetero-oligomer.

In certain embodiments, the Fc variants of the invention are based on human IgG sequences, and thus human IgG sequences are used as the "base" sequences against which other sequences are compared, including but not limited to sequences from other organisms, for example rodent and primate sequences. Fc variants may also comprise sequences from other immunoglobulin classes such as IgA, IgE, IgGD, IgGM, and the like. It is contemplated that, although the Fc variants of the present invention are engineered in the context of one parent IgG, the variants may be engineered in or "transferred" to the context of another, second parent IgG. This is done by determining the "equivalent" or "corresponding" residues and substitutions between the first and second IgG, typically based on sequence or structural homology between the sequences of the first and second IgGs. In order to establish homology, the amino acid sequence of a first IgG outlined herein is directly compared to the sequence of a second IgG. After aligning the sequences, using one or more of the homology alignment programs known in the art (for example using conserved residues as between species), allowing for necessary insertions and deletions in order to maintain alignment (i.e., avoiding the elimination of conserved residues through arbitrary deletion and insertion), the residues equivalent to particular amino acids in the primary sequence of the first Fc variant are defined. Alignment of conserved residues preferably should conserve 100% of such residues. However, alignment of greater than 75% or as little as 50% of conserved residues is also adequate to define equivalent residues. Equivalent residues may also be defined by determining structural homology between a first and second IgG that is at the level of tertiary structure for IgGs whose structures have been determined. In this case, equivalent residues are defined as those for which the atomic coordinates of two or more of the main chain atoms of a particular amino acid residue of the parent or precursor (N on N, CA on CA, C on C and O on O) are within about 0.13 nm and preferably about 0.1 nm after alignment. Alignment is achieved after the best model has been oriented and positioned to give the maximum overlap of atomic coordinates of non-hydrogen protein atoms of the proteins. Regardless of how equivalent or corresponding residues are determined, and regardless of the identity of the parent IgG in which the IgGs are made, what is meant to be conveyed is that the Fc variants discovered by the present invention may be engineered into any second parent IgG that has significant sequence or structural homology with the Fc variant. Thus for example, if a variant antibody is generated wherein the parent antibody is human IgG1, by using the methods described above or other methods for determining equivalent residues, the variant antibody may be engineered in another IgG1 parent antibody that binds a different antigen, a human IgG2 parent antibody, a human IgA parent antibody, a mouse IgG2a or IgG2b parent antibody, and the like. Again, as described above, the context of the parent Fc variant does not affect the ability to transfer the Fc variants of the present invention to other parent IgGs.

The Fc variants of the present invention are defined according to the amino acid modifications that compose them. Thus, for example, I332E is an Fc variant with the substitution I332E relative to the parent Fc polypeptide. Likewise, S239D/I332E/G236A defines an Fc variant with the substitutions S239D, I332E, and G236A relative to the parent Fc polypeptide. The identity of the WT amino acid may be unspecified, in which case the aforementioned variant is referred to as 239D/332E/236A. It is noted that the order in which substitutions are provided is arbitrary, that is to say that, for example, S239D/I332E/G236A is the same Fc variant as G236A/S239D/I332E, and so on. For all positions discussed in the present invention, numbering is according to the EU index or EU numbering scheme (Kabat et al., 1991, *Sequences of Proteins of Immunological Interest*, 5th Ed., United States Public Health Service, National Institutes of Health, Bethesda, hereby entirely incorporated by reference). The EU index or EU index as in Kabat or EU numbering scheme refers to the numbering of the EU antibody (Edelman et al., 1969, Proc Natl Acad Sci USA 63:78-85, hereby entirely incorporated by reference).

The Fc region of an antibody interacts with a number of Fc receptors and ligands, imparting an array of important functional capabilities referred to as effector functions. For IgG the Fc region, Fc comprises Ig domains Cγ2 and Cγ3 and the N-terminal hinge leading into Cγ2. An important family of Fc receptors for the IgG class are the Fc gamma receptors (FcγRs). These receptors mediate communication between antibodies and the cellular arm of the immune system (Raghavan et al., 1996, *Annu Rev Cell Dev Biol* 12:181-220; Ravetch et al., 2001, *Annu Rev Immunol* 19:275-290, both hereby entirely incorporated by reference). In humans this protein family includes FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIIb-NA1 and FcγRIIIb-NA2) (Jefferis et al., 2002, *Immunol Lett* 82:57-65, hereby entirely incorporated by reference). These receptors typically have an extracellular domain that mediates binding to Fc, a membrane spanning region, and an intracellular domain that may mediate some signaling event within the cell. These receptors are expressed in a variety of immune cells including monocytes, macrophages, neutrophils, dendritic cells, eosinophils, mast cells, platelets, B cells, large granular lymphocytes, Langerhans' cells, natural killer (NK) cells, and γγ T cells. Formation of the Fc/FcγR complex recruits these effector cells to sites of bound antigen, typically resulting in signaling events within the cells and important subsequent immune responses such as release of inflammation mediators, B cell activation, endocytosis, phagocytosis, and cytotoxic attack. The ability to mediate cytotoxic and phagocytic effector functions is a potential mechanism by which antibodies destroy targeted cells. The cell-mediated reaction wherein nonspecific cytotoxic cells that express FcγRs recognize bound antibody on a target cell and subsequently cause lysis of the target cell is referred to as antibody dependent cell-mediated cytotoxicity (ADCC) (Raghavan et al., 1996, *Annu Rev Cell Dev Biol* 12:181-220; Ghetie et al., 2000, *Annu Rev Immunol* 18:739-766; Ravetch et al., 2001, *Annu Rev Immunol* 19:275-290, both hereby entirely incorporated by reference). The cell-mediated reaction wherein nonspecific cytotoxic cells that express FcγRs recognize bound antibody on a target cell and subsequently cause phagocytosis of the target cell is referred to as antibody dependent cell-mediated phagocytosis (ADCP).

The different IgG subclasses have different affinities for the FcγRs, with IgG1 and IgG3 typically binding substantially better to the receptors than IgG2 and IgG4 (Jefferis et al., 2002, *Immunol Lett* 82:57-65, hereby entirely incorporated by reference). The FcγRs bind the IgG Fc region with different affinities: the high affinity binder FcγRI has a Kd for IgG1 of $10^{-8}$ $M^{-1}$, whereas the low affinity receptors FcγRII and FcγRIII generally bind at $10^{-6}$ and $10^{-5}$ respectively. The extracellular domains of FcγRIIIa and FcγRIIIb are 96% identical, however FcγRIIIb does not have a intracellular signaling domain. Furthermore, whereas FcγRI, FcγRIIa/c, and FcγRIIIa are positive regulators of immune complex-triggered activation, characterized by having an intracellular domain that has an immunoreceptor tyrosine-based activation motif (ITAM), FcγRIIb has an immunoreceptor tyrosine-based inhibition motif (ITIM) and is therefore inhibitory. Thus the former are referred to as activation receptors, and FcγRIIb is referred to as an inhibitory receptor. Despite these differences in affinities and activities, all FcγRs bind the same region on Fc, at the N-terminal end of the Cγ2 domain and the preceding hinge. This interaction is well characterized structurally (Sondermann et al., 2001, *J Mol Biol* 309:737-749, hereby entirely incorporated by reference), and several structures of the human Fc bound to the extracellular domain of human FcγRIIIb have been solved (pdb accession code 1E4K)(Sondermann et al., 2000, *Nature* 406:267-273, hereby entirely incorporated by reference) (pdb accession codes 1IIS and 1IIX)(Radaev et al., 2001, *J Biol Chem* 276:16469-16477, hereby entirely incorporated by reference).

An overlapping but separate site on Fc serves as the interface for the complement protein C1q. In the same way that Fc/FcγR binding mediates ADCC, Fc/C1q binding mediates complement dependent cytotoxicity (CDC). A site on Fc between the Cγ2 and Cγ3 domains mediates interaction with the neonatal receptor FcRn, the binding of which recycles endocytosed antibody from the endosome back to the bloodstream (Raghavan et al., 1996, *Annu Rev Cell Dev Biol* 12:181-220; Ghetie et al., 2000, *Annu Rev Immunol* 18:739-766, both hereby entirely incorporated by reference). This process, coupled with preclusion of kidney filtration due to the large size of the full length molecule, results in favorable antibody serum half-lives ranging from one to three weeks. Binding of Fc to FcRn also plays a key role in antibody transport. The binding site for FcRn on Fc is also the site at which the bacterial proteins A and G bind. The tight binding by these proteins is typically exploited as a means to purify antibodies by employing protein A or protein G affinity chromatography during protein purification. The fidelity of these regions, the complement and FcRn/proteinA binding regions are important for both the clinical properties of antibodies and their development.

A key feature of the Fc region is the conserved N-linked glycosylation that occurs at N297. This carbohydrate, or oligosaccharide as it is sometimes referred, plays a critical structural and functional role for the antibody, and is one of the principle reasons that antibodies must be produced using mammalian expression systems. Efficient Fc binding to FcγR and C1q requires this modification, and alterations in the composition of the N297 carbohydrate or its elimination affect binding to these proteins (Umaña et al., 1999, *Nat Biotechnol* 17:176-180; Davies et al., 2001, *Biotechnol Bioeng* 74:288-294; Mimura et al., 2001, *J Biol Chem* 276: 45539-45547.; Radaev et al., 2001, *J Biol Chem* 276:16478-16483; Shields et al., 2001, *J Biol Chem* 276:6591-6604; Shields et al., 2002, *J Biol Chem* 277:26733-26740; Simmons et al., 2002, *J Immunol Methods* 263:133-147, all hereby entirely incorporated by reference).

Fc variants of the present invention may be substantially encoded by genes from any organism, preferably mammals, including but not limited to humans, rodents including but not limited to mice and rats, lagomorpha including but not limited to rabbits and hares, camelidae including but not limited to camels, llamas, and dromedaries, and non-human primates, including but not limited to Prosimians, Platyrrhini (New World monkeys), Cercopithecoidea (Old World monkeys), and Hominoidea including the Gibbons and Lesser and Great Apes. In a certain embodiments, the Fc variants of the present invention are substantially human.

As is well known in the art, immunoglobulin polymorphisms exist in the human population. Gm polymorphism is determined by the IGHG1, IGHG2 and IGHG3 genes which have alleles encoding allotypic antigenic determinants referred to as G1m, G2m, and G3m allotypes for markers of the human IgG1, IgG2 and IgG3 molecules (no Gm allotypes have been found on the gamma 4 chain). Markers may be classified into 'allotypes' and 'isoallotypes'. These are distinguished on different serological bases dependent upon the strong sequence homologies between isotypes. Allotypes are antigenic determinants specified by allelic forms of the Ig genes. Allotypes represent slight differences in the amino acid sequences of heavy or light chains of different individuals. Even a single amino acid difference can give rise to an allotypic determinant, although in many cases there are several amino acid substitutions that have occurred. Allotypes are sequence differences between alleles of a subclass whereby the antisera recognize only the allelic differences. An isoallotype is an allele in one isotype which produces an epitope which is shared with a non-polymorphic homologous region of one or more other isotypes and because of this the antisera will react with both the relevant allotypes and the relevant homologous isotypes (Clark, 1997, IgG effector mechanisms, Chem Immunol. 65:88-110; Gorman & Clark, 1990, Semin Immunol 2(6):457-66, both hereby entirely incorporated by reference).

Allelic forms of human immunoglobulins have been well-characterized (WHO Review of the notation for the allotypic and related markers of human immunoglobulins. J Immunogen 1976, 3: 357-362; WHO Review of the notation for the allotypic and related markers of human immunoglobulins. 1976, Eur. J. Immunol. 6, 599-601; Loghem E van, 1986, Allotypic markers, Monogr Allergy 19: 40-51, all hereby entirely incorporated by reference). Additionally, other polymorphisms have been characterized (Kim et al., 2001, J. Mol. Evol. 54:1-9, hereby entirely incorporated by reference). At present, 18 Gm allotypes are known: G1m (1, 2, 3, 17) or G1m (a, x, f, z), G2m (23) or G2m (n), G3m (5, 6, 10, 11, 13, 14, 15, 16, 21, 24, 26, 27, 28) or G3m (b1, c3, b5, b0, b3, b4, s, t, g1, c5, u, v, g5) (Lefranc, et al., The human IgG subclasses: molecular analysis of structure, function and regulation. Pergamon, Oxford, pp. 43-78 (1990); Lefranc, G. et al., 1979, Hum. Genet.: 50, 199-211, both hereby entirely incorporated by reference). Allotypes that are inherited in fixed combinations are called Gm haplotypes. FIG. 3 shows common haplotypes of the gamma chain of human IgG1 (FIG. 3a) and IgG2 (FIG. 3b) showing the positions and the relevant amino acid substitutions. The Fc variants of the present invention may be substantially encoded by any allotype, isoallotype, or haplotype of any immunoglobulin gene.

Alternatively, the antibodies can be a variety of structures, including, but not limited to, antibody fragments, monoclonal antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and fragments of each, respectively.

Antibody Fragments, Bispecific Antibodies, and Other Immunoglobulin Formats

In one embodiment, the antibody is an antibody fragment. Of particular interest are antibodies that comprise Fc regions, Fc fusions, and the constant region of the heavy chain (CH1-hinge-CH2-CH3), again also including constant heavy region fusions.

Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, Nature 341:544-546) which consists of a single variable, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988, Science 242:423-426, Huston et al., 1988, Proc. Natl. Acad. Sci. U.S.A. 85:5879-5883), (viii) bispecific single chain Fv dimers (PCT/US92/09965) and (ix) "diabodies" or "triabodies", multivalent or multispecific fragments constructed by gene fusion (Tomlinson et. al., 2000, Methods Enzymol. 326:461-479; WO94/13804; Holliger et al., 1993, Proc. Natl. Acad. Sci. U.S.A. 90:6444-6448). The antibody fragments may be modified. For example, the molecules may be stabilized by the incorporation of disulphide bridges linking the VH and VL domains (Reiter et al., 1996, Nature Biotech. 14:1239-1245).

In one embodiment, the antibodies of the invention multispecific antibody, and notably a bispecific antibody, also sometimes referred to as "diabodies". These are antibodies that bind to two (or more) different antigens. Diabodies can be manufactured in a variety of ways known in the art (Holliger and Winter, 1993, Current Opinion Biotechnol. 4:446-449), e.g., prepared chemically or from hybrid hybridomas. In one embodiment, the antibody is a minibody. Minibodies are minimized antibody-like proteins comprising a scFv joined to a CH3 domain. Hu et al., 1996, Cancer Res. 56:3055-3061. In some cases, the scFv can be joined to the Fc region, and may include some or all of the hinge region.

Chimeric, Humanized, and Fully Human Antibodies

In some embodiments, the scaffold components can be a mixture from different species. As such, if the antibody is an antibody, such antibody may be a chimeric antibody and/or a humanized antibody. In general, both "chimeric antibodies" and "humanized antibodies" refer to antibodies that combine regions from more than one species. For example, "chimeric antibodies" traditionally comprise variable region(s) from a mouse (or rat, in some cases) and the constant region(s) from a human. "Humanized antibodies" generally refer to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321:522-525, Verhoeyen et al., 1988, Science 239: 1534-1536. "Backmutation" of selected acceptor framework residues to the corresponding donor residues is often required to regain affinity that is lost in the initial grafted construct (U.S. Pat. No. 5,530,101; U.S. Pat. No. 5,585,089; U.S. Pat. No. 5,693,761; U.S. Pat. No. 5,693,762; U.S. Pat. No. 6,180,370; U.S. Pat. No. 5,859,205; U.S. Pat. No. 5,821,337; U.S. Pat. No. 6,054,297; U.S. Pat. No. 6,407,213). The humanized antibody optimally also will comprise at least a portion of an immunoglobulin constant region, typically that of a human immunoglobulin, and thus will typically comprise a human Fc region. Humanized antibodies can also be generated using mice with a genetically engineered immune system. Roque et al., 2004, Biotechnol. Prog. 20:639-654. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein). Humanization methods include but are not limited to methods described in Jones et al., 1986, *Nature* 321:522-525; Riechmann et al., 1988; *Nature* 332:323-329; Verhoeyen et al., 1988, *Science*, 239: 1534-1536; Queen et al., 1989, *Proc Natl Acad Sci, USA* 86:10029-33; He et al., 1998, J. Immunol. 160: 1029-1035; Carter et al., 1992, *Proc Natl Acad Sci USA* 89:4285-9, Presta et al., 1997, Cancer Res.57(20):4593-9; Gorman et al., 1991, Proc. Natl. Acad. Sci. USA 88:4181-4185; O'Connor et al., 1998, *Protein Eng* 11:321-8. Humanization or other methods of reducing the immunogenicity of nonhuman antibody variable regions may include resurfacing methods, as described for example in Roguska et al., 1994, Proc. Natl. Acad. Sci. USA 91:969-973. In one embodiment, the parent antibody has been affinity matured, as is known in the art. Structure-based methods may be employed for humanization and affinity maturation, for example as described in U.S. Ser. No. 11/004,590. Selection based methods may be employed to humanize and/or affinity mature antibody variable regions, including but not limited to methods described in Wu et al., 1999, J. Mol. Biol. 294:151-162; Baca et al., 1997, J. Biol. Chem. 272(16):10678-10684; Rosok et al., 1996, J. Biol. Chem. 271(37): 22611-22618; Rader et al., 1998, Proc. Natl. Acad. Sci. USA 95: 8910-8915; Krauss et al., 2003, Protein Engineering 16(10):753-759. Other humanization methods may involve the grafting of only parts of the CDRs, including but not limited to methods described in U.S. Ser. No. 09/810, 502; Tan et al., 2002, J. Immunol. 169:1119-1125; De Pascalis et al., 2002, J. Immunol. 169:3076-3084.

In one embodiment, the antibody is a fully human antibody with at least one modification as outlined herein. "Fully human antibody" or "complete human antibody" refers to a human antibody having the gene sequence of an antibody derived from a human chromosome with the modifications outlined herein. Fully human antibodies may be obtained, for example, using transgenic mice (Bruggemann et al., 1997, *Curr Opin Biotechnol* 8:455-458) or human antibody libraries coupled with selection methods (Griffiths et al., 1998, *Curr Opin Biotechnol* 9:102-108).

Antibody Fusions

In one embodiment, the antibodies of the invention are antibody fusion proteins (sometimes referred to herein as an "antibody conjugate"). One type of antibody fusions are Fc fusions, which join the Fc region with a conjugate partner. By "Fc fusion" as used herein is meant a protein wherein one or more polypeptides is operably linked to an Fc region. Fc fusion is herein meant to be synonymous with the terms "immunoadhesin", "Ig fusion", "Ig chimera", and "receptor globulin" (sometimes with dashes) as used in the prior art (Chamow et al., 1996, Trends Biotechnol 14:52-60; Ashkenazi et al., 1997, Curr Opin Immunol 9:195-200). An Fc fusion combines the Fc region of an immunoglobulin with a fusion partner, which in general can be any protein or small molecule. Virtually any protein or small molecule may be linked to Fc to generate an Fc fusion. Protein fusion partners may include, but are not limited to, the variable region of any antibody, the target-binding region of a receptor, an adhesion molecule, a ligand, an enzyme, a cytokine, a chemokine, or some other protein or protein domain. Small molecule fusion partners may include any therapeutic agent that directs the Fc fusion to a therapeutic target. Such targets may be any molecule, preferably an extracellular receptor, that is implicated in disease.

In addition to antibodies, an antibody-like protein that is finding an expanding role in research and therapy is the Fc fusion (Chamow et al., 1996, *Trends Biotechnol* 14:52-60; Ashkenazi et al., 1997, *Curr Opin Immunol* 9:195-200, both hereby entirely incorporated by reference). An Fc fusion is a protein wherein one or more polypeptides is operably linked to Fc. An Fc fusion combines the Fc region of an antibody, and thus its favorable effector functions and pharmacokinetics, with the target-binding region of a receptor, ligand, or some other protein or protein domain. The role of the latter is to mediate target recognition, and thus it is functionally analogous to the antibody variable region. Because of the structural and functional overlap of Fc fusions with antibodies, the discussion on antibodies in the present invention extends also to Fc fusions.

In addition to Fc fusions, antibody fusions include the fusion of the constant region of the heavy chain with one or more fusion partners (again including the variable region of any antibody), while other antibody fusions are substantially or completely full length antibodies with fusion partners. In one embodiment, a role of the fusion partner is to mediate target binding, and thus it is functionally analogous to the variable regions of an antibody (and in fact can be). Virtually any protein or small molecule may be linked to Fc to generate an Fc fusion (or antibody fusion). Protein fusion partners may include, but are not limited to, the target-binding region of a receptor, an adhesion molecule, a ligand, an enzyme, a cytokine, a chemokine, or some other protein or protein domain. Small molecule fusion partners may include any therapeutic agent that directs the Fc fusion to a therapeutic target. Such targets may be any molecule, preferably an extracellular receptor, that is implicated in disease.

The conjugate partner can be proteinaceous or non-proteinaceous; the latter generally being generated using functional groups on the antibody and on the conjugate partner. For example linkers are known in the art; for example, homo- or hetero-bifunctional linkers as are well known (see, 1994 Pierce Chemical Company catalog, technical section on cross-linkers, pages 155-200, incorporated herein by reference).

Suitable conjugates include, but are not limited to, labels as described below, drugs and cytotoxic agents including, but not limited to, cytotoxic drugs (e.g., chemotherapeutic agents) or toxins or active fragments of such toxins. Suitable toxins and their corresponding fragments include diptheria A chain, exotoxin A chain, ricin A chain, abrin A chain, curcin, crotin, phenomycin, enomycin and the like. Cytotoxic agents also include radiochemicals made by conjugating radioisotopes to antibodies, or binding of a radionuclide to a chelating agent that has been covalently attached to the antibody. Additional embodiments utilize calicheamicin, auristatins, geldanamycin, maytansine, and duocarmycins and analogs; for the latter, see U.S. 2003/0050331, hereby incorporated by reference in its entirety.

Covalent Modifications of Antibodies

Covalent modifications of antibodies are included within the scope of this invention, and are generally, but not always, done post-translationally. For example, several types of covalent modifications of the antibody are introduced into the molecule by reacting specific amino acid residues of the antibody with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using 125I or 131I to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are optionally different alkyl groups, such as 1-cyclohexyl-3-(2-morpholinyl-4-ethyl)carbodiimide or 1-ethyl-3-(4-azonia-4,4-dimethylpentyl)carbodiimide. Furthermore, aspartyl and glutamyl residues are converted to asparaginyl and glutaminyl residues by reaction with ammonium ions.

Derivatization with bifunctional agents is useful for crosslinking antibodies to a water-insoluble support matrix or surface for use in a variety of methods, in addition to methods described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W. H. Freeman & Co., San Francisco, pp. 79-86 [1983]), acetylation of the N-terminal amine, and amidation of any C-terminal carboxyl group.

Another type of covalent modification of the antibody comprises linking the antibody to various nonproteinaceous polymers, including, but not limited to, various polyols such as polyethylene glycol, polypropylene glycol or polyoxyalkylenes, in the manner set forth in U.S. Pat. No. 4,640,835; 4,496,689; 4,301,144; 4,670,417; 4,791,192 or 4,179,337. In addition, as is known in the art, amino acid substitutions may be made in various positions within the antibody to facilitate the addition of polymers such as PEG. See for example, U.S. Publication No. 2005/0114037, incorporated herein by reference in its entirety.

Labeled Antibodies

In some embodiments, the covalent modification of the antibodies of the invention comprises the addition of one or more labels. In some cases, these are considered antibody fusions.

The term "labelling group" means any detectable label. In some embodiments, the labelling group is coupled to the antibody via spacer arms of various lengths to reduce potential steric hindrance. Various methods for labelling proteins are known in the art and may be used in performing the present invention.

In general, labels fall into a variety of classes, depending on the assay in which they are to be detected: a) isotopic labels, which may be radioactive or heavy isotopes; b) magnetic labels (e.g., magnetic particles); c) redox active moieties; d) optical dyes; enzymatic groups (e.g. horseradish peroxidase, β-galactosidase, luciferase, alkaline phosphatase); e) biotinylated groups; and f) predetermined polypeptide epitopes recognized by a secondary reporter (e.g., leucine zipper pair sequences, binding sites for secondary antibodies, metal binding domains, epitope tags, etc.). In some embodiments, the labelling group is coupled to the antibody via spacer arms of various lengths to reduce potential steric hindrance. Various methods for labelling proteins are known in the art and may be used in performing the present invention.

Specific labels include optical dyes, including, but not limited to, chromophores, phosphors and fluorophores, with the latter being specific in many instances. Fluorophores can be either "small molecule" fluores, or proteinaceous fluores.

By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade BlueJ, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes, Eugene, Oreg.), FITC, Rhodamine, and Texas Red (Pierce, Rockford, Ill.), Cy5, Cy5.5, Cy7 (Amersham Life Science, Pittsburgh, Pa.). Suitable optical dyes, including fluorophores, are described in Molecular Probes Handbook by Richard P. Haugland, hereby expressly incorporated by reference.

Suitable proteinaceous fluorescent labels also include, but are not limited to, green fluorescent protein, including a *Renilla, Ptilosarcus,* or *Aequorea* species of GFP (Chalfie et al., 1994, Science 263:802-805), EGFP (Clontech Laboratories, Inc., Genbank Accession Number U55762), blue fluorescent protein (BFP, Quantum Biotechnologies, Inc. 1801 de Maisonneuve Blvd. West, 8th Floor, Montreal, Quebec, Canada H3H 1J9; Stauber, 1998, Biotechniques 24:462-471; Heim et al., 1996, Curr. Biol. 6:178-182), enhanced yellow fluorescent protein (EYFP, Clontech Laboratories, Inc.), luciferase (Ichiki et al., 1993, J. Immunol. 150:5408-5417), β galactosidase (Nolan et al., 1988, Proc. Natl. Acad. Sci. U.S.A. 85:2603-2607) and *Renilla* (WO92/15673, WO95/07463, WO98/14605, WO98/26277, WO99/49019, U.S. Pat. Nos. 5,292,658, 5,418,155, 5,683,888, 5,741,668, 5,777,079, 5,804,387, 5,874,304, 5,876,995, 5,925,558). All of the above-cited references are expressly incorporated herein by reference.

Targets

Virtually any antigen may be targeted by the Fc variants of the present invention, including but not limited to proteins, subunits, domains, motifs, and/or epitopes belonging to the following list of targets: 17-IA, 4-1BB, 4Dc, 6-keto-PGF1a, 8-iso-PGF2a, 8-oxo-dG, A1 Adenosine Receptor, A33, ACE, ACE-2, Activin, Activin A, Activin AB, Activin B, Activin C, Activin RIA, Activin RIA ALK-2, Activin RIB ALK-4, Activin RIIA, Activin RIIB, ADAM, ADAM10, ADAM12, ADAM15, ADAM17/TACE, ADAM8, ADAM9, ADAMTS, ADAMTS4, ADAMTS5, Addressins, aFGF, ALCAM, ALK, ALK-1, ALK-7, alpha-1-antitrypsin, alpha-V/beta-1 antagonist, ANG, Ang, APAF-1, APE, APJ, APP, APRIL, AR, ARC, ART, Artemin, anti-Id, ASPARTIC, Atrial natriuretic factor, av/b3 integrin, Axl, b2M, B7-1, B7-2, B7-H, B-lymphocyte Stimulator (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMPs, b-NGF, BOK, Bombesin, Bone-derived neurotrophic factor, BPDE, BPDE-DNA, BTC, complement factor 3 (C3), C3a, C4, C5, C5a, C10, CA125, CAD-8, Calcitonin, cAMP, carcinoembryonic antigen (CEA), carcinoma-associated antigen, Cathepsin A, Cathepsin B, Cathepsin C/DPPI, Cathepsin D, Cathepsin E, Cathepsin H, Cathepsin L, Cathepsin O, Cathepsin S, Cathepsin V, Cathepsin X/Z/P, CBL, CCl, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 proteins), CD34, CD38, CD40, CD40L, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, *Clostridium botulinum* toxin, *Clostridium perfringens* toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor-associated antigen, DAN, DCC, DcR3, DC-SIGN, Decay accelerating factor, des(1-3)-IGF-I (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, Enkephalinase, eNOS, Eot, eotaxin1, EpCAM, Ephrin B2/EphB4, EPO, ERCC, E-selectin, ET-1, Factor IIa, Factor VII, Factor VIIIc, Factor IX, fibroblast activation protein (FAP), Fas, FcR1, FEN-1, Ferritin, FGF, FGF-19, FGF-2, FGF3, FGF-8, FGFR, FGFR-3, Fibrin, FL, FLIP, Flt-3, Flt-4, Follicle stimulating hormone, Fractalkine, FZD1, FZD2, FZD3, FZD4, FZD5, FZD6, FZD7, FZD8, FZD9, FZD10, G250, Gas 6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (Myostatin), GDF-9, GDF-15 (MIC-1), GDNF, GDNF, GFAP, GFRa-1, GFR-alpha1, GFR-alpha2, GFR-alpha3, GITR, Glucagon, Glut 4, glycoprotein IIb/IIIa (GP IIb/IIa), GM-CSF, gp130, gp72, GRO, Growth hormone releasing factor, Hapten (NP-cap or NIP-cap), HB-EGF, HCC, HCMV gB envelope glycoprotein, HCMV) gH envelope glycoprotein, HCMV UL, Hemopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, High molecular weight melanoma-associated antigen (HMW-MAA), HIV gp120, HIV IIIB gp120 V3 loop, HLA, HLA-DR, HM1.24, HMFG PEM, HRG, Hrk, human cardiac myosin, human cytomegalovirus (HCMV), human growth hormone (HGH), HVEM, I-309, IAP, ICAM, ICAM-1, ICAM-3, ICE, ICOS, IFNg, Ig, IgA receptor, IgE, IGF, IGF binding proteins, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-23, interferon (INF)-alpha, INF-beta, INF-gamma, Inhibin, iNOS, Insulin A-chain, Insulin B-chain, Insulin-like growth factor 1, integrin alpha2, integrin alpha3, integrin alpha4, integrin alpha4/beta1, integrin alpha4/beta7, integrin alpha5 (alphaV), integrin alpha5/beta1, integrin alpha5/beta3, integrin alpha6, integrin beta1, integrin beta2, interferon gamma, IP-10, I-TAC, JE, Kallikrein 2, Kallikrein 5, Kallikrein 6, Kallikrein 11, Kallikrein 12, Kallikrein 14, Kallikrein 15, Kallikrein L1, Kallikrein L2, Kallikrein L3, Kallikrein L4, KC, KDR, Keratinocyte Growth Factor (KGF), laminin 5, LAMP, LAP, LAP (TGF-1), Latent TGF-1, Latent TGF-1 bp1, LBP, LDGF, LECT2, Lefty, Lewis-Y antigen, Lewis-Y related antigen, LFA-1, LFA-3, Lfo, LIF, LIGHT, lipoproteins, LIX, LKN, Lptn, L-Selectin, LT-a, LT-b, LTB4, LTBP-1, Lung surfactant, Luteinizing hormone, Lymphotoxin Beta Receptor, Mac-1, MAdCAM, MAG, MAP2, MARC, MCAM, MCAM, MCK-2, MCP, M-CSF, MDC, Mer, METALLOPROTEASES, MGDF receptor, MGMT, MHC (HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Muc1), MUC18, Muellerian-inhibitin substance, Mug, MuSK, NAIP, NAP, NCAD, N-Cadherin, NCA 90, NCAM, NCAM, Neprilysin, Neurotrophin-3, -4, or -6, Neurturin, Neuronal growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, Parathyroid hormone, PARC, PARP, PBR, PBSF, PCAD, P-Cadherin, PCNA, PDGF, PDGF, PDK-1, PECAM, PEM, PF4, PGE, PGF, PGI2, PGJ2, PIN, PLA2, placental alkaline phosphatase (PLAP), P1GF, PLP, PP14, Proinsulin, Prorelaxin, Protein C, PS, PSA, PSCA, prostate specific membrane antigen (PSMA), PTEN, PTHrp, Ptk, PTN, R51, RANK, RANKL, RANTES, RANTES, Relaxin A-chain, Relaxin B-chain, renin, respiratory syncytial virus (RSV) F, RSV Fgp, Ret, Rheumatoid factors, RLIP76, RPA2, RSK, S100, SCF/KL, SDF-1, SERINE, Serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T-cell receptors (e.g., T-cell receptor alpha/beta), TdT, TECK, TEM1, TEM5, TEM7, TEM8, TERT, testicular PLAP-like alkaline phosphatase, TfR, TGF, TGF-alpha, TGF-beta, TGF-beta Pan Specific, TGF-beta R1 (ALK-5), TGF-beta RII, TGF-beta RIIb, TGF-beta RIII, TGF-beta1, TGF-beta2, TGF-beta3, TGF-beta4, TGF-beta5, Thrombin, Thymus Ck-1, Thyroid stimulating hormone, Tie, TIMP, TIQ, Tissue Factor, TMEFF2, Tmpo, TMPRSS2, TNF, TNF-alpha, TNF-alpha beta, TNF-beta2, TNFα, TNF-R1, TNF-RII, TNFRSF10A (TRAIL R1Apo-2, DR4), TNFRSF10B (TRAIL R2DR5, KILLER, TRICK-2A, TRICK-B), TNFRSF10C (TRAIL R3 DcR1, LIT, TRID), TNFRSF10D (TRAIL R4 DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF RI CD120a, p55-60), TNFRSF1B (TNF RII CD120b, p75-80), TNFRSF26 (TNFRH3), TNFRSF3 (LTbR TNF RIII, TNFC R), TNFRSF4 (OX40 ACT35, TXGP1 R), TNFRSF5 (CD40 p50), TNFRSF6 (Fas Apo-1, APT1, CD95), TNFRSF6B (DcR3 M68, TR6), TNFRSF7 (CD27), TNFRSF8 (CD30), TNFRSF9 (4-1BB CD137, ILA), TNFRSF21 (DR6), TNFRSF22 (DcTRAIL R2 TNFRH2), TNFRST23 (Dc-TRAIL R1 TNFRH1), TNFRSF25 (DR3 Apo-3, LARD, TR-3, TRAMP, WSL-1), TNFSF10 (TRAIL Apo-2 Ligand, TL2), TNFSF11 (TRANCE/RANK Ligand ODF, OPG Ligand), TNFSF12 (TWEAK Apo-3 Ligand, DR3 Ligand), TNFSF13 (APRIL TALL2), TNFSF13B (BAFF BLYS, TALL1, THANK, TNFSF20), TNFSF14 (LIGHT HVEM Ligand, LTg), TNFSF15 (TL1A/VEGI), TNFSF18 (GITR Ligand AITR Ligand, TL6), TNFSF1A (TNF-a Conectin, DIF, TNFSF2), TNFSF1B (TNF-b LTa, TNFSF1), TNFSF3 (LTb TNFC, p33), TNFSF4 (OX40 Ligand gp34, TXGP1), TNFSF5 (CD40 Ligand CD154, gp39, HIGM1, IMD3, TRAP), TNFSF6 (Fas Ligand Apo-1 Ligand, APT1 Ligand), TNFSF7 (CD27 Ligand CD70), TNFSF8 (CD30 Ligand CD153), TNFSF9 (4-1BB Ligand CD137 Ligand), TP-1, t-PA, Tpo, TRAIL, TRAIL R, TRAIL-R1, TRAIL-R2, TRANCE, transferring receptor, TRF, Trk, TROP-2, TSG, TSLP, tumor-associated antigen CA 125, tumor-associated antigen expressing Lewis Y related carbohydrate, TWEAK, TXB2, Ung, uPAR, uPAR-1, Urokinase, VCAM, VCAM-1, VECAD, VE-Cadherin, VE-cadherin-2, VEFGR-1 (fit-1), VEGF, VEGFR, VEGFR-3 (flt-4), VEGI, VIM, Viral antigens, VLA, VLA-1, VLA-4, VNR integrin, von Willebrands factor, WIF-1, WNT1, WNT2, WNT2B/13, WNT3, WNT3A, WNT4, WNT5A, WNT5B, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, and receptors for hormones and growth factors, etc.

Glycoform Modification

Many polypeptides, including antibodies, are subjected to a variety of post-translational modifications involving carbohydrate moieties, such as glycosylation with oligosaccharides. There are several factors that can influence glycosylation. The species, tissue and cell type have all been shown to be important in the way that glycosylation occurs. In addition, the extracellular environment, through altered culture conditions such as serum concentration, may have a direct effect on glycosylation. (Lifely et al., 1995, Glycobiology 5(8): 813-822).

All antibodies contain carbohydrate at conserved positions in the constant regions of the heavy chain. Each antibody isotype has a distinct variety of N-linked carbohydrate structures. Aside from the carbohydrate attached to the heavy chain, up to 30% of human IgGs have a glycosylated Fab region. IgG has a single N-linked biantennary carbohydrate at Asn297 of the CH2 domain. For IgG from either serum or produced ex vivo in hybridomas or engineered cells, the IgG are heterogeneous with respect to the Asn297 linked carbohydrate. Jefferis et al., 1998, Immunol. Rev. 163:59-76; and Wright et al., 1997, Trends Biotech 15:26-32. For human IgG, the core oligosaccharide normally consists of GlcNAc$_2$Man$_3$GlcNAc, with differing numbers of outer residues.

The carbohydrate moieties of the present invention will be described with reference to commonly used nomenclature for the description of oligosaccharides. A review of carbohydrate chemistry which uses this nomenclature is found in Hubbard et al. 1981, Ann. Rev. Biochem. 50:555-583. This nomenclature includes, for instance, Man, which represents mannose; GlcNAc, which represents 2-N-acetylglucosamine; Gal which represents galactose; Fuc for fucose; and Glc, which represents glucose. Sialic acids are described by the shorthand notation NeuNAc, for 5-N-acetylneuraminic acid, and NeuNGc for 5-glycolylneuraminic.

The term "glycosylation" means the attachment of oligosaccharides (carbohydrates containing two or more simple sugars linked together e.g. from two to about twelve simple sugars linked together) to a glycoprotein. The oligosaccharide side chains are typically linked to the backbone of the glycoprotein through either N- or O-linkages. The oligosaccharides of the present invention occur generally are attached to a CH2 domain of an Fc region as N-linked oligosaccharides. "N-linked glycosylation" refers to the attachment of the carbohydrate moiety to an asparagine residue in a glycoprotein chain. The skilled artisan will recognize that, for example, each of murine IgG1, IgG2a, IgG2b and IgG3 as well as human IgG1, IgG2, IgG3, IgG4, IgA and IgD CH2 domains have a single site for N-linked glycosylation at amino acid residue 297 (Kabat et al. Sequences of Proteins of Immunological Interest, 1991).

For the purposes herein, a "mature core carbohydrate structure" refers to a processed core carbohydrate structure attached to an Fc region which generally consists of the following carbohydrate structure GlcNAc(Fucose)-GlcNAc-Man-(Man-GlcNAc)$_2$ typical of biantennary oligosaccharides. The mature core carbohydrate structure is attached to the Fc region of the glycoprotein, generally via N-linkage to Asn297 of a CH2 domain of the Fc region. A "bisecting GlcNAc" is a GlcNAc residue attached to the β1,4 mannose of the mature core carbohydrate structure. The bisecting GlcNAc can be enzymatically attached to the mature core carbohydrate structure by a β(1,4)-N-acetylglucosaminyl-transferase III enzyme (GnTIII). CHO cells do not normally express GnTIII (Stanley et al., 1984, J. Biol. Chem. 261: 13370-13378), but may be engineered to do so (Umana et al., 1999, Nature Biotech. 17:176-180).

The present invention contemplates Fc variants that comprise modified glycoforms or engineered glycoforms. By "modified glycoform" or "engineered glycoform" as used herein is meant a carbohydrate composition that is covalently attached to an IgG, wherein the carbohydrate composition differs chemically from that of a parent IgG. Engineered glycoforms may be useful for a variety of purposes, including but not limited to enhancing or reducing FcγR-mediated effector function. In certain embodiments, the Fc variants of the present invention are modified to control the level of fucosylated and/or bisecting oligosaccharides that are covalently attached to the Fc region. A variety of methods are well known in the art for generating modified glycoforms (Umana et al., 1999, Nat Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473); (U.S. Pat. No. 6,602,684; U.S. Ser. No. 10/277,370; U.S. Ser. No. 10/113,929; PCT WO 00/61739A1; PCT WO 01/29246A1; PCT WO 02/31140A1; PCT WO 02/30954A1); (Potelligent™ technology [Biowa, Inc., Princeton, N.J.]; GlycoMAb™ glycosylation engineering technology [GLYCART biotechnology AG, Zürich, Switzerland]; all of which are expressly incorporated by reference). These techniques control the level of fucosylated and/or bisecting oligosaccharides that are covalently attached to the Fc region, for example by expressing an IgG in various organisms or cell lines, engineered or otherwise (for example Lec-13 CHO cells or rat hybridoma YB2/0 cells), by regulating enzymes involved in the glycosylation pathway (for example FUT8 [α1,6-fucosyltranserase] and/or β1-4-N-acetylglucosaminyltransferase III [GnTIII]), or by modifying carbohydrate(s) after the IgG has been expressed. The use of a particular mode of generating a modified glycoform, for example the use of the Lec-13 cell line in the present study, is not meant to constrain the present invention to that particular embodiment. Rather, the present invention contemplates Fc variants with modified glycoforms irrespective of how they are produced.

Engineered glycoform typically refers to the different carbohydrate or oligosaccharide; thus an IgG variant, for example an antibody or Fc fusion, can include an engineered glycoform. Alternatively, engineered glycoform may refer to the IgG variant that comprises the different carbohydrate or oligosaccharide. For the purposes herein, a "parent Fc polypeptide" is a glycosylated Fc polypeptide having the same amino acid sequence and mature core carbohydrate structure as an engineered glycoform of the present invention, except that fucose is attached to the mature core carbohydrate structure. For instance, in a composition comprising the parent glycoprotein about 50-100% or about 70-100% of the parent glycoprotein comprises a mature core carbohydrate structure having fucose attached thereto.

The present invention provides a composition comprising a glycosylated Fc polypeptiden having an Fc region, wherein about 51-100% of the glycosylated Fc polypeptide in the composition comprises a mature core carbohydrate structure which lacks fucose, attached to the Fc region of the Fc polypeptide. More preferably, about 80-100% of the Fc polypeptide in the composition comprises a mature core carbohydrate structure which lacks fucose and most preferably about 90-99% of the Fc polypeptide in the composition lacks fucose attached to the mature core carbohydrate structure. In certain embodiments, the Fc polypeptide in the composition both comprises a mature core carbohydrate structure that lacks fucose and additionally comprises at least one amino acid modification in the Fc region. In certain embodiments, the combination of engineered glycoform and amino acid modification provides optimal Fc receptor binding properties to the Fc polypeptide.

Fc Receptor Binding Properties

The Fc variants of the present invention may be optimized for a variety of Fc receptor binding properties. An Fc variant that is engineered or predicted to display one or more optimized properties is herein referred to as an "optimized Fc variant". Properties that may be optimized include but are not limited to increased or reduced affinity for an FcγR. In certain embodiments, the Fc variants of the present invention are optimized to possess increased affinity for a human activating FcγR, preferably FcγRI, FcγRIIa, FcγRIIc, FcγRIIIa, and FcγRIIIb, most preferably FcγRIIa and FcγRIIIa. In another embodiment, the Fc variants are optimized to possess reduced affinity for the human inhibitory receptor FcγRIIb. These embodiments are anticipated to provide Fc polypeptides with increased therapeutic properties in humans, for example enhanced effector function and greater anti-cancer potency. In other embodiments, Fc variants of the present invention provide increased affinity for one or more FcγRs, yet reduced affinity for one or more other FcγRs. For example, an Fc variant of the present invention may have increased binding to FcγRI, FcγRIIa, and/or FcγRIIIa, yet reduced binding to FcγRIIb.

By "greater affinity" or "improved affinity" or "enhanced affinity" or "increased affinity" or "better affinity" than a parent Fc polypeptide, as used herein is meant that an Fc variant binds to an Fc receptor with a significantly higher equilibrium constant of association (KA) or lower equilibrium constant of dissociation (KD) than the parent Fc polypeptide when the amounts of variant and parent polypeptide in the binding assay are essentially the same. For example, the Fc variant with improved Fc receptor binding affinity may display from about 5 fold to about 1000 fold, e.g. from about 10 fold to about 500 fold improvement in Fc receptor binding affinity compared to the parent Fc polypeptide, where Fc receptor binding affinity is determined, for example, as disclosed in the Examples herein. Accordingly, by "reduced affinity" as compared to a parent Fc polypeptide as used herein is meant that an Fc variant binds an Fc receptor with significantly lower KA or higher KD than the parent Fc polypeptide. A promising means for enhancing the anti-tumor potency of antibodies is via enhancement of their ability to mediate cytotoxic effector functions such as ADCC, ADCP, and CDC. The importance of FcγR-mediated effector functions for the anti-cancer activity of antibodies has been demonstrated in mice (Clynes et al., 1998, *Proc Natl Acad Sci USA* 95:652-656; Clynes et al., 2000, *Nat Med* 6:443-446, both hereby entirely incorporated by reference), and the affinity of interaction between Fc and certain FcγRs correlates with targeted cytotoxicity in cell-based assays (Shields et al., 2001, *J Biol Chem* 276:6591-6604; Presta et al., 2002, *Biochem Soc Trans* 30:487-490; Shields et al., 2002, *Biol Chem* 277:26733-26740, all hereby entirely incorporated by reference). A critical set of data supporting the relevance of FcγR-mediated effector functions in antibody therapeutic mechanism are the correlations observed between clinical efficacy in humans and their allotype of high and low affinity polymorphic forms of FcγRs. In particular, human IgG1 binds with greater affinity to the V158 isoform of FcγRIIIa than the F158 isoform. This difference in affinity, and its effect FcγR-mediated effector functions such as ADCC and/or ADCP, has been shown to be a significant determinant of the efficacy of the anti-CD20 antibody rituximab (Rituxan®, Biogenldec). Patients with the V158 allotype respond favorably to rituximab treatment; however, patients with the lower affinity F158 allotype respond poorly (Cartron et al., 2002, *Blood* 99:754-758; Weng & Levy, 2003, *J Clin Oncol*, 21(21):3940-3947, hereby entirely incorporated by reference). Approximately 10-20% of humans are V158/V158 homozygous, 45% are V158/F158 heterozygous, and 35-45% of humans are F158/F158 homozygous (Lehrnbecher et al., 1999, *Blood* 94:4220-4232; Cartron et al., 2002, *Blood* 99:754-758, both hereby entirely incorporated by reference). Thus 80-90% of humans are poor responders, e.g., they have at least one allele of the F158 FcγRIIIa. Correlations between polymorphisms and clinical outcome have also been documented for the activating receptor FcγRIIa (Weng & Levy, 2003, *J Clin Oncol*, 21(21):3940-3947; Cheung et al., 2006 *J Clin Oncol* 24(18):1-6; herein expressly incorporated by reference). The H131 and R131 allotypes of this receptor are approximately equally present in the human population. Non-Hodgkin's lymphoma patients homozygous for the H131 isoform, which binds more tightly to human IgG2 than R131 FcγRIIa, responded better to anti-CD20 rituximab therapy than those homozygous for R131 FcγRIIa (Weng & Levy, 2003, *J Clin Oncol*, 21(21):3940-3947). The FcγRIIa polymorphism also correlated with clinical outcome following immunotherapy of neuroblastoma with a murine IgG3 anti-GD2 antibody and GMC-SF (Cheung et al., 2006 *J Clin Oncol* 24(18):1-6). Murine IgG3 has higher affinity for the R131 isoform of human FcγRIIa than the H131 form, and patients homozygous for R131 showed better response than H/H homozygous patients. Notably, this is the first documentation of a clinical correlation between FcγR polymorphism and outcome in solid tumors, suggesting that the importance of FcγR-mediated effector functions is not limited to antibodies targeting hematological cancers.

Together these data suggest that an antibody that is optimized for binding to certain FcγRs may better mediate effector functions and thereby destroy cancer cells more effectively in patients. Indeed progress has been made towards this goal, see for example U.S. Ser. No. 10/672,280, U.S. Ser. No. 10/822,231, U.S. Ser. No. 11/124,620, and U.S. Ser. No. 11/256,060. The majority of emphasis has thus far been directed at enhancing the affinity of antibodies for the activating receptor FcγRIIIa. However a major obstacle to improving antibody anti-tumor efficacy is engineering the proper balance between activating and inhibiting receptors. This is supported by the positive FcγRIIa polymorphism correlations with clinical outcome cited above because this receptor is virtually always expressed on immune cells along with the inhibitory receptor FcγRIIb. FIG. 1 shows the activating and inhibitory FcγRs that may be involved in regulating the activities of several immune cell types. Whereas NK cells only express the activating receptor FcγRIIIa, all of the other cell types, including neutrophils, macrophages, and dendritic cells, express the inhibitory receptor FcγRIIb, as well the other activating receptors FcγRI and FcγRIIa. For these cell types optimal effector function may result from an antibody that has increased affinity for activation receptors, for example FcγRI, FcγRIIa, and FcγRIIIa, yet reduced affinity for the inhibitory receptor FcγRIIb. Notably, these other cells types can utilize FcγRs to mediate not only innate effector functions that directly lyse cells, for example ADCC, but can also phagocytose targeted cells and process antigen for presentation to other immune cells, events that can ultimately lead to the generation of adaptive immune response. For example, recent data suggest that the balance between FcγRIIa and FcγRIIb establishes a threshold of DC activation and enables immune complexes to mediate opposing effects on dendritic cell (DC) maturation and function (Boruchov et al., 2005, *J Clin Invest.*, September 15, 1-10, entirely incorporated by reference). Thus Fc variants that selectively ligate activating versus inhibitory receptors, for example FcγRIIa versus FcγRIIb, may affect DC processing, T cell priming and activation, antigen immunization, and/or efficacy against cancer (Dhodapkar & Dhodapkar, 2005, *Proc Natl Acad Sci USA*, 102, 6243-6244, entirely incorporated by reference). Such variants may be employed as novel strategies for targeting antigens to the activating or inhibitory FcγRs on human DCs, macrophages, or other antigen presenting cells to generate target-specific immunity.

In various aspects, the present application is directed to Fc variants having differential specificity for various receptors. For example, the change in affinity for one or more receptors can be increased relative to a second receptor or group of receptors.

In one aspect, the present invention is directed to an Fc variant of a parent Fc polypeptide comprising at least a first and a second substitution. The first and second substitutions are each at a position selected from group consisting of 234, 235, 236, 239, 267, 268, 293, 295, 324, 327, 328, 330, and 332 according to the EU index. The Fc variant exhibits an increase in affinity for one or more receptors selected from the group consisting of FcγRI, FcγRIIa, and FcγRIIIa as compared to the increase in a affinity of the Fc variant for the FcγRIIb receptor. The increases in affinities are relative to the parent polypeptide. In certain embodiments, the Fc variant has increased affinity for the activating receptor as compared to the parent Fc polypeptide but has reduced affinity (i.e. a negative increase in affinity) for FcγRIIb as compared to the parent Fc polypeptide. The increase in affinity is greater for an activating receptor than it is for FcγRIIb. Other activating receptors are also contemplated. In certain embodiments, the affinity for FcγRI, FcγRIIa, and FcγRIIIa receptors is increased.

Table 1 illustrates several embodiments of human Fc receptor affinity profiles wherein the Fc variant provide selectively increased affinity for activating receptors relative to the inhibitory receptor FcγRIIb. One application of Fc variants with such Fc receptor affinity profiles is to impart antibodies, Fc fusions, or other Fc polypeptides with enhanced FcγR-mediated effector function and cellular activation, specifically for cells that express both activating and inhibitory receptors including but not limited to neutrophils, monocytes and macrophages, and dendritic cells.

TABLE 1

Selectively increased affinity for activating receptors

|  | FcγRI | FcγRIIa | FcγRIIb | FcγRIIIa |
| --- | --- | --- | --- | --- |
| Embodiment 1 | + or WT | ++ | + | ++ |
| Embodiment 2 | + or WT | + | WT | + |
| Embodiment 3 | + or WT | + | − | + |

In another aspect, the Fc variant exhibits an increase in affinity of the Fc variant for the FcγRIIb receptor as compared to the increase in affinity for one or more activating receptors. Activating receptors include FcγRI, FcγRIIa, and FcγRIIIa. Increased affinities are relative to the parent polypeptide. The first and second substitutions each at a position selected from group consisting of 234, 235, 236, 239, 267, 268, 293, 295, 324, 327, 328, 330 and 332 according to the EU index. In other variations, the Fc variant has increased affinity for the activating receptor as compared to the parent Fc polypeptide but has reduced affinity (i.e. a negative increase in affinity) for FcγRIIb as compared to the parent Fc polypeptide. The increase in affinity is greater for FcγRIIb than it is for the one or more activating receptors. In further variations, the affinity for FcγRIIb is increased.

Table 2 illustrates several embodiments of human Fc receptor affinity profiles wherein the Fc variant provide selectively increased affinity for the inhibitory receptor FcγRIIb relative to one or more activating receptors. One application of Fc variants with such Fc receptor affinity profiles is to impart antibodies, Fc fusions, or other Fc polypeptides with reduced FcγR-mediated effector function and to inhibit cellular activation, specifically for cells that express the inhibitory receptor FcγRIIb, including but not limited to neutrophils, monocytes and macrophages, dendritic cells, and B cells.

TABLE 2

Selectively increased affinity for inhibitory receptor

|  | FcγRI | FcγRIIa | FcγRIIb | FcγRIIIa |
| --- | --- | --- | --- | --- |
| Embodiment 1 | + | + | ++ | + |
| Embodiment 2 | WT or − | WT or − | + | WT or − |
| Embodiment 3 | − | − | + | − |

In particular embodiments, the Fc variants that provide selectively increased affinity for activating receptors or inhibitory receptor are murine antibodies, and said selective enhancements are to murine Fc receptors. As described below in the examples, various embodiments provide for the generation of surrogate antibodies that are designed to be most compatible with mouse disease models, and may be informative for example in pre-clinical studies.

The presence of different polymorphic forms of FcγRs provides yet another parameter that impacts the therapeutic utility of the Fc variants of the present invention. Whereas the specificity and selectivity of a given Fc variant for the different classes of FcγRs significantly affects the capacity of an Fc variant to target a given antigen for treatment of a given disease, the specificity or selectivity of an Fc variant for different polymorphic forms of these receptors may in part determine which research or pre-clinical experiments may be appropriate for testing, and ultimately which patient populations may or may not respond to treatment. Thus the specificity or selectivity of Fc variants of the present invention to Fc receptor polymorphisms, including but not limited to FcγRIIa, FcγRIIIa, and the like, may be used to guide the selection of valid research and pre-clinical experiments, clinical trial design, patient selection, dosing dependence, and/or other aspects concerning clinical trials.

Fc variants of the invention may comprise modifications that modulate interaction with Fc receptors other than FcγRs, including but not limited to complement proteins, FcRn, and Fc receptor homologs (FcRHs). FcRHs include but are not limited to FcRH1, FcRH2, FcRH3, FcRH4, FcRH5, and FcRH6 (Davis et al., 2002, Immunol. Reviews 190:123-136).

Clearly an important parameter that determines the most beneficial selectivity of a given Fc variant to treat a given disease is the context of the Fc variant. Thus the Fc receptor selectivity or specificity of a given Fc variant will provide different properties depending on whether it composes an antibody, Fc fusion, or Fc variants with a coupled fusion or conjugate partner.

Various Fc variants are used in therapeutic utilities based on their respective receptor specificities. The utility of a given Fc variant for therapeutic purposes can depend on the epitope or form of the target antigen and the disease or indication being treated. For some targets and indications, enhanced FcγR-mediated effector functions may be preferable. This may be particularly favorable for anti-cancer Fc variants. Thus Fc variants can be used that comprise Fc variants that provide increased affinity for activating FcγRs and/or reduced affinity for inhibitory FcγRs. For some targets and indications, it may be further beneficial to utilize Fc variants that provide differential selectivity for different activating FcγRs; for example, in some cases enhanced binding to FcγRIIa and FcγRIIIa may be desired, but not FcγRI, whereas in other cases, enhanced binding only to FcγRIIa may be preferred.

For certain targets and indications, it may be preferable to utilize Fc variants that enhance both FcγR-mediated and complement-mediated effector functions, whereas for other cases it may be advantageous to utilize Fc variants that enhance either FcγR-mediated or complement-mediated effector functions. For some targets or cancer indications, it may be advantageous to reduce or ablate one or more effector functions, for example by knocking out binding to C1q, one or more FcγR's, FcRn, or one or more other Fc ligands. For other targets and indications, it may be preferable to utilize Fc variants that provide enhanced binding to the inhibitory FcγRIIb, yet WT level, reduced, or ablated binding to activating FcγRs. This may be particularly useful, for example, when the goal of an Fc variant is to inhibit inflammation or auto-immune disease, or modulate the immune system in some way.

In certain embodiments, the target of the Fc variants of the present invention is itself one or more Fc ligands. Fc polypeptides of the invention can be utilized to modulate the activity of the immune system, and in some cases to mimic the effects of IVIg therapy in a more controlled, specific, and efficient manner. IVIg is effectively a high dose of immunoglobulins delivered intravenously. In general, IVIg has been used to down-regulate autoimmune conditions. It has been hypothesized that the therapeutic mechanism of action of IVIg involves ligation of Fc receptors at high frequency (J. Bayry et al., 2003, Transfusion Clinique et Biologique 10: 165-169; Binstadt et al., 2003, J Allergy Clin. Immunol, 697-704). Indeed animal models of lthrombocytopenia purpura (ITP) show that the isolated Fc are the active portion of IVIg (Samuelsson et al, 2001, Pediatric Research 50(5), 551). For use in therapy, iimmunoglobulins are harvested from thousands of donors, with all of the concomitant problems associated with non-recombinant biotherapeutics collected from humans. An Fc variant of the present invention should serve all of the roles of IVIg while being manufactured as a recombinant protein rather than harvested from donors.

The immunomodulatory effects of IVIg may be dependent on productive interaction with one or more Fc ligands, including but not limited to FcγRs, complement proteins, and FcRn. In some embodiments, Fc variants of the invention with increased affinity for FcγRIIb can be used to promote anti-inflammatory activity (Samuelsson et al., 2001, *Science* 291: 484-486) and or to reduce autoimmunity (Hogarth, 2002, *Current Opinion in Immunology,* 14:798-802). In other embodiments, Fc polypeptides of the invention with increased affinity for one or more FcγRs can be utilized by themselves or in combination with additional modifications to reduce autoimmunity (Hogarth, 2002, *Current Opinion in Immunology,* 14:798-802). In alternative embodiments, Fc variants of the invention with increased affinity for FcγRIIIa but reduced capacity for intracellular signaling can be used to reduce immune system activation by competitively interfering with FcγRIIIa binding. The context of the Fc variant impacts the desired specificity. For example, Fc variants that provide enhanced binding to one or more activating FcγRs may provide optimal immunomodulatory effects in the context of an antibody, Fc fusion, isolated Fc, or Fc fragment by acting as an FcγR antagonist (van Mirre et al., 2004, J. Immunol. 173:332-339). However, fusion or conjugation of two or more Fc variants may provide different effects, and for such an Fc polypeptide it may be optimal to utilize Fc variants that provide increased affinity for an inhibitory receptor.

The Fc variants of the present invention may be used as immunomodulatory therapeutics. Binding to or blocking Fc receptors on immune system cells may be used to influence immune response in immunological conditions including but not limited to idiopathic thrombocytopenia purpura (ITP) and rheumatoid arthritis (RA) among others. By use of the affinity enhanced Fc variants of the present invention, the dosages required in typical IVIg applications may be reduced while obtaining a substantially similar therapeutic effect. The Fc variants may provide enhanced binding to an FcγR, including but not limited to FcγRIIa, FcγRIIb, FcγRIIIa, FcγRIIIb, and/or FcγRI. In particular, binding enhancements to FcγRIIb would increase expression or inhibitory activity, as needed, of that receptor and improve efficacy. Alternatively, blocking binding to activation receptors such as FcγRIIIb or FcγRI may improve efficacy. In addition, modulated affinity of the Fc variants for FcRn and/or also complement may also provide benefits.

In one embodiment, Fc variants that provide enhanced binding to the inhibitory receptor FcγRIIb provide an enhancement to the IVIg therapeutic approach. In particular, the Fc variants of the present invention that bind with greater affinity to the FcγRIIb receptor than parent Fc polypeptide may be used. Such Fc variants would thus function as FcγRIIb agonists, and would be expected to enhance the beneficial effects of IVIg as an autoimmune disease therapeutic and also as a modulator of B-cell proliferation. In addition, such FcγRIIb-enhanced Fc variants may also be further modified to have the same or limited binding to other receptors. In additional embodiments, the Fc variants with enhanced FcγRIIb affinity may be combined with mutations that reduce or ablate to other receptors, thereby potentially further minimizing side effects during therapeutic use.

Such immunomodulatory applications of the Fc variants of the present invention may also be utilized in the treatment of oncological indications, especially those for which antibody therapy involves antibody-dependant cytotoxic mechanisms. For example, an Fc variant that enhances affinity to FcγRIIb may be used to antagonize this inhibitory receptor, for example by binding to the Fc/FcγRIIb binding site but failing to trigger, or reducing cell signaling, potentially enhancing the effect of antibody-based anti-cancer therapy. Such Fc variants, functioning as FcγRIIb antagonists, may either block the inhibitory properties of FcγRIIb, or induce its inhibitory function as in the case of IVIg. An FcγRIIb antagonist may be used as co-therapy in combination with any other therapeutic, including but not limited to antibodies, acting on the basis of ADCC related cytotoxicity. FcγRIIb antagonistic Fc variants of this type are preferably isolated Fc or Fc fragments, although in alternate embodiments antibodies and Fc fusions may be used.

Additional Modifications

Modification may be made to improve the IgG stability, solubility, function, or clinical use. In certain embodiments, the Fc variants of the present invention may comprise modifications to reduce immunogenicity in humans. In certain embodiments, the immunogenicity of an Fc variant of the present invention is reduced using a method described in U.S. Ser. No. 11/004,590, filed Dec. 3, 2004, hereby entirely incorporated by reference. In alternate embodiments, the Fc variants of the present invention are humanized (Clark, 2000, *Immunol Today* 21:397-402, hereby entirely incorporated by reference). By "humanized" antibody as used herein is meant an antibody comprising a human framework region (FR) and one or more complementarity determining regions (CDR's) from a non-human (usually mouse or rat) antibody. The non-human antibody providing the CDR's is called the "donor" and the human immunoglobulin providing the framework is called the "acceptor". Humanization relies principally on the grafting of donor CDRs onto acceptor (human) VL and VH frameworks (e.g., Winter et al, U.S. Pat. No. 5,225,539, hereby entirely incorporated by reference). This strategy is referred to as "CDR grafting". "Backmutation" of selected acceptor framework residues to the corresponding donor residues is often required to regain affinity that is lost in the initial grafted construct (U.S. Pat. No. 5,530,101; U.S. Pat. No. 5,585,089; U.S. Pat. No. 5,693,761; U.S. Pat. No. 5,693,762; U.S. Pat. No. 6,180,370; U.S. Pat. No. 5,859,205; U.S. Pat. No. 5,821,337; U.S. Pat. No. 6,054,297; and U.S. Pat. No. 6,407,213, all hereby entirely incorporated by reference). The humanized antibody optimally also will comprise at least a portion of an immunoglobulin constant region, typically that of a human immunoglobulin, and thus will typically comprise a human Fc region. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein, all hereby entirely incorporated by reference). Humanization methods include but are not limited to methods described in Jones et al., 1986, *Nature* 321:522-525; Riechmann et al., 1988; *Nature* 332:323-329; Verhoeyen et al., 1988, *Science,* 239:1534-1536; Queen et al., 1989, *Proc Natl Acad Sci, USA* 86:10029-33; He et al., 1998, J. Immunol. 160: 1029-1035; Carter et al., 1992, *Proc Natl Acad Sci USA* 89:4285-9, Presta et al., 1997, Cancer Res.57(20):4593-9; Gorman et al., 1991, Proc. Natl. Acad. Sci. USA 88:4181-4185; O'Connor et al., 1998, *Protein Eng* 11:321-8, all hereby entirely incorporated by reference. Humanization or other methods of reducing the immunogenicity of nonhuman antibody variable regions may include resurfacing methods, as described for example in Roguska et al., 1994, Proc. Natl. Acad. Sci. USA 91:969-973, hereby entirely incorporated by reference. In one embodiment, the parent antibody has been affinity matured, as is well known in the art. Structure-based methods may be employed for humanization and affinity maturation, for example as described in U.S. Ser. No. 11/004, 590, hereby entirely incorporated by reference. Selection based methods may be employed to humanize and/or affinity mature antibody variable regions, including but not limited to methods described in Wu et al., 1999, J. Mol. Biol. 294:151-162; Baca et al., 1997, J. Biol. Chem. 272(16):10678-10684; Rosok et al., 1996, J. Biol. Chem. 271(37): 22611-22618; Rader et al., 1998, Proc. Natl. Acad. Sci. USA 95: 8910-8915; Krauss et al., 2003, Protein Engineering 16(10):753-759, all hereby entirely incorporated by reference. Other humanization methods may involve the grafting of only parts of the CDRs, including but not limited to methods described in U.S. Ser. No. 09/810,502; Tan et al., 2002, J. Immunol. 169:1119-1125; De Pascalis et al., 2002, J. Immunol. 169:3076-3084, all hereby entirely incorporated by reference.

Modifications to reduce immunogenicity may include modifications that reduce binding of processed peptides derived from the parent sequence to MHC proteins. For example, amino acid modifications may be engineered such that there are no or a minimal number of immune epitopes that are predicted to bind, with high affinity, to any prevalent MHC alleles. Several methods of identifying MHC-binding epitopes in protein sequences are known in the art and may be used to score epitopes in an Fc variant of the present invention. See for example WO 98/52976; WO 02/079232; WO 00/3317; U.S. Ser. No. 09/903,378; U.S. Ser. No. 10/039,170; U.S. Ser. No. 60/222,697; U.S. Ser. No. 10/754,296; PCT WO 01/21823; and PCT WO 02/00165; Mallios, 1999, *Bioinformatics* 15: 432-439; Mallios, 2001, *Bioinformatics* 17: 942-948; Sturniolo et al., 1999, *Nature Biotech.* 17: 555-561; WO 98/59244; WO 02/069232; WO 02/77187; Marshall et al., 1995, *J. Immunol.* 154: 5927-5933; and Hammer et al., 1994, *J. Exp. Med.* 180: 2353-2358, all hereby entirely incorporated by reference. Sequence-based information can be used to determine a binding score for a given peptide—MHC interaction (see for example Mallios, 1999, *Bioinformatics* 15: 432-439; Mallios, 2001, *Bioinformatics* 17: p942-948; Sturniolo et. al., 1999, *Nature Biotech.* 17: 555-561, all hereby entirely incorporated by reference).

In an alternate embodiment, the Fc variant of the present invention is conjugated or operably linked to another therapeutic compound. The therapeutic compound may be a cytotoxic agent, a chemotherapeutic agent, a toxin, a radioisotope, a cytokine, or other therapeutically active agent. The IgG may be linked to one of a variety of nonproteinaceous polymers, e.g., polyethylene glycol, polypropylene glycol, polyoxyalkylenes, or copolymers of polyethylene glycol and polypropylene glycol.

Production and Experimental Characterization of Fc Variants

The present invention provides methods for engineering, producing, and screening Fc variants. The described methods are not meant to constrain the present invention to any particular application or theory of operation. Rather, the provided methods are meant to illustrate generally that one or more Fc variants may be engineered, produced, and screened experimentally to obtain Fc variants with optimized effector function. A variety of methods are described for designing, producing, and testing antibody and protein variants in U.S. Ser. No. 10/672,280, U.S. Ser. No. 10/822,231, U.S. Ser. No. 11/124,620, and U.S. Ser. No. 11/256,060, all hereby entirely incorporated by reference.

A variety of protein engineering methods may be used to design Fc variants with optimized effector function. In one embodiment, a structure-based engineering method may be used, wherein available structural information is used to guide substitutions. An alignment of sequences may be used to guide substitutions at the identified positions. Alternatively, random or semi-random mutagenesis methods may be used to make amino acid modifications at the desired positions.

Methods for production and screening of Fc variants are well known in the art. General methods for antibody molecular biology, expression, purification, and screening are described in Antibody Engineering, edited by Duebel & Kontermann, Springer-Verlag, Heidelberg, 2001; and Hayhurst & Georgiou, 2001, *Curr Opin Chem Biol* 5:683-689; Maynard & Georgiou, 2000, *Annu Rev Biomed Eng* 2:339-76, all hereby entirely incorporated by reference. Also see the methods described in U.S. Ser. No. 10/672,280, U.S. Ser. No. 10/822,231, U.S. Ser. No. 11/124,620, and U.S. Ser. No. 11/256,060, all hereby entirely incorporated by reference.

In one embodiment of the present invention, the Fc variant sequences are used to create nucleic acids that encode the member sequences, and that may then be cloned into host cells, expressed and assayed, if desired. These practices are carried out using well-known procedures, and a variety of methods that may find use in the present invention are described in Molecular Cloning—A Laboratory Manual, 3rd Ed. (Maniatis, Cold Spring Harbor Laboratory Press, New York, 2001), and Current Protocols in Molecular Biology (John Wiley & Sons), both entirely incorporated by reference. The Fc variants of the present invention may be produced by culturing a host cell transformed with nucleic acid, preferably an expression vector, containing nucleic acid encoding the Fc variants, under the appropriate conditions to induce or cause expression of the protein. A wide variety of appropriate host cells may be used, including but not limited to mammalian cells, bacteria, insect cells, and yeast. For example, a variety of cell lines that may find use in the present invention are described in the ATCC cell line catalog, available from the American Type Culture Collection. The methods of introducing exogenous nucleic acid into host cells are well known in the art, and will vary with the host cell used.

In certain embodiments, Fc variants are purified or isolated after expression. Antibodies may be isolated or purified in a variety of ways known to those skilled in the art. Standard purification methods include chromatographic techniques, electrophoretic, immunological, precipitation, dialysis, filtration, concentration, and chromatofocusing techniques. As is well known in the art, a variety of natural proteins bind antibodies, for example bacterial proteins A, G, and L, and these proteins may find use in the present invention for purification. Purification can often be enabled by a particular fusion partner. For example, proteins may be purified using glutathione resin if a GST fusion is employed, $Ni^{+2}$ affinity chromatography if a His-tag is employed, or immobilized anti-flag antibody if a flag-tag is used. For general guidance in suitable purification techniques, see Antibody Purification: Principles and Practice, $3^{rd}$ Ed., Scopes, Springer-Verlag, NY, 1994, hereby entirely incorporated by reference.

Fc variants may be screened using a variety of methods, including but not limited to those that use in vitro assays, in vivo and cell-based assays, and selection technologies. Automation and high-throughput screening technologies may be utilized in the screening procedures. Screening may employ the use of a fusion partner or label, for example an immune label, isotopic label, or small molecule label such as a fluorescent or colorimetric dye.

In certain embodiments, the functional and/or biophysical properties of Fc variants are screened in an in vitro assay. In certain embodiments, the protein is screened for functionality, for example its ability to catalyze a reaction or its binding affinity to its target.

As is known in the art, a subset of screening methods are those that select for favorable members of a library. The methods are herein referred to as "selection methods", and these methods find use in the present invention for screening Fc variants. When protein libraries are screened using a selection method, only those members of a library that are favorable, that is which meet some selection criteria, are propagated, isolated, and/or observed. A variety of selection methods are known in the art that may find use in the present invention for screening protein libraries. Other selection methods that may find use in the present invention include methods that do not rely on display, such as in vivo methods. A subset of selection methods referred to as "directed evolution" methods are those that include the mating or breading of favorable sequences during selection, sometimes with the incorporation of new mutations.

In certain embodiments, Fc variants are screened using one or more cell-based or in vivo assays. For such assays, purified or unpurified proteins are typically added exogenously such that cells are exposed to individual variants or pools of variants belonging to a library. These assays are typically, but not always, based on the function of the Fc polypeptide; that is, the ability of the Fc polypeptide to bind to its target and mediate some biochemical event, for example effector function, ligand/receptor binding inhibition, apoptosis, and the like. Such assays often involve monitoring the response of cells to the IgG, for example cell survival, cell death, change in cellular morphology, or transcriptional activation such as cellular expression of a natural gene or reporter gene. For example, such assays may measure the ability of Fc variants to elicit ADCC, ADCP, or CDC. For some assays additional cells or components, that is in addition to the target cells, may need to be added, for example serum complement, or effector cells such as peripheral blood monocytes (PBMCs), NK cells, macrophages, and the like. Such additional cells may be from any organism, preferably humans, mice, rat, rabbit, and monkey. Antibodies may cause apoptosis of certain cell lines expressing the target, or they may mediate attack on target cells by immune cells which have been added to the assay. Methods for monitoring cell death or viability are known in the art, and include the use of dyes, immunochemical, cytochemical, and radioactive reagents. Transcriptional activation may also serve as a method for assaying function in cell-based assays. Alternatively, cell-based screens are performed using cells that have been transformed or transfected with nucleic acids encoding the variants. That is, Fc variants are not added exogenously to the cells.

In certain embodiments, the immunogenicity of the Fc variants is determined experimentally using one or more cell-based assays. Several methods can be used for experimental confirmation of epitopes.

The biological properties of the Fc variants of the present invention may be characterized in cell, tissue, and whole organism experiments. As is known in the art, drugs are often tested in animals, including but not limited to mice, rats, rabbits, dogs, cats, pigs, and monkeys, in order to measure a drug's efficacy for treatment against a disease or disease model, or to measure a drug's pharmacokinetics, toxicity, and other properties. The animals may be referred to as disease models. Therapeutics are often tested in mice, including but not limited to nude mice, SCID mice, xenograft mice, and transgenic mice (including knockins and knockouts). Such experimentation may provide meaningful data for determination of the potential of the protein to be used as a therapeutic. Any organism, preferably mammals, may be used for testing. For example because of their genetic similarity to humans, monkeys can be suitable therapeutic models, and thus may be used to test the efficacy, toxicity, pharmacokinetics, or other property of the IgGs of the present invention. Tests of the in humans are ultimately required for approval as drugs, and thus of course these experiments are contemplated. Thus the IgGs of the present invention may be tested in humans to determine their therapeutic efficacy, toxicity, immunogenicity, pharmacokinetics, and/or other clinical properties.

Therapeutic Use of Fc Variants

The Fc variants of the present invention may find use in a wide range of products. In one embodiment the Fc variant of the present invention is a therapeutic, a diagnostic, or a research reagent, preferably a therapeutic. The Fc variant may find use in an antibody composition that is monoclonal or polyclonal. In certain embodiments, the Fc variants of the present invention are used to kill target cells that bear the target antigen, for example cancer cells. In an alternate embodiment, the Fc variants of the present invention are used to block, antagonize, or agonize the target antigen, for example for antagonizing a cytokine or cytokine receptor. In an alternative embodiment, the Fc variants of the present invention are used to block, antagonize, or agonize the target antigen and kill the target cells that bear the target antigen.

The Fc variants of the present invention may be used for various therapeutic purposes. In certain embodiments, an antibody comprising the Fc variant is administered to a patient to treat an antibody-related disorder. A "patient" for the purposes of the present invention includes humans and other animals, preferably mammals and most preferably humans. By "antibody related disorder" or "antibody responsive disorder" or "condition" or "disease" herein are meant a disorder that may be ameliorated by the administration of a pharmaceutical composition comprising an Fc variant of the present invention. Antibody related disorders include but are not limited to autoimmune diseases, immunological diseases, infectious diseases, inflammatory diseases, neurological diseases, pain, pulmonary diseases, hematological conditions, fibrotic conditions, and oncological and neoplastic diseases including cancer. By "cancer" and "cancerous" herein refer to or describe the physiological condition in mammals that is typically characterized by unregulated cell growth. Examples of cancer include but are not limited to carcinoma, lymphoma, blastoma, sarcoma (including liposarcoma), neuroendocrine tumors, mesothelioma, schwanoma, meningioma, adenocarcinoma, melanoma, and leukemia and lymphoid malignancies. Other conditions that may be treated include but are not limited to rheumatoid arthritis, juvenile rheumatoid arthritis, crohn's disease, ulcerative colitis, Sjorgren's disease, multiple sclerosis, ankylosing spondylitis, asthma, allergies and allergenic conditions, graft versus host disease, and the like. The term "treatment" as used herein is meant to include therapeutic treatment, as well as prophylactic, or suppressive measures for the disease, condition or disorder. Thus, for example, successful administration of a pharmaceutical composition comprising an Fc variant of the present invention prior to onset of the disease results in "treatment" of the disease. As another example, successful administration of a pharmaceutical composition comprising an Fc variant of the present invention after clinical manifestation of the disease to combat the symptoms of the disease comprises "treatment" of the disease. "Treatment" also encompasses administration of a pharmaceutical composition comprising an Fc variant of the present invention after the appearance of the disease in order to eradicate the disease. Successful administration of a pharmaceutical composition comprising an Fc variant of the present invention after onset and after clinical symptoms have developed, with possible abatement of clinical symptoms and perhaps amelioration of the disease, comprises "treatment" of the disease. Those "in need of treatment" as used herein include mammals already having the disease or disorder, as well as those prone to having the disease or disorder, including those in which the disease or disorder is to be prevented. A variety of diseases that may be treated using the Fc variants of the present invention are described in U.S. Ser. No. 11/124,620, filed May 5, 2005 and entitled "Optimized Fc Variants", hereby expressly incorporated by reference.

In one embodiment, an Fc variant of the present invention is the only therapeutically active agent administered to a patient. Alternatively, the Fc variant of the present invention is administered in combination with one or more other therapeutic agents, including but not limited to cytotoxic agents, chemotherapeutic agents, cytokines, growth inhibitory agents, anti-hormonal agents, kinase inhibitors, anti-angiogenic agents, cardioprotectants, or other therapeutic agents, as well as pre- or post-surgery. The IgG variants may be administered concomitantly with one or more other therapeutic regimens. For example, an Fc variant of the present invention may be administered to the patient along with surgery, chemotherapy, radiation therapy, or any or all of surgery, chemotherapy and radiation therapy. In one embodiment, the Fc variant of the present invention may be administered in conjunction with one or more antibodies, which may or may not comprise an Fc variant of the present invention. In accordance with another embodiment of the invention, the Fc variant of the present invention and one or more other anti-cancer therapies are employed to treat cancer cells ex vivo. It is contemplated that such ex vivo treatment may be useful in bone marrow transplantation and particularly, autologous bone marrow transplantation. It is of course contemplated that the Fc variants of the invention can be employed in combination with still other therapeutic techniques such as surgery. A variety of agents that may be co-administered with the Fc variants of the present invention are described in U.S. Ser. No. 11/124,620.

A variety of other therapeutic agents may find use for administration with the Fc variants of the present invention. In one embodiment, the IgG is administered with an anti-angiogenic agent. By "anti-angiogenic agent" as used herein is meant a compound that blocks, or interferes to some degree, the development of blood vessels. The anti-angiogenic factor may, for instance, be a small molecule or a protein, for example an antibody, Fc fusion, or cytokine, that binds to a growth factor or growth factor receptor involved in promoting angiogenesis. The anti-angiogenic factor herein is an antibody that binds to Vascular Endothelial Growth Factor (VEGF). In an alternate embodiment, the IgG is administered with a therapeutic agent that induces or enhances adaptive immune response, for example an antibody that targets CTLA-4. In an alternate embodiment, the IgG is administered with a tyrosine kinase inhibitor. By "tyrosine kinase inhibitor" as used herein is meant a molecule that inhibits to some extent tyrosine kinase activity of a tyrosine kinase. In an alternate embodiment, the Fc variants of the present invention are administered with a cytokine. By "cytokine" as used herein is meant a generic term for proteins released by one cell population that act on another cell as intercellular mediators.

Pharmaceutical compositions are contemplated wherein an Fc variant of the present invention and one or more therapeutically active agents are formulated. Formulations of the Fc variants of the present invention are prepared for storage by mixing the IgG having the desired degree of purity with optional pharmaceutically acceptable carriers, excipients or stabilizers (Remington's Pharmaceutical Sciences 16th edition, Osol, A. Ed., 1980, hereby entirely incorporated by reference), in the form of lyophilized formulations or aqueous solutions. The formulations to be used for in vivo administration are preferably sterile. This is readily accomplished by filtration through sterile filtration membranes or other methods. The Fc variants and other therapeutically active agents disclosed herein may also be formulated as immunoliposomes, and/or entrapped in microcapsules.

The concentration of the therapeutically active Fc variant in the formulation may vary from about 0.001 to 100 weight %. In certain embodiments, the concentration of the IgG is in the range of 0.003 to 1.0 molar. In order to treat a patient, a therapeutically effective dose of the Fc variant of the present invention may be administered. By "therapeutically effective dose" herein is meant a dose that produces the effects for which it is administered. The exact dose will depend on the purpose of the treatment, and will be ascertainable by one skilled in the art using known techniques. Dosages may range from 0.001 to 100 mg/kg of body weight or greater, for example 0.1, 1, 10, or 50 mg/kg of body weight, with 1 to 10 mg/kg being preferred. As is known in the art, adjustments for protein degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

Administration of the pharmaceutical composition comprising an Fc variant of the present invention, preferably in the form of a sterile aqueous solution, may be done in a variety of ways, including, but not limited to, orally, subcutaneously, intravenously, intranasally, intraotically, transdermally, topically (e.g., gels, salves, lotions, creams, etc.), intraperitoneally, intramuscularly, intrapulmonary (e.g., AERx® inhalable technology commercially available from Aradigm, or Inhance® pulmonary delivery system commercially available from Inhale Therapeutics), vaginally, parenterally, rectally, or intraocularly.

EXAMPLES

Examples are provided below to illustrate the present invention. These examples are not meant to constrain the present invention to any particular application or theory of operation.

Example 1

Design of Fc Variants with Selective FcγR Affinity

Figure 4:
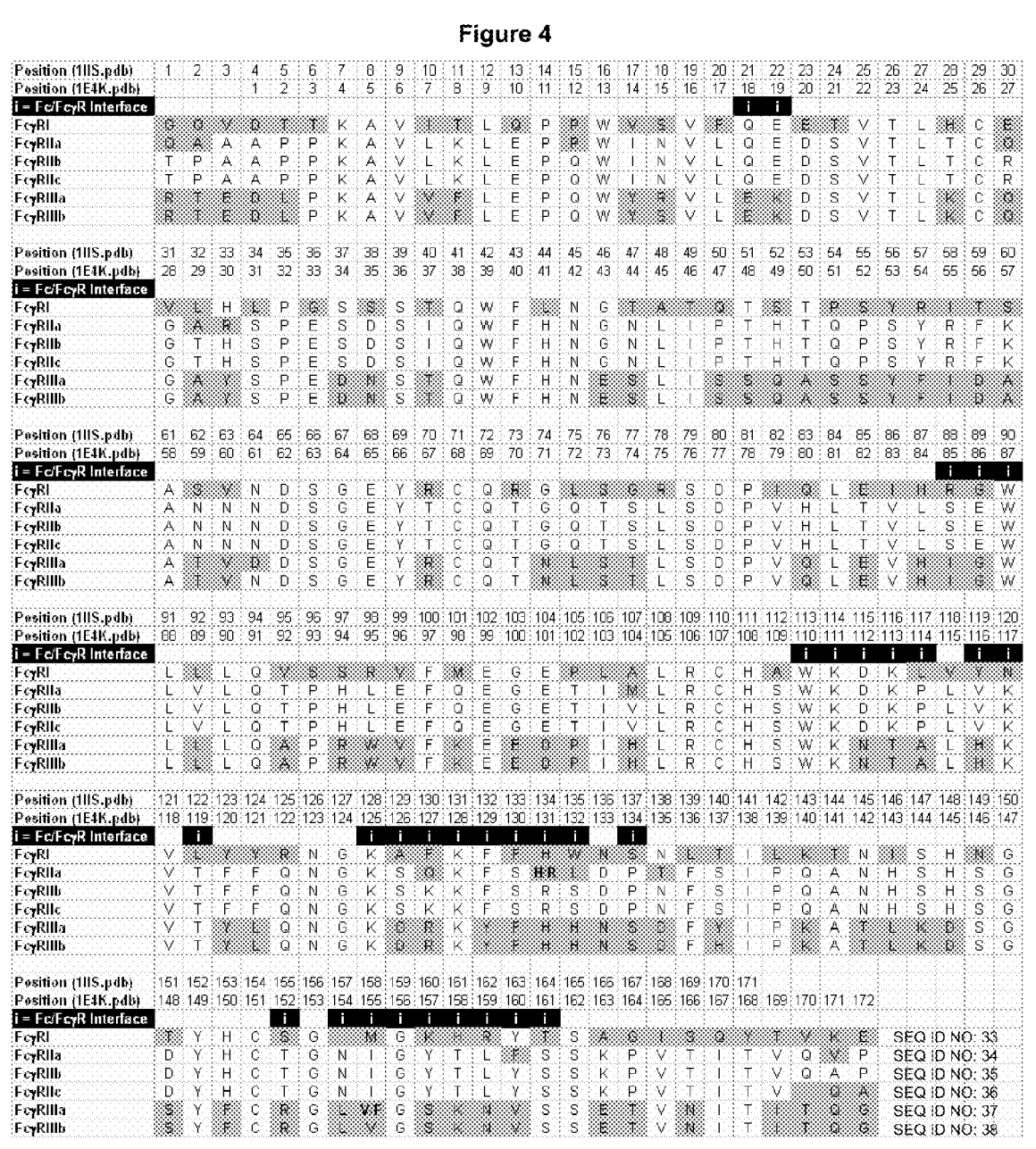

Sequence and structural analysis of the Fc/FcγR interface was carried out for the different human FcγRs. A central goal was to generate variants with selectively increased affinity for the activating receptors FcγRI, FcγRIIa, FcγRIIc, and FcγRIIIa relative to the inhibitory receptor FcγRIIb, and selectively increased affinity for FcγRIIb relative to the activating receptors. FIG. 4 shows an alignment of the sequences of the human FcγRs, highlighting the differences from FcγRIIb and positions at the Fc interface. The analysis indicates that although there is extensive homology among the human FcγRs, there are significant differences. Particularly relevant are differences at the Fc binding interface that may be capitalized on to engineer selective Fc variants.

The utility of this analysis is illustrated using the example of FcγRIIa vs. FcγRIIb. Engineering an Fc variant that selectively improves binding to FcγRIIa relative to FcγRIIb is potentially the most challenging embodiment of the present invention, due principally to the high sequence homology of these two receptors, particularly at the Fc/FcγR interface. FIG. 4 shows that there are 3 or 4 differences between FcγRIIb and FcγRIIa (depending on allotype) that distinguish binding of these receptors to the Fc region (FIG. 4). These include differences at 127 (FcγRIIa is Gln, FcγRIIb is Lys), 131 (FcγRIIa is either His or Arg depending on the allotype, FcγRIIb is an Arg), 132 (FcγRIIa is Leu, FcγRIIb is Ser), and 160 (FcγRIIa is Phe, FcγRIIb is Tyr). FcγR numbering here is according to that provided in the 1E4K pdb structure for FcγRIIIb. Mapping of these differences onto the Fc/FcγRIIIb complex (FIG. 5) reveals that Fc residues that interact with these FcγR residues occur at Fc positions 235-237, 328-330, and 332 on the A chain and at positions 235-239, 265-270, 295-296, 298-299, and 325-329 on the B chain in the 1E4K pdb structure (FcγRs bind asymmetrically to the Fc homodimer). Thus Fc positions 235-239, 265-270, 295-296, 298-299, 325-330, and 332 are positions that may be modified to obtain Fc variants with selectively increased affinity FcγRIIa relative to FcγRIIb. A similar analysis can be carried out for selectively altering affinity to one or more of the other activating receptors relative to the inhibitory receptor, for example for selectively improving affinity for FcγRIIIa relative to FcγRIIb, or conversely for selectively improving affinity for FcγRIIb relative to FcγRIIIa.

FcγR binding data provided in FIG. 41 of U.S. Ser. No. 11/124,620, hereby entirely incorporated by reference, indicate that indeed amino acid modification at some of these positions provide selective enhancement or reduction in FcγR affinity. For example G236S provides a selective enhancement to FcγRII's (FcγRIIa, FcγRIIb, and FcγRIIc) relative to FcγRI and FcγRIIIa, with a somewhat greater enhancement to FcγRIIa relative to FcγRIIb and FcγRIIc. G236A, however, is highly selectively enhanced for FcγRIIa, not only with respect to FcγRI and FcγRIIIa, but also over FcγRIIb and FcγRIIc. Selective enhancements and reductions are observed for a number of Fc variants, including a number of substitutions occurring at the analyzed above, namely 235-239, 265-270, 295-296, 298-299, 325-330, and 332. Although substitutions at some of these positions have been characterized previously (U.S. Pat. No. 5,624,821; Lund et al., 1991, J Immunol 147(8):2657-2662; U.S. Pat. No. 6,737, 056; Shields et al., 2001, J Biol Chem 276(9): 6591-6604), such substitutions have not been characterized with respect to their affinities for the full set of human activating and inhibitory FcγRs.

Example 2

Screening of Fc Variants

Amino acid modifications were engineered at these positions to generate variants with selective FcγR affinity. Fc variants were engineered in the context of the anti-CD20 antibody PRO70769 (PCT/US2003/040426, hereby entirely incorporated by reference). The genes for the variable regions of PRO70769 (SEQ IDs NO:1 and NO:2, FIGS. 27a and 27b) were constructed using recursive PCR, and subcloned into the mammalian expression vector pcDNA3.1Zeo (Invitrogen) comprising the full length light kappa (Cκ) and heavy chain IgG1 constant regions. Amino acid substitutions were constructed in the variable region of the antibody in the pcDNA3.1Zeo vector using quick-change mutagenesis techniques (Stratagene). DNA was sequenced to confirm the fidelity of the sequences. Plasmids containing heavy chain gene (VH-CH1-CH2-CH3) (wild-type or variants) were co-transfected with plasmid containing light chain gene (VL-Cκ) into 293T cells. Media were harvested 5 days after transfection, and antibodies were purified from the supernatant using protein A affinity chromatography (Pierce).

Binding affinity to human FcγRs by Fc variant anti-CD20 antibodies was measured using a competitive AlphaScreen™ assay. The AlphaScreen is a bead-based luminescent proximity assay. Laser excitation of a donor bead excites oxygen, which if sufficiently close to the acceptor bead will generate a cascade of chemiluminescent events, ultimately leading to fluorescence emission at 520-620 nm. The AlphaScreen was applied as a competition assay for screening the antibodies. Wild-type IgG1 antibody was biotinylated by standard methods for attachment to streptavidin donor beads, and tagged FcγR was bound to glutathione chelate acceptor beads. In the absence of competing Fc polypeptides, wild-type antibody and FcγR interact and produce a signal at 520-620 nm. Addition of untagged antibody competes with wild-type Fc/FcγR interaction, reducing fluorescence quantitatively to enable determination of relative binding affinities.

In order to screen for Fc/FcγR binding, the extracellular regions of human FcγRs were expressed and purified. The extracellular regions of these receptors were obtained by PCR from clones obtained from the Mammalian Gene Collection (MGC), or generated de novo using recursive PCR. To enable purification and screening, receptors were fused C-terminally with either a His tag, or with His-glutathione S-Transferase (GST). Tagged FcγRs were transfected into 293T cells, and media containing secreted receptor were harvested 3 days later and purified using Nickel chromatography. Additionally, some His-tagged FcγRs were purchased commercially from R&D Systems.

Competition AlphaScreen data were acquired for binding of the Fc variants to human FcγRI, R131 FcγRIIa, H131

Figure 6A:
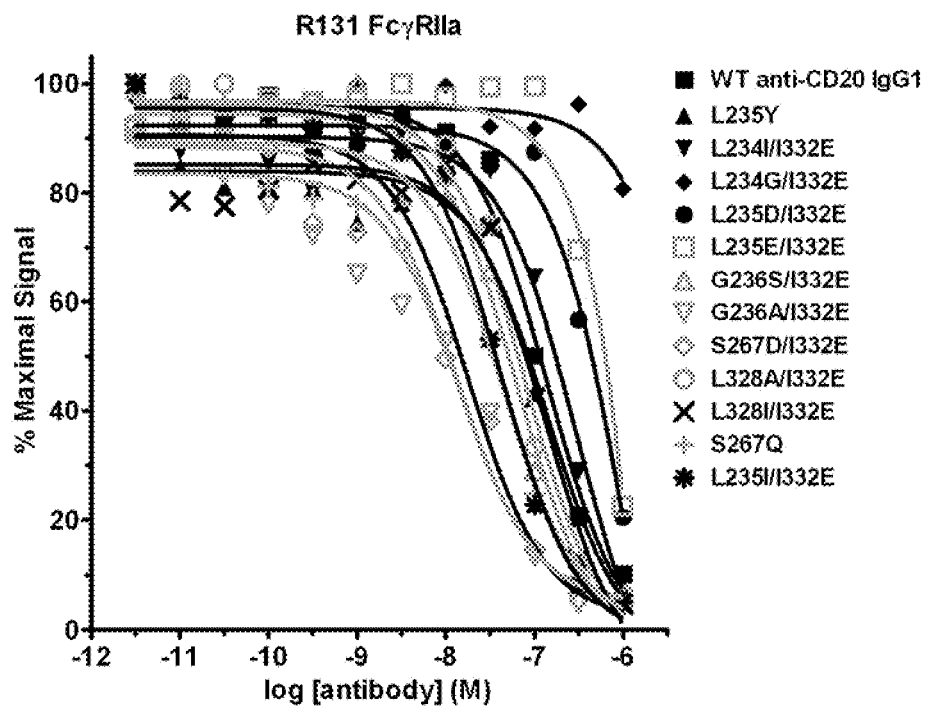
FIG. 6. Binding of select anti-CD20 Fc variants to human R131 FcγRIIa (FIG. 6a) and FcγRIIb (FIG. 6b) as measured by competition AlphaScreen™ assay. In the presence of competitor antibody (Fc variant or WT) a characteristic inhibition curve is observed as a decrease in luminescence signal. The binding data were normalized to the maximum and minimum luminescence signal for each particular curve, provided by the baselines at low and high antibody concentrations respectively. The curves represent the fits of the data to a one site competition model using nonlinear regression.
Figure 6B:
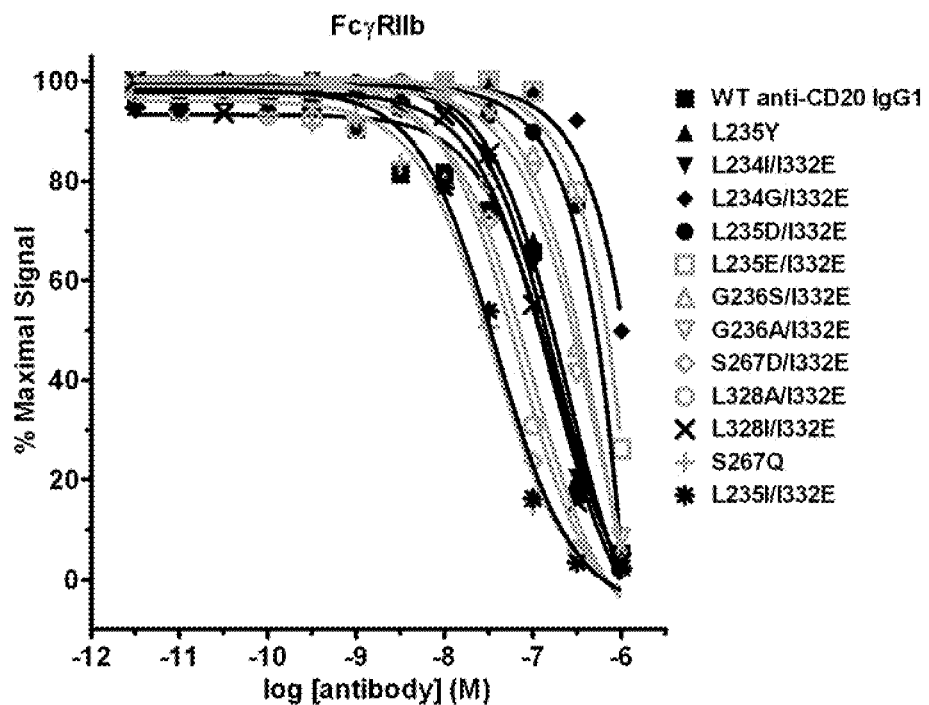

FcγRIIa, FcγRIIb, and V158 FcγRIIIa. FIG. 6 show the data for binding of select antibody variants to the human receptors R131 FcγRIIa (FIG. 6a) and FcγRIIb (FIG. 6b). The data were fit to a one site competition model using nonlinear regression, and these fits are represented by the curves in the figure. These fits provide the inhibitory concentration 50% (IC50) (i.e. the concentration required for 50% inhibition) for each antibody, thus enabling the relative binding affinities relative to WT to be determined. FIG. 7 provides the IC50's and Fold IC50's relative to WT for fits to these binding curves for all of the anti-CD20 antibody Fc variants tested. The data support the analysis above that substitution at positions within the binding region defined by 235-239, 265-270, 295-296, 298-299, 325-330, and 332 may be involved in distinguishing the different affinities of the Fc region for the different FcγRs. For example as shown by the data, variants comprising modifications at 235, 236, 267, and 328 have varying affinity improvements and reductions relative to the parent antibody for the different FcγRs, including even the highly homologous FcγRIIa and FcγRIIb. It is notable that, with respect to engineering optimal FcγR selectivity for antibodies and Fc fusions, single variants do not necessarily completely provide favorable FcγR affinities (see for example Table 1). For example although the single variant G236A provides selectively improved affinity to FcγRIIa relative to FcγRIIb, it is reduced in affinity for both the other activating receptors FcγRI and FcγRIIIa. However combination of this substitution with other modifications that provide increased affinity to these other activating receptors, for example I332E, results in an Fc variant with a promising FcγR affinity profile, namely increased affinity for FcγRIIa and FcγRIIIa relative to the inhibitory receptor FcγRIIb.

Figure 8:
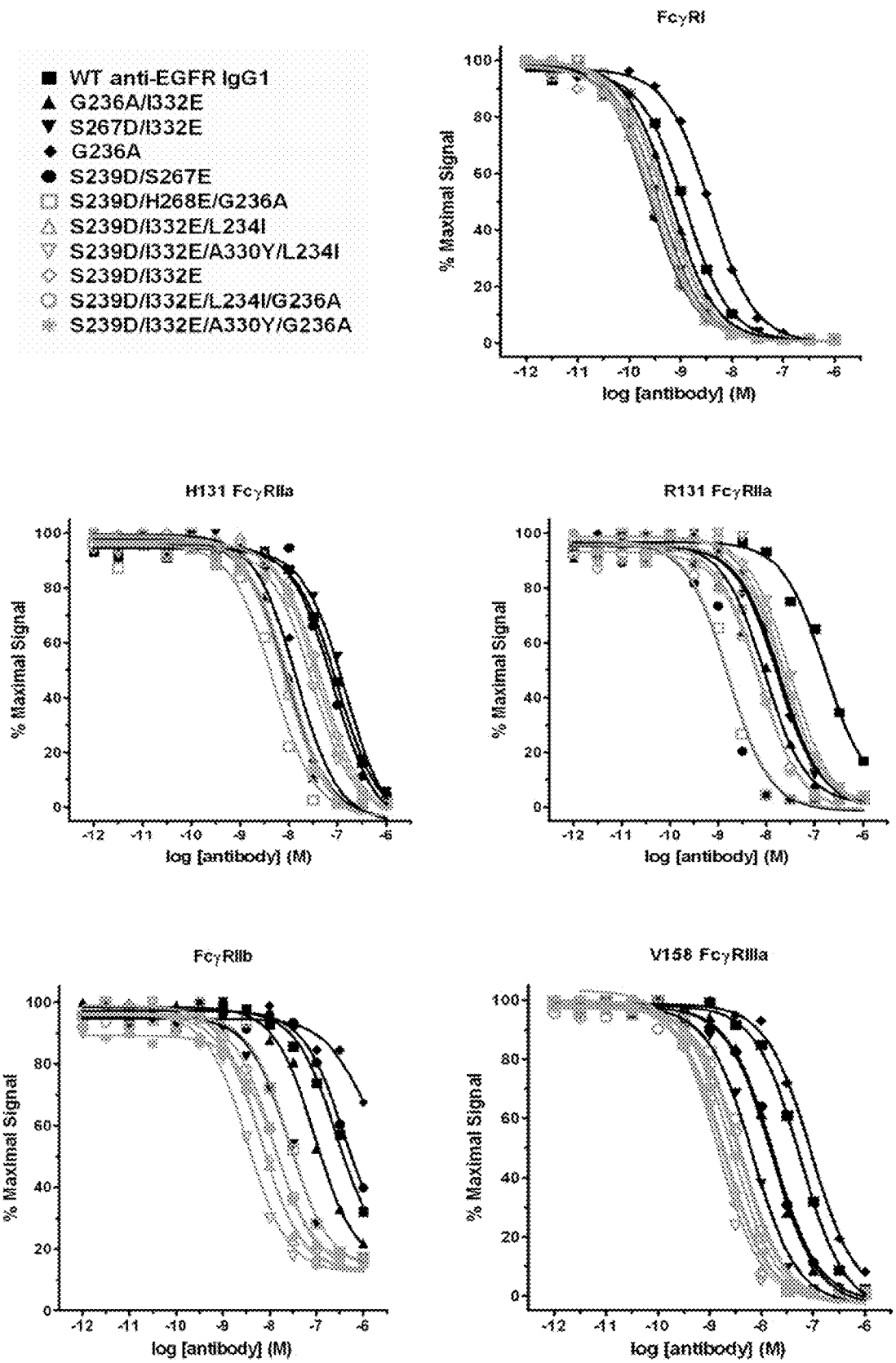
FIG. 8. Binding of select anti-EGFR Fc variants to human FcγRI, R131 and H131 FcγRIIa, FcγRIIb, and V158 FcγRIIIa as measured by competition AlphaScreen assay.

Based on these results, a number of additional Fc variants were constructed in the context of the anti-EGFR antibody H4.40/L3.32 C225 (SEQ IDs NO:3 and NO:4, FIGS. 27c and 27d) as disclosed in U.S. Ser. No. 60/778,226, filed Mar. 2, 2006, entitled "Optimized anti-EGFR antibodies", herein expressly incorporated by reference). Antibody variants were constructed in the IgG1 pcDNA3.1Zeo vector, expressed in 293T cells, and purified as described above. Binding affinity to human FcγRs by Fc variant anti-EGFR antibodies was measured using a competition AlphaScreen assay as described above. FIG. 8 shows binding data for the Fc variants to human FcγRI, R131 FcγRIIa, H131 FcγRIIa, FcγRIIb, and V158 FcγRIIIa. FIG. 9 provides the IC50's and Fold IC50's relative to WT for fits to these binding curves for all of the anti-EGFR antibody Fc variants tested. The data indicate that it is possible to combine modifications at the aforementioned positions to generate variants with selectively improved affinity for one or more human activating receptors relative to the human inhibitory receptor FcγRIIb.

Based on these results, a number of additional Fc variants were constructed in the context of the anti-EpCAM antibody H3.77/L3 17-1A (SEQ IDs NO:5 and NO:6, FIGS. 27e and 27f) as disclosed in U.S. Ser. No. 11/484,183 and U.S. Ser. No. 11/484,198, filed in Jul. 10, 2006, herein expressly incorporated by reference). Antibody variants were constructed in the pcDNA3.1Zeo vector as described above. Antibody variants were constructed in the context of the IgG1 heavy chain and/or in the context of a novel IgG molecule referred to as IgG(hybrid) (SEQ ID NO:14, FIG. 28f), described in U.S. Ser. No. 11/256,060, filed Oct. 21, 2005, hereby entirely incorporated by reference. Antibodies were expressed in 293T cells, and purified as described above.

Binding affinity to human FcγRs by Fc variant anti-EpCAM antibodies was measured using surface plasmon resonance (SPR), also referred to as BIAcore. SPR measurements were performed using a BIAcore 3000 instrument (BIAcore, Uppsala Sweden). Running buffer was 10 mM HEPES pH 7.4, 150 mM NaCl, 3 mM EDTA, 0.005% v/v Surfactant P20 (HBS-EP, BIAcore), and chip regeneration buffer was 10 mM glycine-HCl pH 1.5. 100 nM WT or variant anti-EpCAM antibody was bound to the protein A/G CM5 chip in HBS-EP at 1 µl/min for 5 min. 50 µl FcγR-His analyte, in serial dilutions between 30 and 1000 nM, was injected in HBS-EP at 25 µl/min for 2 minutes association, followed by a dissociation phase with buffer alone. Data were normalized for baseline response, obtained from a cycle with antibody and buffer alone. Response sensorgrams were fit to a 1:1 Langmuir binding model within BIAevaluation software, providing the association (ka) and dissociation (kd) rate constants, and the equilibrium dissociation constant (KD).

Figure 10:
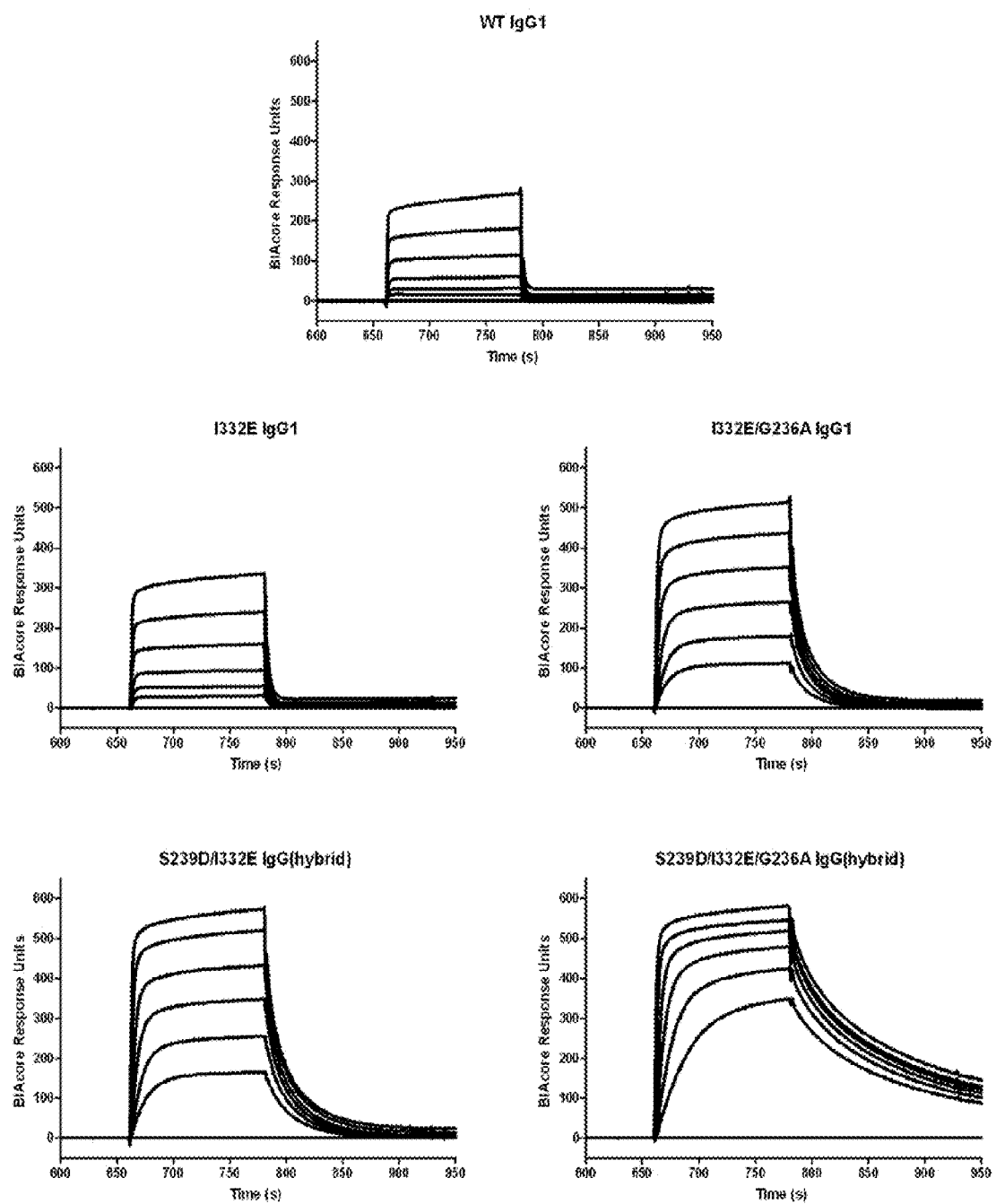
FIG. 10. Surface Plasmon Resonance (SPR) (BIAcore) sensorgrams of binding of select anti-EpCAM Fc variants to human R131 FcγRIIa.

FIG. 10 shows SPR sensorgrams for binding of select anti-EpCAM Fc variants to human R131 FcγRIIa. FIG. 11 shows kinetic and equilibrium constants obtained from the fits of the SPR data for all of the receptors, well as the calculated Fold(KD) relative to WT and the negative log of the KD (-log(KD)). Here Fold(KD) for a given variant to a given receptor is defined as:

$$\text{Fold}(KD)_{Fc\gamma R} = KD_{WT}/KD_{variant} \quad \text{Equation 1:}$$

Figure 12:
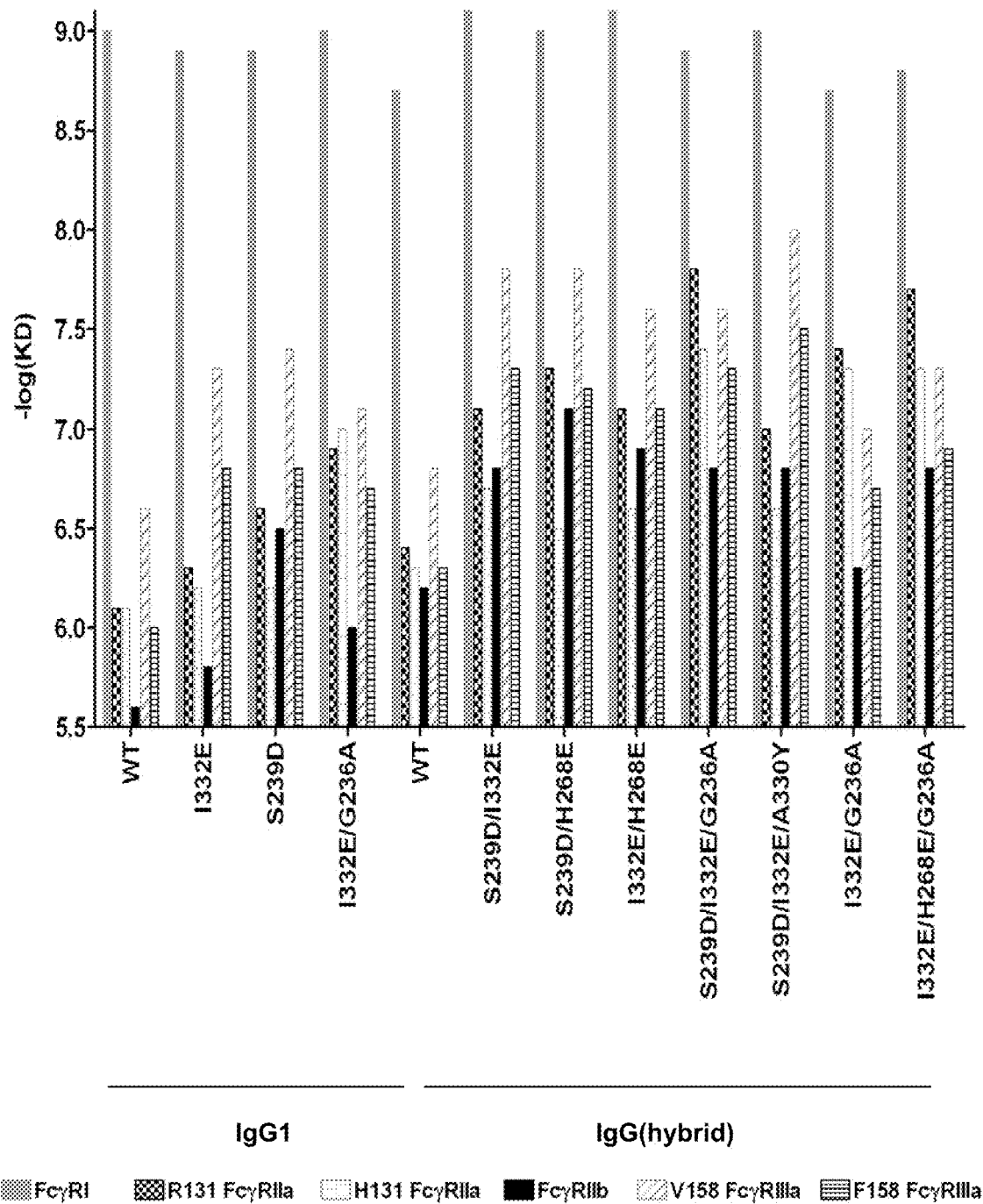
FIG. 12. Plot of the negative log of the KD for binding of select anti-EpCAM Fc variants to human FcγRI, R131 FcγRIIa, H131 FcγRIIa, FcγRIIb, and V158 FcγRIIIa.

A Fold(KD) greater than 1 for a given receptor indicates that the variant improves affinity relative to the WT parent, whereas a Fold(KD) less than 1 indicates the variant reduces affinity relative to the WT parent. FIG. 12 provides a plot of the negative log of the KD for binding of select anti-EpCAM Fc variants to the set of human FcγRs. Here greater -log(KD) on the y-axis corresponds to tighter affinity for the receptor. In order to better view the impact of the substitutions on FcγR specificity, the activating versus inhibitory FcγR affinity differences are plotted for FcγRIIa vs. FcγRIIb and FcγRIIIa vs. FcγRIIb. Here for each variant the -log(KD) for its binding to FcγRIIb is subtracted from the -log(KD) for it binding to the activating receptor, providing a direct measure of FcγR selectivity of the variants. Notably, all variants comprising the G236A substitution, including I332E/G236A, S239D/I332E/G236A, and I332E/H268E/G236A have favorable FcγRIIa:FcγRIIb selectivity relative to, respectively, the I332E, S239D/I332E, and I332E/H268E variants alone. Thus the results show that suboptimal G236A substitution can be combined with other substitutions that have favorable FcγR affinities to generate Fc variants with the most optimal FcγR affinity profiles.

In order to calculate the selective enhancement in affinity for the activating receptors relative to the inhibitory receptor FcγRIIb for each variant, this analysis must be carried out with respect to the parent antibody, either WT IgG1 or WT IgG(hybrid) in this example. The selective enhancement in affinity for FcγRIIa relative to FcγRIIb provided by an Fc variant is defined as Fold(KD)$_{Fc\gamma RIIa}$:Fold(KD)$_{Fc\gamma RIIb}$, also written as Fold(KD)$_{Fc\gamma RIIa}$/Fold(KD)$_{Fc\gamma RIIb}$. This value is calculated as follows:

$$\text{Fold}(KD)_{Fc\gamma RIIa}:\text{Fold}(KD)_{Fc\gamma RIIb} = \text{Fold}(KD)_{Fc\gamma RIIa}/\text{Fold}(KD)_{Fc\gamma RIIb} \quad \text{Equation 2:}$$

Likewise the selective enhancement in affinity for FcγRIIIa relative to FcγRIIb provided by an Fc variant is calculated as follows:

$$\text{Fold}(KD)_{Fc\gamma RIIIa}:\text{Fold}(KD)_{Fc\gamma RIIb} = \text{Fold}(KD)_{Fc\gamma RIIIa}/\text{Fold}(KD)_{Fc\gamma RIIb} \quad \text{Equation 3:}$$

Figure 13C:
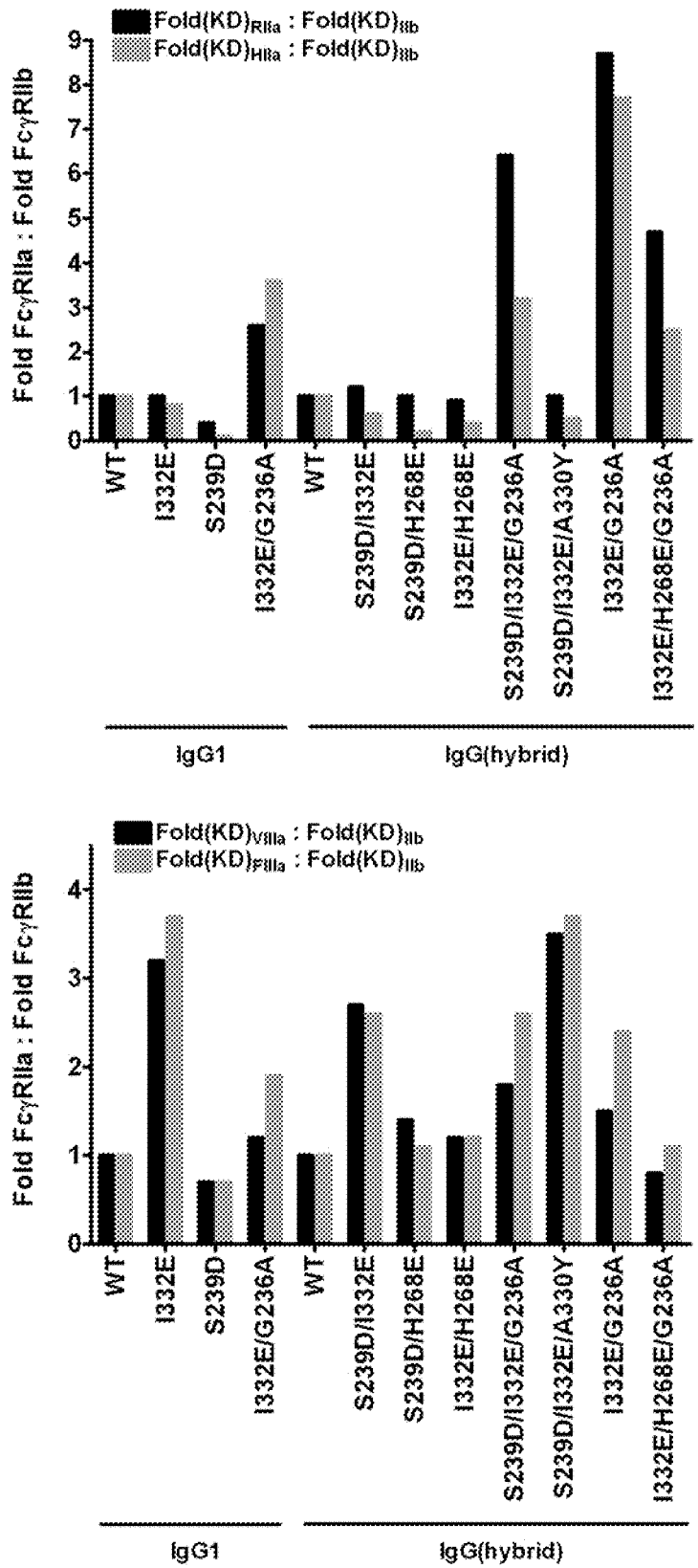
FIG. 13c provides a plot of these data.

FIG. 13b provides these values for both R131 and H131 isoforms of FcγRIIa (RIIa and HIIa for brevity), and for both V158 and F158 isoforms of FcγRIIIa (VIIIa and FIIIa for brevity). FIG. 13c provides a plot of these data. The results show that the Fc variants of the invention provide up to 9-fold selective enhancements in affinity for binding to the activating receptor FcγRIIa relative to the inhibitory receptor FcγRIIb, and up to 4-fold selective enhancements in affinity for binding to the activating receptor FcγRIIIa relative to the inhibitory receptor FcγRIIb.

Example 3

Performance of Fc Variants in Cell-Based Assays

Figure 14:
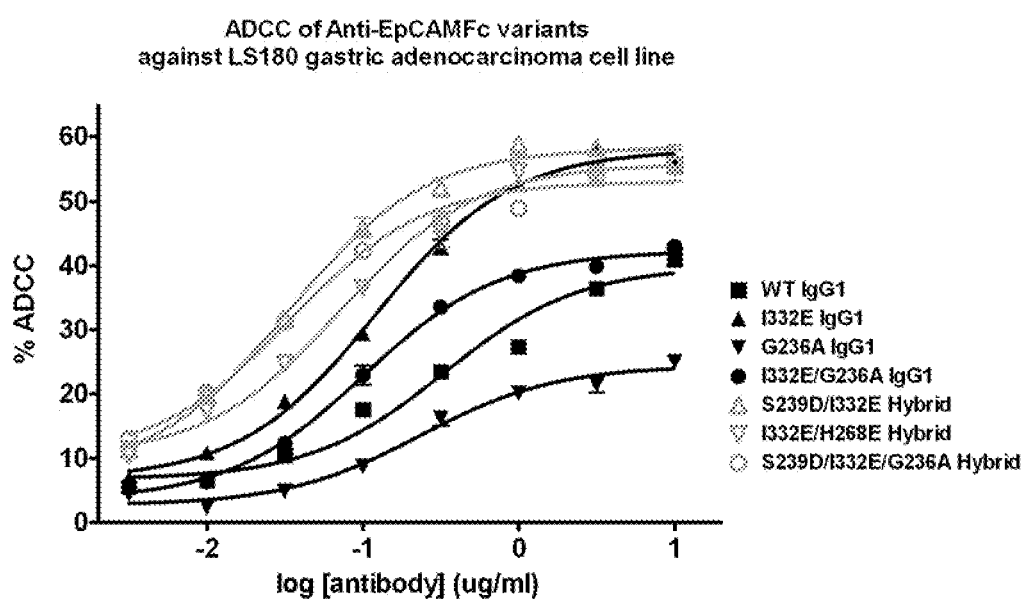
FIG. 14. Cell-based ADCC assays of anti-epCAM Fc variants.

A central goal of improving the activating FcγR vs. inhibitory FcγR profile of an antibody or Fc fusion was to enhance its FcγR-mediated effector function in vitro and ultimately in vivo. To investigate the capacity of antibodies comprising the Fc variants of the present invention to carry out FcγR-mediated effector function, in vitro cell-based ADCC assays were run using human PBMCs as effector cells. ADCC was measured by the release of lactose dehydrogenase using a LDH Cytotoxicity Detection Kit (Roche Diagnostic). Human PBMCs were purified from leukopacks using a ficoll gradient, and the EpCAM$^+$ target gastric adenocarcinoma line LS180. Target cells were seeded into 96-well plates at 10,000 cells/well, and opsonized using Fc variant or WT antibodies at the indicated final concentration. Triton X100 and PBMCs alone were run as controls. Effector cells were added at 40:1 PBMCs:target cells, and the plate was incubated at 37° C. for 4 hrs. Cells were incubated with the LDH reaction mixture, and fluorescence was measured using a Fusion™ Alpha-FP (Perkin Elmer). Data were normalized to maximal (triton) and minimal (PBMCs alone) lysis, and fit to a sigmoidal dose-response model. FIG. 14 provides these data for select Fc variant antibodies. The G236A variant mediates reduced ADCC relative to WT, due likely to its reduced affinity for FcγRIIIa and/or FcγRI. ADCC in PBMCs is potentially dominated by NK cells, which express only FcγRIIIa, although in some cases they can express FcγRIIc. Thus the reduced ADCC of the G236A single variant is consistent with its reduced affinity for this receptor. However, combination of the G236A substitution with modifications that improve affinity for these activating receptors, for example including but not limited to substitutions at 332 and 239, provide substantially improved ADCC relative to the parent WT antibody.

Monocyte-derived effector cells, including for example macrophages, express not only FcγRIIIa, but also FcγRI, FcγRIIa, and the inhibitory receptor FcγRIIb. Macrophages are phagocytes that act as scavengers to engulf dead cells, foreign substances, and other debris. Importantly, macrophages are professional antigen presenting cells (APCs), taking up pathogens and foreign structures in peripheral tissues, then migrating to secondary lymphoid organs to initiate adaptive immune responses by activating naive T-cells. Unlike NK cells, macrophages express the range of FcγRs, and thus their activation and function may be dependent on engagement of antibody immune complexes with receptors other than only FcγRIIIa.

Figure 15A:
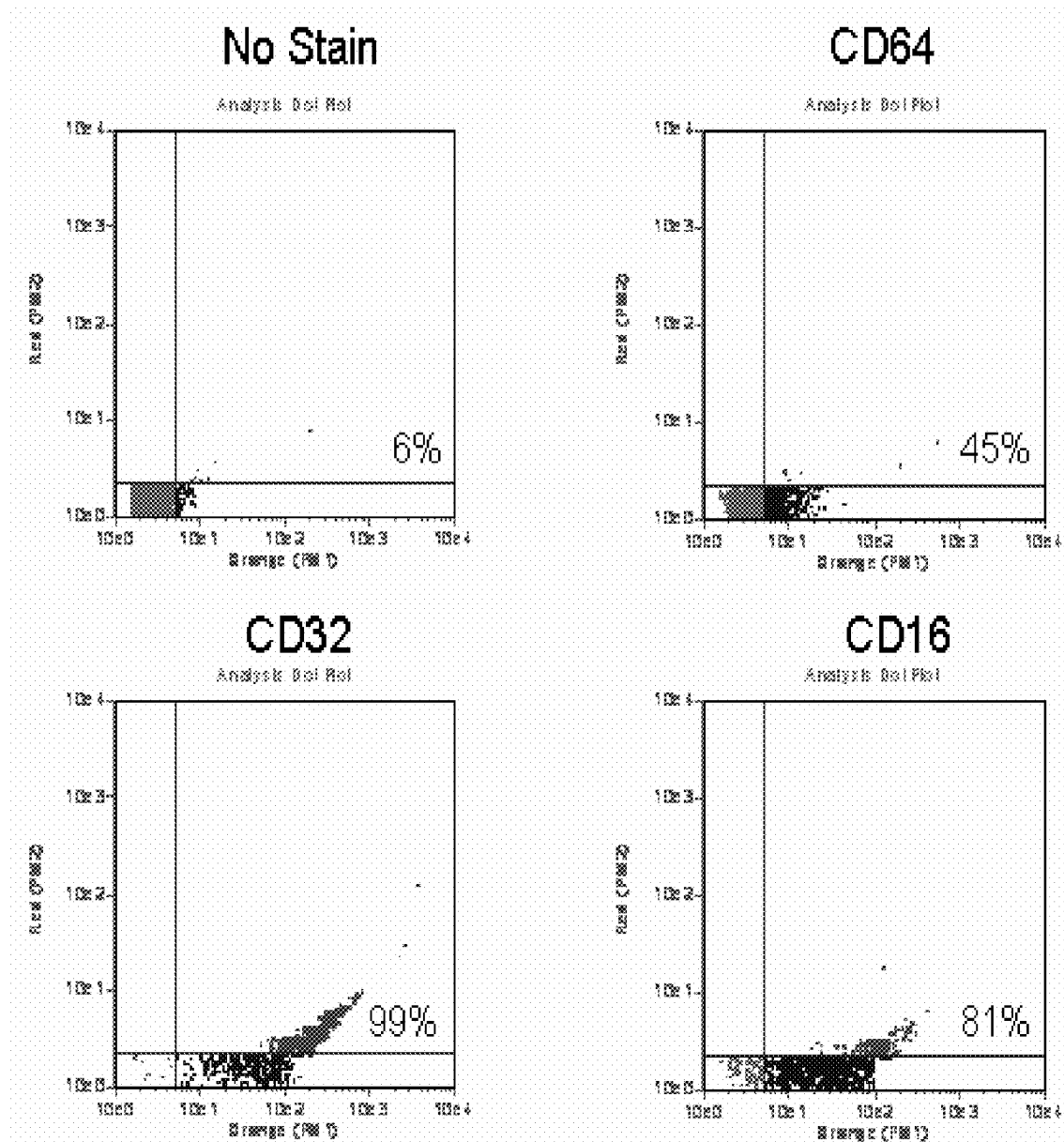
FIG. 15a. Receptor expression density of FcγRI (CD64), FcγRIIa and FcγRIIb (CD32), and FcγRIIIa (CD16) on monocyte-derived macrophages.

A cell-based ADCP assay was carried out to evaluate the capacity of the Fc variants to mediate phagocytosis. Monocytes were purified from PBMCs and differentiated into macrophages in 50 ng/ml M-CSF for 5 days. Quantitated receptor expression density of FcγRI (CD64), FcγRIIa and FcγRIIb (CD32), and FcγRIIIa (CD16) on these cells was determined with standard flow cytometry methods using PE (orange)-labeled anti-FcγRs and biotinylated PE-Cy5-labeled antibodies against macrophage markers CD11b and CD14. PE-conjugated anti-CD64 (Clone 10.1) was purchased from eBioscience, PE-conjugated anti-CD32 (Clone 3D3) and PE-conjugated anti-CD16 (Clone 3G8) were purchased from BD Bioscience. Biotinylated anti-CD14 (TUK4) was purchased from Invitrogen, and biotinylated anti-CD11b (Clone ICRF44) was purchased from BD Bioscience. Secondary detection was performed with streptavidin PE-Cy5 obtained from Biolegend. Cytometry was carried out on a Guava Personal Cell Analysis-96 (PCA-96) System (Guava Technologies). FIG. 15a shows that the monocyte-derived macrophages (MDM) express high levels of FcγRII (99%) and FcγRIII (81%), and moderate (45%) levels of FcγRI. The inability to distinguish between FcγRIIa and FcγRIIb is due to the unavailability of commercial antibodies that selectively bind these two receptors.

For ADCP assays with MDM as effector cells, target EpCAM$^+$ LS180 cells were labeled with PKH26 and plated in a 96-well round bottom plate at 25 000 cells/well. Antibodies (WT and Fc variants) were added to wells at indicated concentrations, and antibody opsinized cells were incubated for approximately 30 minutes prior to the addition of effector cells. Monocyte derived macrophages (MDM) were added to each well at approximately 4:1 effector to target ratio, and the cells were incubated overnight. Cells were washed and treated with HyQtase. MDM were stained with biotinylated CD11b and CD14, followed by a secondary stain with Streptavidin PE-Cy5. Cells were fixed in 1% paraformaldehyde and read on the Guava flow cytometer.

Figure 15B:
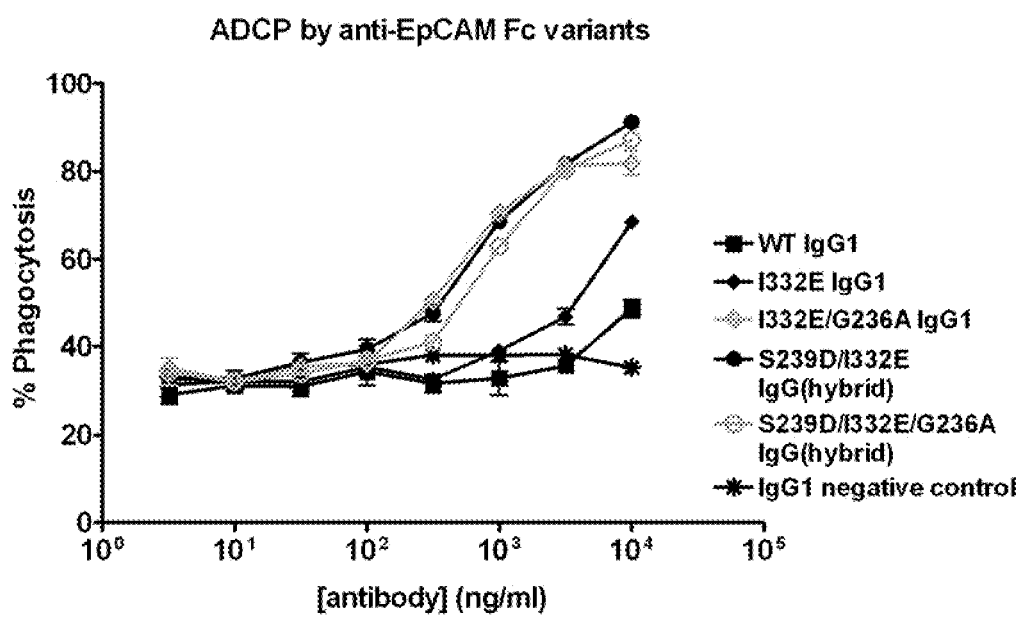
FIGS. 15b-15c. Cell-based ADCP assay of anti-epCAM Fc variants.
Figure 15C:
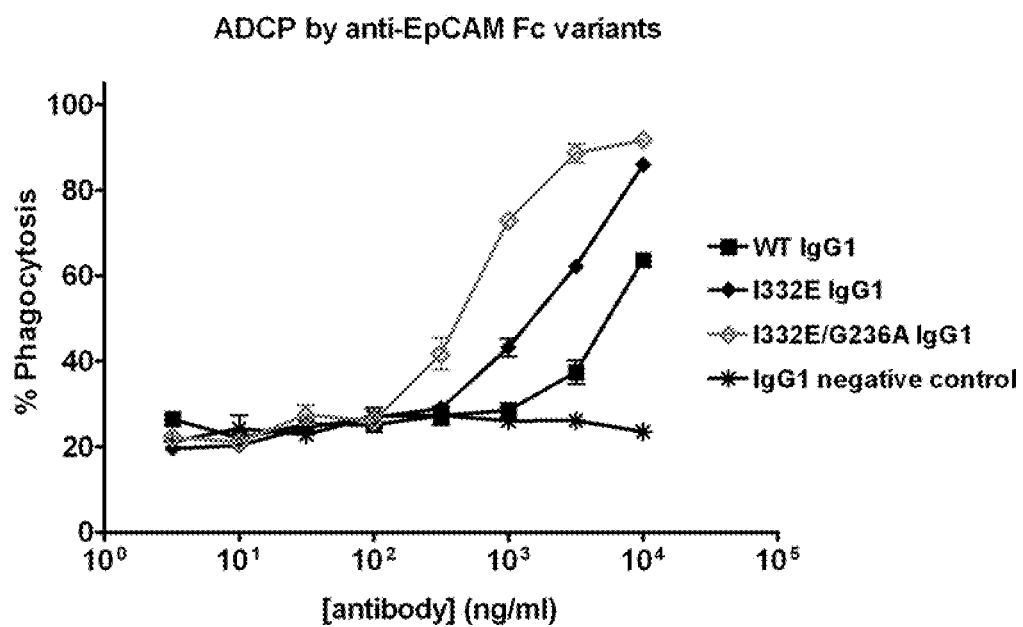

FIG. 15b shows the results of an ADCP assay of select anti-EpCAM Fc variants in the presence of macrophages. FIG. 15c show a repeat experiment with some of these variants. The data show that the improved FcγRII:FcγRIIb profile of the I332E/G236A variant relative to the I332E single variant provides enhanced phagocytosis. Interestingly, G236A does not improve phagocytosis of the S239D/I332E variant. The reason(s) for this result are not clear, but may be due in part to the lower FcγRI binding affinity of S239D/I332E/G236A relative to S239D/I332E, whereas I332E/G236A does not have compromised FcγRI affinity relative to I332E alone. Alternatively, it may be that the inhibitory receptor FcγRIIb, the affinity for which is greater in the S239D/I332E and S239D/I332E/G236A variants relative to the I332E and I332E/G236A variants, establishes an absolute threshold of activation/repression. That is, regardless of how much affinity to FcγRIIa is improved, at a certain level of FcγRIIb engagement cellular activation and effector function is inhibited.

Dendritic cells (DCs) are professional antigen presenting cells (APCs) that take up pathogens/foreign structures in peripheral tissues, then migrate to secondary lymphoid organs where they initiate adaptive immune responses by activating naive T-cells. Immature DCs endocytose either free or complexed antigens in the periphery, and this stimulus induces their maturation and migration to secondary lymphoid organs. Mature DCs expressing costimulatory molecules and produce various cytokines, including for example TNFα, to efficiently activate antigen-specific naive T-cells. DC-derived cytokines play a crucial role in shaping the adaptive response via determining polarization of T-cells towards either the Th1 or the Th2 phenotype (Bajtay et al., 2006, Immunol Letters 104: 46-52). Human DCs can express the various FcγRs depending on their source and activation state (Bajtay et al., 2006, Immunol Letters 104: 46-52). In contrast to circulating monocytic precursors to DCs, which can express the range of FcγRs, immature monocyte-derived DCs express primarily FcγRIIa and FcγRIIb. Recent data suggest that the relative engagement of FcγRIIa and FcγRIIb by immune complexes establishes a threshold of DC activation, mediating opposing effects on DC maturation and function (Boruchov et al., 2005, J Clin Invest 115(10):2914-23).

Figure 16A:
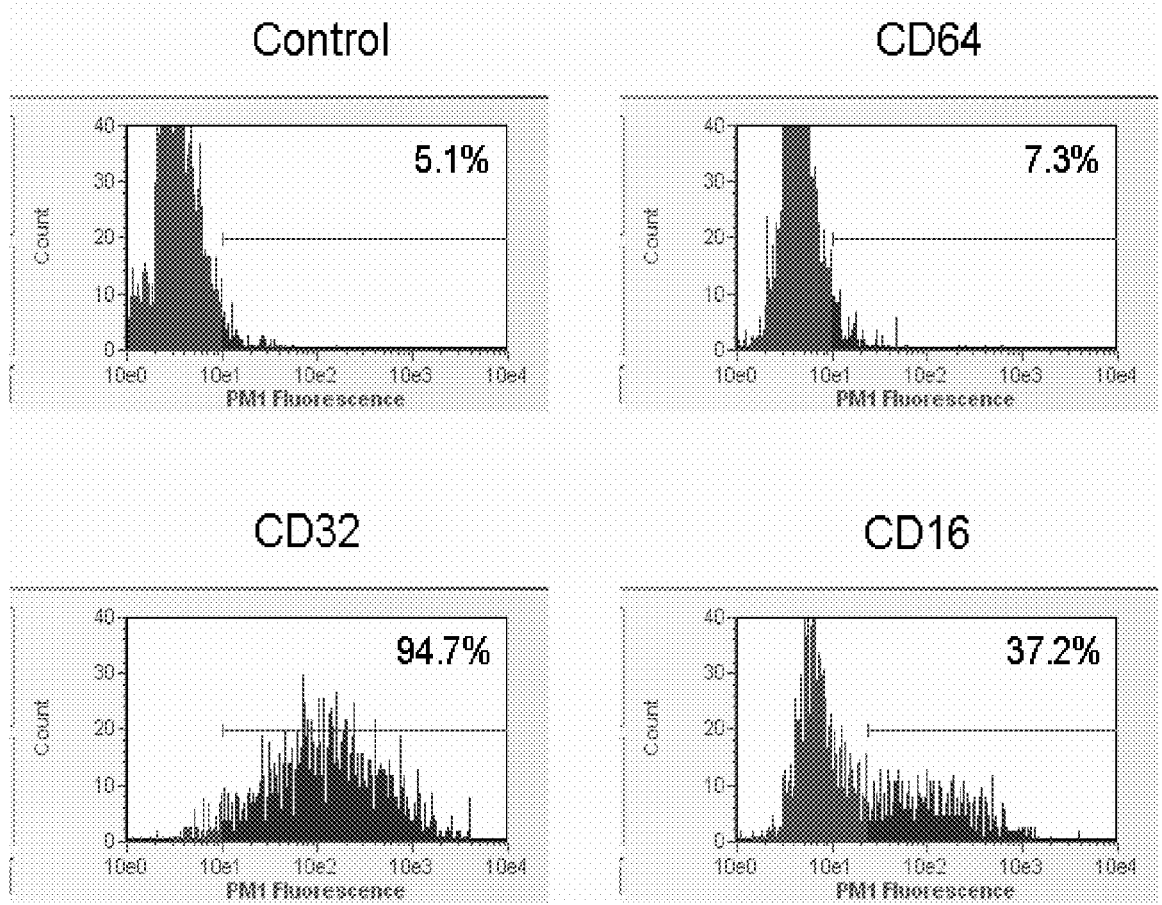
FIG. 16a shows the quantitated receptor expression density on monocyte-derived dendritic cells measured with antibodies against FcγRI (CD64), FcγRIIa and FcγRIIb (CD32), and FcγRIIIa (CD16) using flow cytometry. "Control" indicates no antibody was used and is a negative control. The diagrams show the percentage of cells labeled with PE-conjugated antibody against the indicated FcγR.

To evaluate the effect of the different FcγR affinity profiles on DC maturation, a cell-based assay was carried out using TNFα release to monitor DC activation. Dendritic cells (DCs) were generated from CD14+ sorted cells that were cultured in the presence of GM-CSF (1000 Units/ml or 100 ng/ml) and IL4 (500 Units/ml or 100 ng/ml) for six days. FcγRIIa and FcγRIIb (CD32), and FcγRIIIa (CD16) expression on these cells was determined with standard flow cytometry methods using PE-labeled anti-FcγRs. PE-conjugated anti-CD64 (Clone 10.1) was purchased from eBioscience, PE-conjugated anti-CD32 (Clone 3D3) and PE-conjugated anti-CD16 (Clone 3G8) were purchased from BD Bioscience. Cytometry was carried out on the Guava. FIG. 16a shows that the DCs used express high levels of FcγRII (94.7%), low to moderate levels of FcγRIII (37.2%), and low to no FcγRI (7.3%).

Figure 16B:
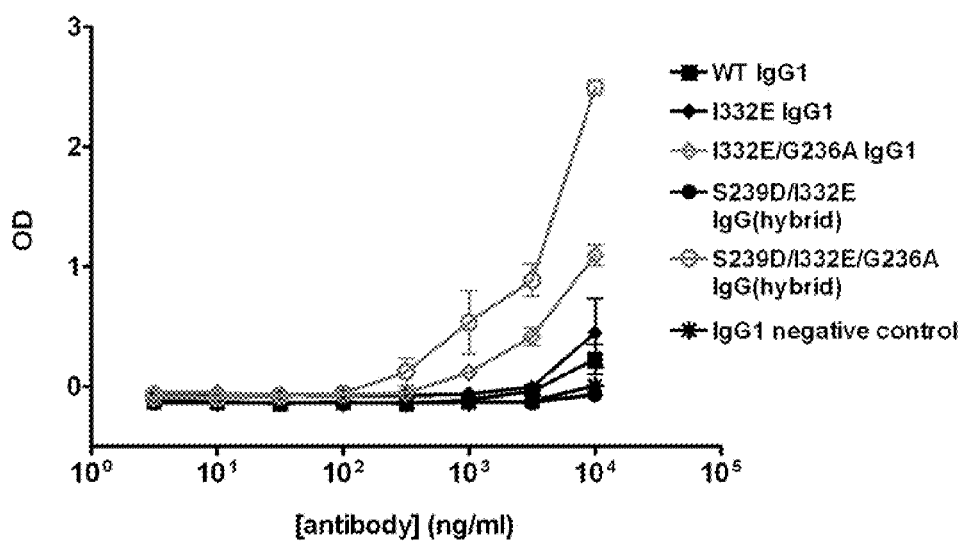
FIG. 16b shows the dose-dependent TNFα release by dendritic cells in the presence of WT and Fc variant antibodies and EpCAM+ LS180 target cells. The IgG1 negative control binds RSV and not EpCAM, and thus does not bind to the target cells.

For the DC activation assay, DCs were cultured in the presence of various concentrations of antibody and EpCAM+ LS180 cells overnight. Supernatants were harvested and tested for TNFα by ELISA. FIG. 16b shows the dose response curves for TNFα release by DCs in the presence of WT and Fc variant antibodies. The data show that DC activation is correlated roughly with the FcγRIIa:FcγRIIb affinity ratio (FIG. 13), consistent with the literature and the dominant expression of FcγRII receptors on the DCs used in the present assay. I332E and S239D/I332E mediate DC activation comparable with or lower than WT, in agreement with their FcγRIIa:FcγRIIb affinity profile. However addition of a substitution that selectively improves the FcγR affinity for FcγRIIa relative to FcγRIIb, in this case G236A, dramatically improves DC activation—I332E/G236A and S239D/I332E/G236A show enhanced DC activation relative to WT, I332E, and S239D/I332E. Together the macrophage phagocytosis and DC activation data are the first examples of the use of antibody Fc variants with improved FcRIIa:FcγRIIb affinity profiles to enhance the function of antigen presenting cells. Along with the ADCC data (FIG. 14), the cell-based results indicate that the most optimal engineered FcγR profile is selectively improved affinity for both FcγRIIa and FcγRIIIa relative to the inhibitory receptor FcγRIIb, for example as provided by the combination of S239D, I332E, and G236A substitutions.

Example 4

Preferred Fc Variants of the Invention

Taken together, the data provided in the present invention indicate that combinations of amino acid modifications at positions 235, 236, 237, 238, 239, 265, 266, 267, 268, 269, 270, 295, 296, 298, 299, 325, 326, 327, 328, 329, 330, and 332 provide promising candidates for selectively modifying the FcγR binding properties, the effector function, and potentially the clinical properties of Fc polypeptides, including antibodies and Fc fusions. In particular, Fc variants that selectively improve binding to one or more human activating receptors relative to FcγRIIb, or selectively improve binding to FcγRIIb relative to one or more activating receptors, may comprise a substitution, as described herein, selected from the group consisting of 234G, 234I, 235D, 235E, 235I, 235Y, 236A, 236S, 239D, 267D, 267E, 267Q, 268D, 268E, 293R, 295E, 324G, 324I, 327H, 328A, 328F, 328I, 330I, 330L, 330Y, 332D, and 332E. Additional substitutions that may also be combined include other substitutions that modulate FcγR affinity and complement activity, including but not limited to 298A, 298T, 326A, 326D, 326E, 326W, 326Y, 333A, 333S, 334L, and 334A (U.S. Pat. No. 6,737,056; Shields et al, Journal of Biological Chemistry, 2001, 276(9):6591-6604; U.S. Pat. No. 6,528,624; Idusogie et al., 2001, J. Immunology 166:2571-2572). Preferred variants that may be particularly useful to combine with variants of the present invention include those that comprise the substitutions 298A, 326A, 333A, and 334A. AlphaScreen data measuring the binding of Fc variants comprising these substitutions to the human activating receptors V158 and F158 FcγRIIIa and the inhibitory receptor FcγRIIb are shown in FIG. 17. Additional substitutions that may be combined with the FcγR selective variants of the present invention 247L, 255L, 270E, 392T, 396L, and 421K (U.S. Ser. No. 10/754,922; U.S. Ser. No. 10/902,588), and 280H, 280Q, and 280Y (U.S. Ser. No. 10/370,749), all of which are herein expressly incorporated by reference In particularly preferred embodiments of the invention, Fc variants of the present invention may be combined with Fc variants that alter FcRn binding. In particular, variants that increase Fc binding to FcRn include but are not limited to: 250E, 250Q, 428L, 428F, 250Q/428L (Hinton et al., 2004, J. Biol. Chem. 279(8): 6213-6216, Hinton et al. 2006 Journal of Immunology 176:346-356, U.S. Ser. No. 11/102,621, PCT/US2003/033037, PCT/US2004/011213, U.S. Ser. No. 10/822,300, U.S. Ser. No. 10/687,118, PCT/US2004/034440, U.S. Ser. No. 10/966,673 all entirely incorporated by reference), 256A, 272A, 286A, 305A, 307A, 311A, 312A, 376A, 378Q, 380A, 382A, 434A (Shields et al, Journal of Biological Chemistry, 2001, 276(9):6591-6604, U.S. Ser. No. 10/982, 470, U.S. Pat. No. 6,737,056, U.S. Ser. No. 11/429,793, U.S. Ser. No. 11/429,786, PCT/US2005/029511, U.S. Ser. No. 11/208,422, all entirely incorporated by reference), 252F, 252T, 252Y, 252W, 254T, 256S, 256R, 256Q, 256E, 256D, 256T, 309P, 311S, 433R, 433S, 433I, 433P, 433Q, 434H, 434F, 434Y, 252Y/254T/256E, 433K/434F/436H, 308T/309P/311S (Dall Acqua et al. Journal of Immunology, 2002, 169:5171-5180, U.S. Pat. No. 7,083,784, PCT/US97/03321, U.S. Pat. No. 6,821,505, PCT/US01/48432, U.S. Ser. No. 11/397,328, all entirely incorporated by reference), 257C, 257M, 257L, 257N, 257Y, 279E, 279Q, 279Y, insertion of Ser after 281, 283F, 284E, 306Y, 307V, 308F, 308Y 311V, 385H, 385N, (PCT/US2005/041220, U.S. Ser. No. 11/274, 065, U.S. Ser. No. 11/436,266 all entirely incorporated by reference) 204D, 284E, 285E, 286D, and 290E (PCT/US2004/037929 entirely incorporated by reference).

Preferred combinations of positions and modifications are summarized in FIG. 18.

This list of preferred Fc variants is not meant to constrain the present invention. Indeed all combinations of the any of the Fc variants provided are embodiments of the present invention. Furthermore, combinations of any of the Fc variants of the present invention with other discovered or undiscovered Fc variants may also provide favorable properties, and these combinations are also contemplated as embodiments of the present invention. Further, substitutions at all positions disclosed herein are contemplated.

Example 5

Fc Variants Comprising Amino Acid Modifications and Engineered Glycoforms that Provide Selective FcγR Affinity An alternative method to amino acid modification for modulating FcγR affinity of an Fc polypeptide is glycoform engineering. As discussed, antibodies are post-translationally modified at position 297 of the Fc region with a complex carbohydrate moiety. It is well known in the art that this glycosylation plays a role in the functional fidelity of the Fc region with respect to binding Fc ligands, particularly FcγRs and complement. It is also well established in the art that Fc polypeptide compositions that comprise a mature core carbohydrate structure which lacks fucose have improved FcγR affinity relative to compositions that comprise carbohydrate that is fucosylated (Umaña et al., 1999, Nat Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473); (U.S. Pat. No. 6,602,684; U.S. Ser. No. 10/277,370; U.S. Ser. No. 10/113,929; PCT WO 00/61739A1; PCT WO 01129246A1; PCT WO 02/31140A1; PCT WO 02/30954A1). However previous studies have shown that although reduction of fucose content improves the affinity of an IgG for human FcγRIIIa, it has no effect on binding to human FcγRI, either isoform (R131 or H131) of human FcγRIIa, or human FcγRIIb (U.S. Ser. No. 10/277,370; Shields et al., 2002, J Biol Chem 277(90):26733-26740). Recent experiments have determined that the high affinity between glycoengineered antibodies and FORM is mediated by productive interactions formed between the receptor carbohydrate attached at Asn162 and regions of the Fc that are only accessible when it is nonfucosylated. Because FcγRIIIa and FcγRIIIb are the only human Fc receptors glycosylated at this position, the proposed interactions explain the observed selective affinity increase of glycoengineered antibodies for only these receptors (Ferrara et al., 2006, J Biol Chem 281(8):5032-5036).

The data provided in Example 1 suggest that combination of glycoform engineering with FcγR selective amino acid modifications may provide Fc variants with selectively improved affinity for one or more activating receptors relative to the inhibitory receptor FcγRIIb.

In order to explore whether amino acid modification would enable such selective FcγR binding, we evaluated preferred amino acid substitutions in the context of antibodies with reduced fucose content. The Lec13 cell line (Ripka et al. Arch. Biochem. Biophys. 49:533-545 (1986)) was utilized to express human antibodies with reduced fucose content. Lec13 refers to the lectin-resistant Chinese Hamster Ovary (CHO) mutant cell line which displays a defective fucose metabolism and therefore has a diminished ability to add fucose to complex carbohydrates. That cell line is described in Ripka & Stanley, 1986, Somatic Cell & Molec. Gen. 12(1): 51-62; and Ripka et al., 1986, Arch. Biochem. Biophys. 249 (2):533-545. Lec13 cells are believed lack the transcript for GDP-D-mannose-4,6-dehydratase, a key enzyme for fucose metabolism. Ohyama et al., 1988, J. Biol. Chem. 273(23): 14582-14587. GDP-D-mannose-4,6-dehydratase generates GDP-mannose-4-keto-6-D-deoxymannose from GDP-mannose, which is then converted by the FX protein to GDP-L-fucose. Expression of fucosylated oligosaccharides is dependent on the GDP-L-fucose donor substrates and fucosyltransferase(s). The Lec13 CHO cell line is deficient in its ability to add fucose, but provides IgG with oligosaccharide which is otherwise similar to that found in normal CHO cell lines and from human serum (Jefferis, R. et al., 1990, Biochem. J. 268, 529-537; Raju, S. et al., 2000, Glycobiology 10, 477-486; Routier, F. H., et al., 1997, Glycoconj. J. 14, 201-207). Normal CHO and HEK293 cells add fucose to IgG oligosaccharide to a high degree, typically from 80-98%, and IgGs from sera are also highly fucosylated (Jefferis, R. et al., 1990, Biochem. J. 268, 529-537; Raju, S. et al., 2000, Glycobiology 10, 477-486; Routier, F. H., et al., 1997, Glycoconj. J. 14, 201-207; Shields et al., 2002, J Biol Chem 277(90): 26733-26740). It is well established that antibodies expressed in transfected Lec13 cells consistently produce about 10% fucosylated carbohydrate (Shields et al., 2002, J Biol Chem 277(90):26733-26740).

WT, G236A, and S239D/I332E variant anti-EpCAM antibodies were each transiently expressed in 293T and Lec13 cells and purified as described above. Binding affinity to human FcγRI, H131 FcγRIIa, R131 FcγRIIa, FcγRIIb, and V158 FcγRIIIa by Fc variant anti-EpCAM antibodies was measured using the SPR experiment described above. FIG. 19 provides the equilibrium constants obtained from the fits of the SPR data for all of the receptors, as well as the calculated fold KD relative to WT and the negative log of the KD (-log(KD). FIG. 20 provides a plot of the negative log of the KD for binding of the antibodies to the set of human FcγRs. The data confirm that reduced fucosylation provides an increase in affinity only for FcγRIIIa, and does not alter affinity for any of the other FcγRs. However combination of glycoengineering with a substitution that selectively improves the FcγR affinity for FcγRIIa relative to FcγRIIb, in this case G236A, provides the optimal FcγR affinity profile of selectively improved affinity for FcγRIIa and FcγRIIIa relative to the inhibitory receptor FcγRIIb. Given the macrophage phagocytosis and DC activation data provided above, this novel combination of glycoengineering and amino acid substitutions with selective FcγR affinity profiles has the potential for producing more efficacious therapeutic antibodies than glycoengineering alone.

The use of the Lec13 cell line is not meant to limit the present invention to that particular mode of reducing fucose content. A variety of other methods are known in the art for controlling the level of fucosylated and/or bisecting oligosaccharides that are covalently attached to the Fc region, including but not limited to expression in various organisms or cell lines, engineered or otherwise (for example Lec13 CHO cells or rat hybridoma YB2/0 cells), regulation of enzymes involved in the glycosylation pathway (for example FUT8 [α1,6-fucosyltranserase] and/or β1-4-N-acetylglucosaminyltransferase III [GnTIII]), and modification of modifying carbohydrate(s) after the IgG has been expressed (Umaña et al., 1999, Nat Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473); (U.S. Pat. No. 6,602,684; U.S. Ser. No. 10/277,370; U.S. Ser. No. 10/113,929; PCT WO 00/61739A1; PCT WO 01/29246A1; PCT WO 02/31140A1; PCT WO 02/30954A1).

Example 6

Additional Fc Variant Combinations

Figure 21:
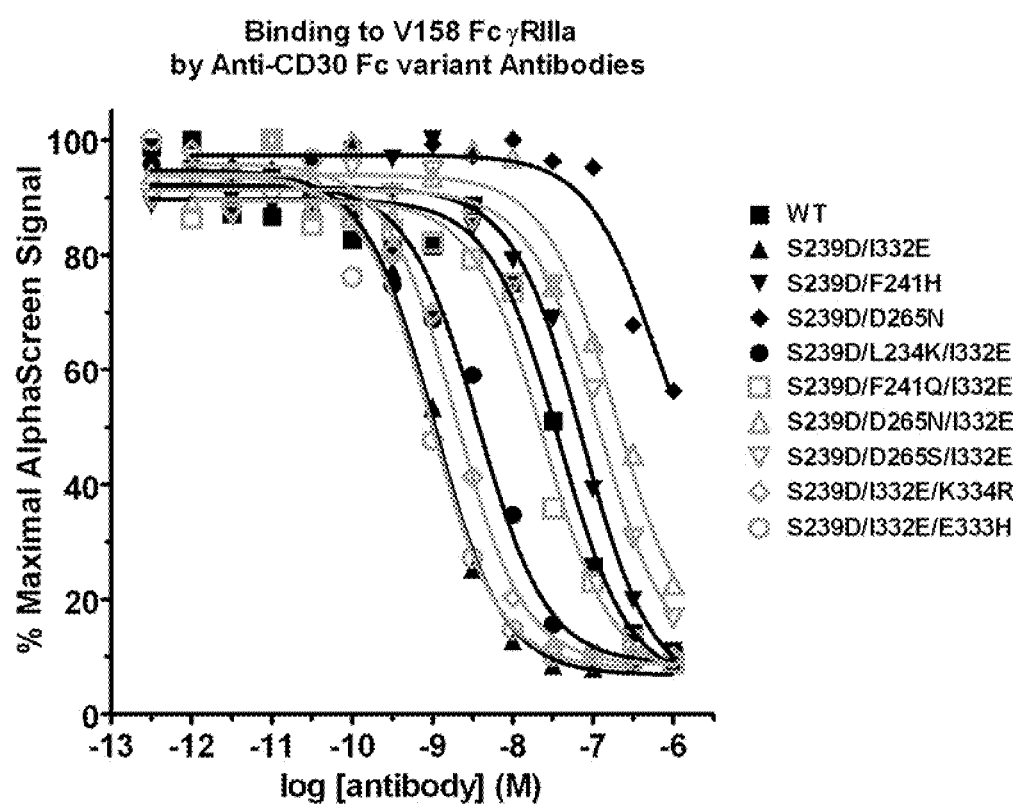
FIG. 21. Binding of select anti-CD30 Fc variants to human V158 FcγRIIIa as measured by competition AlphaScreen assay.

Substitutions were engineered in the context of the S239D, I332E, and S239D/I332E variants to explore additional Fc variants with optimized FcγR binding properties. Variants were constructed with the variable region of the anti-CD30 antibody H3.69_V2/L3.71 AC10 (SEQ IDs NO:7 and NO:8, FIGS. 27g and 27h) as disclosed in U.S. Ser. No. 60/776,598, filed Feb. 24, 2006, entitled "Optimized anti-CD30 antibodies", herein expressly incorporated by reference). Antibody variants were constructed in the IgG(hybrid) pcDNA3.1Zeo vector, expressed in 293T cells, and purified as described above. Binding affinity to human FcγRs by Fc variant anti-CD30 antibodies was measured using the competition AlphaScreen assay as described above. FIG. 21 shows binding data for select Fc variants to human V158 FcγRIIIa. FIG.

22 provides the Fold IC50's relative to WT for fits to these binding curves for all of the anti-CD30 antibody Fc variants tested.

Example 7

Mouse IgG Fc Variants with Optimized Affinity for Mouse FcγRs

The biological properties of antibodies and Fc fusions have been tested in in vivo models in order to measure a drug's efficacy for treatment against a disease or disease model, or to measure a drug's pharmacokinetics, toxicity, and other properties. A common organism used for such studies is the mouse, including but not limited to nude mice, SCID mice, xenograft mice, and transgenic mice (including knockins and knockouts). Interpretation of the results from such studies is a challenge because mouse FcγRs different substantially from human FcγRs in their homology, their expression pattern on effector cells, and their signaling biology. FIG. 23 highlights some of these key differences. FIG. 23a shows the putative expression patterns of different FcγRs on various effector cell types, and FIG. 23b shows the % identity between the human and mouse FcγR extracellular domains. Of particular importance is the existence of FcγRIV, discovered originally as CD16-2 (Mechetina et al., 2002, Immunogenetics 54:463-468) and renamed FcγRIV (Nimmerjahn & Ravetch, 2005, Science 310:1510-1512). FcγRIV is thought to be the true ortholog of human FcγRIIIa, and the two receptors are 64% identical (FIG. 23b). However whereas human FcγRIIIa is expressed on NK cells, mouse FcγRIV is not. The receptor that is expressed on mouse NK cells is FcγRIII, which shows substantially lower homology to human FcγRIIIa (49%). Interestingly, mouse FcγRIII is 93% homologous to the mouse inhibitory receptor FcγRIIb, a pair that is potentially analogous to human FcγRIIa and FcγRIIb (93% identical). However the expression pattern of mouse FcγRIII differs from that of human FcγRIIa.

These differences highlight the difficulties in interpreting results from in vivo experiments in mice using human antibodies when Fc receptor biology may affect outcome. The most optimal human antibody in humans with respect to FcγR-mediated effector function, widely viewed to be IgG1, likely does not have the optimal FcγR affinity profile for the murine receptors. Accordingly, Fc variant antibodies having optimized affinity for human Fc receptors may not provide optimal enhancements in mice, and thus may provide misleading results. The most optimal mouse FcγR affinity profile is likely provided by the most naturally optimal mouse IgG or IgGs, for example mouse IgG2a and/or IgG2b. Accordingly, engineering of mouse IgGs for optimized affinity for mouse FcγRs may provide the most informative results in in vivo experiments. In this way Fc-optimized mouse IgGs may find use as surrogate Fc-optimized antibodies in preclinical mouse models. The present invention provides mouse IgG antibodies optimized for binding to mouse FcγRs.

Fc substitutions were constructed in the context of mouse IgG1, mouse IgG2a, mouse IgG2b, and human IgG1 (FIG. 29). DNA encoding murine IgGs were obtained as IMAGE clones from the American Type Culture Collection (ATCC). Antibodies were constructed with the variable region of the anti-EGFR antibody H4.40/L3.32 C225 (SEQ IDs NO:3 and NO:4, FIGS. 27c and 27d) as disclosed in U.S. Ser. No. 60/778,226, filed Mar. 2, 2006, entitled "Optimized anti-EGFR antibodies", herein expressly incorporated by reference). Antibody variants were constructed in the pcDNA3.1Zeo vector, expressed in 293T cells, and purified as described above. FIG. 24 lists the mouse and human IgG variants that were engineered.

Figures 25, 26:
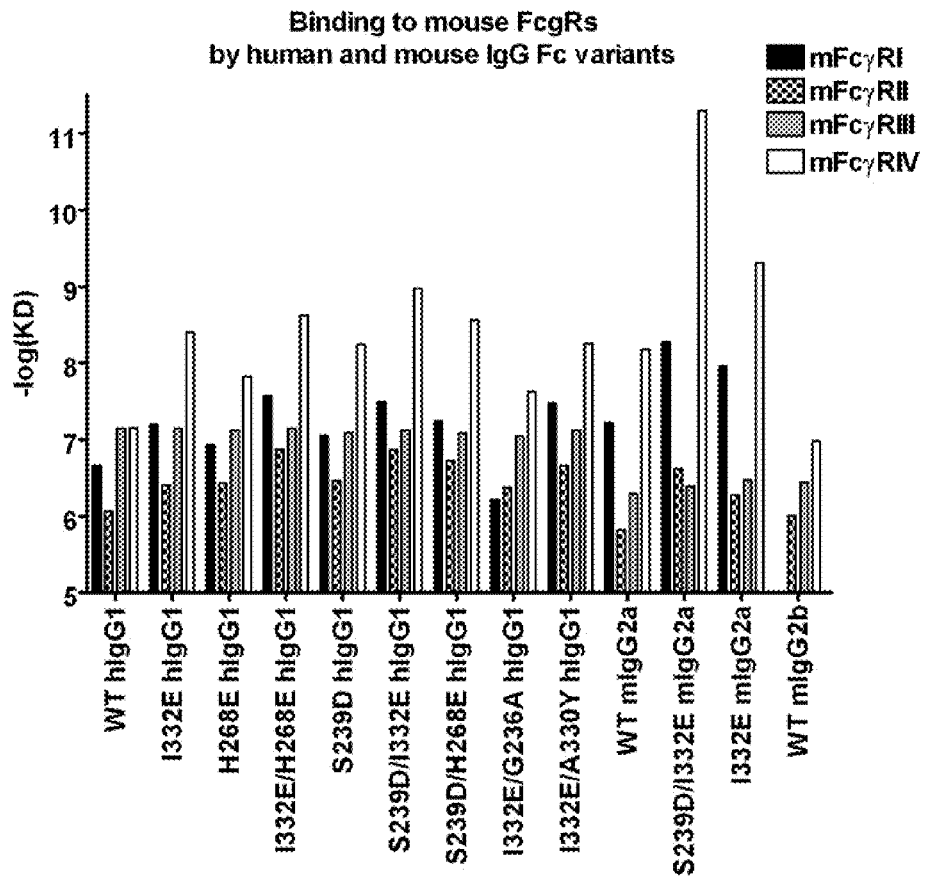
FIG. 25. Affinity data for binding of human and mouse anti-EGFR Fc variant antibodies to mouse Fc receptors FcγRI, FcγRII (FcγRIIb), FcγRIII, and FcγRIV as determined by SPR. Provided are the equilibrium dissociation constant (KD), the Fold KD relative to WT, and the negative log of the KD (-log(KD)) for each variant.
FIG. 26. Plot of the negative log of the KD for binding of human and mouse anti-EGFR Fc variant antibodies to mouse Fc receptors FcγRI, FcγRII (FcγRIIb), FcγRIII, and FcγRIV.

Binding affinities to the murine activating receptors FcγRI, FcγRIII, and FcγRIV, and the murine inhibitory receptor FcγRIIb were measured using the SPR experiment described above. His-tagged murine FcγRs were purchased commercially from R&D Systems. FIG. 25 shows equilibrium constants obtained from the fits of the SPR data for the set of murine FcγRs. Also presented is the calculated fold KD relative to WT murine IgG2a, potentially the most potent natural murine IgG antibody with respect to FcγR-mediated effector function (Hamaguchi et al., 2005, J Immunol 174: 4389-4399). FIG. 26 shows a plot of the negative log of the KD for binding of human and mouse anti-EGFR Fc variant antibodies to mouse Fc receptors FcγRI, FcγRIIb, FcγRIII, and FcγRIV. The variants provide remarkable enhancements in binding to the murine activating receptors, particularly FcγRIV, currently thought to be one of the most relevant receptors for mediating antibody-dependent effector functions in murine xencograft models (Nimmerjahn & Ravetch, 2005, Science 310:1510-1512). The results indicate that the FcγR-binding properties of the murine IgGs can be improved using the Fc variants of the present invention, and thus may provide utility for preclinical testing of antibodies and Fc fusions that comprise Fc variants with optimized Fc receptor binding properties.

All cited references are herein expressly incorporated by reference in their entirety.

Whereas particular embodiments of the invention have been described above for purposes of illustration, it will be appreciated by those skilled in the art that numerous variations of the details may be made without departing from the invention as described in the appended claims.

The invention claimed is:

1. A method of enhancing mediation of ADCP (antibody dependent cellular phagocytosis) comprising contacting a antibody with a macrophage expressing FcγRIIa, wherein said antibody comprises an Fc variant of a human parent Fc polypeptide, wherein said Fc variant comprises an amino acid substitution at position 236 in the Fc region as compared to the human parent Fc polypeptide, wherein said substitution is alanine, said Fc variant is an engineered glycoform with reduced fucose content as compared to the human parent Fc polypeptide, and said Fc variant exhibits an increase in affinity for FcγRIIa over FcγRIIb, thereby resulting in the binding of said Fc variant to FcγRIIa, wherein said increased affinity is relative to the affinity exhibited by the human parent Fc polypeptide and wherein the numbering is according to the EU index.

2. The method of claim 1, wherein said antibody is selected from the group consisting of a human antibody, a humanized antibody, and a monoclonal antibody.

3. The method of claim 1, wherein said antibody has specificity for a target antigen selected from the group consisting of Ep-CAM, CD19, CD20, CD22, CD30, CD33, CD40, CD40L, CD52, Her2/neu, EGFR, IGF-1 R, EpCAM, MUC1, GD3, CEA, CA 125, HLA-DR, MUC18, and prostate specific membrane antigen (PMSA).

* * * * *